US011369439B2

(12) United States Patent
State et al.

(10) Patent No.: US 11,369,439 B2
(45) Date of Patent: Jun. 28, 2022

(54) MEDICAL DEVICE NAVIGATION USING A VIRTUAL 3D SPACE

(71) Applicant: InnerOptic Technology, Inc., Hillsborough, NC (US)

(72) Inventors: Andrei State, Chapel Hill, NC (US); Brian Heaney, Durham, NC (US); Luv Kohli, Durham, NC (US); Kurtis Keller, Hillsborough, NC (US); Caroline Green, Chapel Hill, NC (US)

(73) Assignee: InnerOptic Technology, Inc., Hillsborough, NC (US)

( * ) Notice: Subject to any disclaimer, the term of this patent is extended or adjusted under 35 U.S.C. 154(b) by 81 days.

(21) Appl. No.: 16/985,580

(22) Filed: Aug. 5, 2020

(65) Prior Publication Data
US 2021/0113273 A1 Apr. 22, 2021

Related U.S. Application Data

(63) Continuation of application No. 16/366,537, filed on Mar. 27, 2019, now Pat. No. 10,772,686, which is a
(Continued)

(51) Int. Cl.
A61B 90/10 (2016.01)
A61B 34/20 (2016.01)
(Continued)

(52) U.S. Cl.
CPC ............ A61B 34/20 (2016.02); A61B 17/068 (2013.01); A61B 17/07207 (2013.01);
(Continued)

(58) Field of Classification Search
None
See application file for complete search history.

(56) References Cited

U.S. PATENT DOCUMENTS 3,556,079 A 1/1971 Omizo
4,058,114 A 11/1977 Soldner
(Continued)

FOREIGN PATENT DOCUMENTS

EP 0 427 358 5/1991
JP S63-290550 A 11/1988
(Continued)

OTHER PUBLICATIONS

U.S. Appl. No. 11/828,826 including its ongoing prosecution history, including without limitation Office Actions, Amendments, Remarks, and any other potentially relevant documents, filed Jul. 26, 2007, Keller et al.
(Continued)

Primary Examiner — Idowu O Osifade
(74) Attorney, Agent, or Firm — Knobbe Martens Olson & Bear, LLP

(57) ABSTRACT

A system and method for providing image guidance for placement of one or more medical devices at a target location. The system can determine one or more intersections between a medical device and an image region based at least in part on first emplacement data and second emplacement data. Using the determined intersections, the system can cause one or more displays to display perspective views of image guidance cues, including an intersection ghost in a virtual 3D space.

23 Claims, 17 Drawing Sheets

Related U.S. Application Data continuation of application No. 15/415,398, filed on Jan. 25, 2017, now Pat. No. 10,278,778.

(60) Provisional application No. 62/413,925, filed on Oct. 27, 2016.

(51) Int. Cl.

| | | |
|---|---|---|
| *A61B 17/072* | (2006.01) | |
| *A61B 90/00* | (2016.01) | |
| *A61B 17/068* | (2006.01) | |
| *A61B 17/32* | (2006.01) | |
| *A61B 17/00* | (2006.01) | |
| *A61B 34/00* | (2016.01) | |
| *A61B 90/50* | (2016.01) | |
| *A61B 34/10* | (2016.01) | |
| *A61B 34/30* | (2016.01) | |

(52) U.S. Cl.
CPC ...... *A61B 17/320016* (2013.01); *A61B 90/10* (2016.02); *A61B 90/37* (2016.02); *A61B 34/25* (2016.02); *A61B 2017/00106* (2013.01); *A61B 2017/07214* (2013.01); *A61B 2017/07271* (2013.01); *A61B 2017/320052* (2013.01); *A61B 2034/107* (2016.02); *A61B 2034/2048* (2016.02); *A61B 2034/2051* (2016.02); *A61B 2034/2055* (2016.02); *A61B 2034/2065* (2016.02); *A61B 2034/302* (2016.02); *A61B 2090/365* (2016.02); *A61B 2090/367* (2016.02); *A61B 2090/3612* (2016.02); *A61B 2090/372* (2016.02); *A61B 2090/378* (2016.02); *A61B 2090/3782* (2016.02); *A61B 2090/3937* (2016.02); *A61B 2090/502* (2016.02)

(56) References Cited

U.S. PATENT DOCUMENTS

| | | | |
|---|---|---|---|
| RE30,397 | E | 9/1980 | King |
| 4,249,539 | A | 2/1981 | Vilkomerson et al. |
| 4,294,544 | A | 10/1981 | Altschuler et al. |
| 4,390,025 | A | 6/1983 | Takemura et al. |
| 4,407,294 | A | 10/1983 | Vilkomerso |
| 4,431,006 | A | 2/1984 | Trimmer et al. |
| 4,567,896 | A | 2/1986 | Barnea et al. |
| 4,583,538 | A | 4/1986 | Onik et al. |
| 4,620,546 | A | 11/1986 | Aida et al. |
| 4,671,292 | A | 6/1987 | Matzuk |
| 4,839,836 | A | 6/1989 | Fonsalas |
| 4,862,873 | A | 9/1989 | Yajima et al. |
| 4,884,219 | A | 11/1989 | Waldren |
| 4,899,756 | A | 2/1990 | Sonek |
| 4,911,173 | A | 3/1990 | Terwillige |
| 4,945,305 | A | 7/1990 | Blood |
| 5,076,279 | A | 12/1991 | Arenson et al. |
| 5,078,140 | A | 1/1992 | Kwoh |
| 5,078,142 | A | 1/1992 | Siczek et al. |
| 5,095,910 | A | 3/1992 | Powers |
| 5,109,276 | A | 4/1992 | Nudelman et al. |
| 5,158,088 | A | 10/1992 | Nelson et al. |
| 5,161,536 | A | 11/1992 | Vikomerson et al. |
| 5,193,120 | A | 3/1993 | Gamache et al. |
| 5,209,235 | A | 5/1993 | Brisken et al. |
| 5,249,581 | A | 10/1993 | Horbal et al. |
| 5,251,127 | A | 10/1993 | Raab |
| 5,261,404 | A | 11/1993 | Mick et al. |
| 5,265,610 | A | 11/1993 | Darrow et al. |
| 5,271,400 | A | 12/1993 | Dumoulin et al. |
| 5,307,153 | A | 4/1994 | Maruyama et al. |
| 5,309,913 | A | 5/1994 | Kormos et al. |
| 5,323,002 | A | 6/1994 | Sampsell et al. |
| 5,371,543 | A | 12/1994 | Anderson |
| 5,383,454 | A | 1/1995 | Bucholz |
| 5,394,875 | A | 3/1995 | Lewis et al. |
| 5,411,026 | A | 5/1995 | Carol |
| 5,433,198 | A | 7/1995 | Desai |
| 5,433,739 | A | 7/1995 | Sluijter |
| 5,443,489 | A | 8/1995 | Ben-Haim |
| 5,446,798 | A | 8/1995 | Morita et al. |
| 5,447,154 | A | 9/1995 | Cinquin et al. |
| 5,452,024 | A | 9/1995 | Sampsell |
| 5,457,493 | A | 10/1995 | Leddy et al. |
| 5,474,073 | A | 12/1995 | Schwartz et al. |
| 5,476,096 | A | 12/1995 | Olstad et al. |
| 5,483,961 | A | 1/1996 | Kelly et al. |
| 5,488,431 | A | 1/1996 | Gove et al. |
| 5,489,952 | A | 2/1996 | Gove et al. |
| 5,491,510 | A | 2/1996 | Gove |
| 5,494,039 | A | 2/1996 | Onik et al. |
| 5,503,152 | A | 4/1996 | Oakley et al. |
| 5,505,204 | A | 4/1996 | Picot et al. |
| 5,515,856 | A | 5/1996 | Olstad et al. |
| 5,517,990 | A | 5/1996 | Kalfas et al. |
| 5,526,051 | A | 6/1996 | Gove et al. |
| 5,526,812 | A | 6/1996 | Dumoulin et al. |
| 5,529,070 | A | 6/1996 | Augustine et al. |
| 5,531,227 | A | 7/1996 | Schneider |
| 5,532,997 | A | 7/1996 | Pauli |
| 5,541,723 | A | 7/1996 | Tanaka |
| 5,558,091 | A | 9/1996 | Acker et al. |
| 5,568,811 | A | 10/1996 | Olstad |
| 5,570,135 | A | 10/1996 | Gove et al. |
| 5,579,026 | A | 11/1996 | Tabata |
| 5,581,271 | A | 12/1996 | Kraemer |
| 5,588,948 | A | 12/1996 | Takahashi et al. |
| 5,608,468 | A | 3/1997 | Gove et al. |
| 5,608,849 | A | 3/1997 | King, Jr. |
| 5,611,345 | A | 3/1997 | Hibbeln |
| 5,611,353 | A | 3/1997 | Dance et al. |
| 5,612,753 | A | 3/1997 | Poradish et al. |
| 5,625,408 | A | 4/1997 | Matsugu et al. |
| 5,628,327 | A | 5/1997 | Unger et al. |
| 5,629,794 | A | 5/1997 | Magel et al. |
| 5,630,027 | A | 5/1997 | Venkateswar et al. |
| 5,647,361 | A | 7/1997 | Damadian |
| 5,647,373 | A | 7/1997 | Paltieli et al. |
| 5,660,185 | A | 8/1997 | Shmulewitz et al. |
| 5,662,111 | A | 9/1997 | Cosman |
| 5,699,444 | A | 12/1997 | Palm |
| 5,701,898 | A | 12/1997 | Adam et al. |
| 5,701,900 | A | 12/1997 | Shehada et al. |
| 5,726,670 | A | 3/1998 | Tabata et al. |
| 5,728,044 | A | 3/1998 | Shan |
| 5,758,650 | A | 6/1998 | Miller et al. |
| 5,766,135 | A | 6/1998 | Terwilliger |
| 5,784,098 | A | 7/1998 | Shoji et al. |
| 5,792,147 | A | 8/1998 | Evans et al. |
| 5,793,701 | A | 8/1998 | Wright et al. |
| 5,797,849 | A | 8/1998 | Vesely et al. |
| 5,806,521 | A | 9/1998 | Morimoto et al. |
| 5,807,395 | A | 9/1998 | Mulier et al. |
| 5,810,008 | A | 9/1998 | Dekel et al. |
| 5,817,022 | A | 10/1998 | Vesely |
| 5,820,554 | A | 10/1998 | Davis et al. |
| 5,820,561 | A | 10/1998 | Olstad et al. |
| 5,829,439 | A | 11/1998 | Yokosawa et al. |
| 5,829,444 | A | 11/1998 | Ferre et al. |
| 5,851,183 | A | 12/1998 | Bodiolz |
| 5,870,136 | A | 2/1999 | Fuchs et al. |
| 5,891,034 | A | 4/1999 | Bucholz |
| 5,920,395 | A | 7/1999 | Schulz |
| 5,961,527 | A | 10/1999 | Whitmore, III et al. |
| 5,967,980 | A | 10/1999 | Ferre et al. |
| 5,967,991 | A | 10/1999 | Gardineer et al. |
| 5,991,085 | A | 11/1999 | Rallison et al. |
| 6,016,439 | A | 1/2000 | Acker |
| 6,019,724 | A | 2/2000 | Gronningsaeter et al. |
| 6,048,312 | A | 4/2000 | Ishrak et al. |
| 6,064,749 | A | 5/2000 | Hirota et al. |
| 6,091,546 | A | 7/2000 | Spitzer |
| 6,095,982 | A | 8/2000 | Richards-Kortum et al. |

(56) References Cited

U.S. PATENT DOCUMENTS

| | | |
|---|---|---|
| 6,099,471 A | 8/2000 | Torp et al. |
| 6,108,130 A | 8/2000 | Raj |
| 6,122,538 A | 9/2000 | Sliwa, Jr. et al. |
| 6,122,541 A | 9/2000 | Cosman et al. |
| 6,160,666 A | 12/2000 | Rallison et al. |
| 6,167,296 A | 12/2000 | Shahidi |
| 6,181,371 B1 | 1/2001 | Maguire, Jr. |
| RE37,088 E | 3/2001 | Olstad et al. |
| 6,216,029 B1 | 4/2001 | Paltieli |
| 6,241,725 B1 | 6/2001 | Cosman |
| 6,245,017 B1 | 6/2001 | Hashimoto et al. |
| 6,246,784 B1 | 6/2001 | Summers et al. |
| 6,246,898 B1 | 6/2001 | Vesely et al. |
| 6,248,101 B1 | 6/2001 | Witmore, III et al. |
| 6,261,234 B1 | 7/2001 | Lin |
| 6,341,016 B1 | 1/2002 | Malione |
| 6,348,058 B1 | 2/2002 | Melken et al. |
| 6,350,238 B1 | 2/2002 | Olstad et al. |
| 6,352,507 B1 | 3/2002 | Torp et al. |
| 6,379,302 B1 | 4/2002 | Kessman et al. |
| 6,385,475 B1 | 5/2002 | Cinquin et al. |
| 6,442,417 B1 | 8/2002 | Shahidi et al. |
| 6,447,450 B1 | 9/2002 | Olsdat |
| 6,456,868 B2 | 9/2002 | Saito et al. |
| 6,470,207 B1 | 10/2002 | Simon et al. |
| 6,471,366 B1 | 10/2002 | Hughson et al. |
| 6,477,400 B1 | 11/2002 | Barrick |
| 6,478,793 B1 | 11/2002 | Cosman et al. |
| 6,503,195 B1 | 1/2003 | Keller et al. |
| 6,511,418 B2 | 1/2003 | Shahidi et al. |
| 6,517,485 B2 | 2/2003 | Torp et al. |
| 6,518,939 B1 | 2/2003 | Kikuchi |
| 6,527,443 B1 | 3/2003 | Vilsmeier |
| 6,529,758 B2 | 3/2003 | Shahidi |
| 6,537,217 B1 | 3/2003 | Bjaerum et al. |
| 6,545,706 B1 | 4/2003 | Edwards et al. |
| 6,546,279 B1 | 4/2003 | Bova et al. |
| 6,551,325 B2 | 4/2003 | Neubauer et al. |
| 6,570,566 B1 | 5/2003 | Yoshigahara |
| 6,575,969 B1 | 6/2003 | Rittman, III et al. |
| 6,579,240 B2 | 6/2003 | Bjaerum et al. |
| 6,587,711 B1 | 7/2003 | Alfano et al. |
| 6,591,130 B2 | 7/2003 | Shahidi |
| 6,592,522 B2 | 7/2003 | Bjaerum et al. |
| 6,594,517 B1 | 7/2003 | Nevo |
| 6,597,818 B2 | 7/2003 | Kumar et al. |
| 6,604,404 B2 | 8/2003 | Paltieli et al. |
| 6,616,610 B2 | 9/2003 | Steininger et al. |
| 6,626,832 B1 | 9/2003 | Paltieli et al. |
| 6,652,462 B2 | 11/2003 | Bjaerum et al. |
| 6,669,635 B2 | 12/2003 | Kessman et al. |
| 6,676,599 B2 | 1/2004 | Torp et al. |
| 6,689,067 B2 | 2/2004 | Sauer et al. |
| 6,695,786 B2 | 2/2004 | Wang et al. |
| 6,711,429 B1 | 3/2004 | Gilboa et al. |
| 6,725,082 B2 | 4/2004 | Sati et al. |
| 6,733,458 B1 | 5/2004 | Steins et al. |
| 6,764,449 B2 | 7/2004 | Lee et al. |
| 6,766,184 B2 | 7/2004 | Utzinger et al. |
| 6,768,496 B2 | 7/2004 | Bieger et al. |
| 6,775,404 B1 | 8/2004 | Pagoulatos et al. |
| 6,782,287 B2 | 8/2004 | Grzeszczuk et al. |
| 6,783,524 B2 | 8/2004 | Anderson et al. |
| 6,827,723 B2 | 12/2004 | Carson |
| 6,863,655 B2 | 3/2005 | Bjaerum et al. |
| 6,873,867 B2 | 3/2005 | Vilsmeier |
| 6,875,179 B2 | 4/2005 | Ferguson et al. |
| 6,881,214 B2 | 4/2005 | Cosman et al. |
| 6,895,268 B1 | 5/2005 | Rahn et al. |
| 6,915,150 B2 | 7/2005 | Cinquin et al. |
| 6,917,827 B2 | 7/2005 | Kienzle, III |
| 6,923,817 B2 | 8/2005 | Carson et al. |
| 6,936,048 B2 | 8/2005 | Hurst |
| 6,947,783 B2 | 9/2005 | Immerz |
| 6,968,224 B2 | 11/2005 | Kessman et al. |
| 6,978,167 B2 | 12/2005 | Dekel et al. |
| 7,008,373 B2 | 3/2006 | Stoianovici et al. |
| 7,033,360 B2 | 4/2006 | Cinquin et al. |
| 7,072,707 B2 | 7/2006 | Galloway, Jr. et al. |
| 7,077,807 B2 | 7/2006 | Torp et al. |
| 7,093,012 B2 | 8/2006 | Oltad et al. |
| 7,110,013 B2 | 9/2006 | Ebersole et al. |
| 7,171,255 B2 | 1/2007 | Holupka et al. |
| 7,209,776 B2 | 4/2007 | Leitner |
| 7,245,746 B2 | 7/2007 | Bjaerum et al. |
| 7,248,232 B1 | 7/2007 | Yamazaki et al. |
| 7,261,694 B2 | 8/2007 | Torp et al. |
| 7,313,430 B2 | 12/2007 | Urquhart et al. |
| 7,331,932 B2 | 2/2008 | Leitner |
| 7,351,205 B2 | 4/2008 | Szczech et al. |
| 7,379,769 B2 | 5/2008 | Piron et al. |
| 7,385,708 B2 | 6/2008 | Ackerman et al. |
| 7,392,076 B2 | 6/2008 | Moctezuma de la Barrera |
| 7,398,116 B2 | 7/2008 | Edwards |
| 7,466,303 B2 | 12/2008 | Yi et al. |
| 7,480,533 B2 | 1/2009 | Cosman et al. |
| 7,505,809 B2 | 3/2009 | Strommer et al. |
| 7,588,541 B2 | 9/2009 | Floyd et al. |
| 7,596,267 B2 | 9/2009 | Accomazzi et al. |
| 7,652,259 B2 | 1/2010 | Kimchy et al. |
| 7,662,128 B2 | 2/2010 | Salcudean et al. |
| 7,678,052 B2 | 3/2010 | Torp et al. |
| 7,728,868 B2 | 6/2010 | Razzaque et al. |
| 7,747,305 B2 | 6/2010 | Dean et al. |
| 7,797,032 B2 | 9/2010 | Martinelli et al. |
| 7,798,965 B2 | 9/2010 | Torp et al. |
| 7,833,168 B2 | 11/2010 | Taylor et al. |
| 7,833,221 B2 | 11/2010 | Voegele et al. |
| 7,846,103 B2 | 12/2010 | Cannon, Jr. et al. |
| 7,876,942 B2 | 1/2011 | Gilboa |
| 7,889,905 B2 | 2/2011 | Higgins et al. |
| 7,912,849 B2 | 3/2011 | Ohrn et al. |
| 7,920,909 B2 | 4/2011 | Lyon et al. |
| 7,962,193 B2 | 6/2011 | Edwards et al. |
| 7,976,469 B2 | 7/2011 | Bonde et al. |
| 8,023,712 B2 | 9/2011 | Ikuma et al. |
| 8,038,631 B1 | 10/2011 | Sanghvi et al. |
| 8,041,413 B2 | 10/2011 | Barbagli et al. |
| 8,050,736 B2 | 11/2011 | Piron et al. |
| 8,052,636 B2 | 11/2011 | Moll et al. |
| 8,066,644 B2 | 11/2011 | Sarkar et al. |
| 8,073,528 B2 | 12/2011 | Zhao et al. |
| 8,086,298 B2 | 12/2011 | Whitmore, III et al. |
| 8,135,669 B2 | 3/2012 | Olstad et al. |
| 8,137,281 B2 | 3/2012 | Huang et al. |
| 8,147,408 B2 | 4/2012 | Bunce et al. |
| 8,152,724 B2 | 4/2012 | Ridley et al. |
| 8,167,805 B2 | 5/2012 | Emery et al. |
| 8,216,149 B2 | 7/2012 | Oonuki et al. |
| 8,221,322 B2 | 7/2012 | Wang et al. |
| 8,228,028 B2 | 7/2012 | Schneider |
| 8,257,264 B2 | 9/2012 | Park et al. |
| 8,296,797 B2 | 10/2012 | Olstad et al. |
| 8,340,379 B2 | 12/2012 | Razzaque et al. |
| 8,350,902 B2 | 1/2013 | Razzaque et al. |
| 8,482,606 B2 | 7/2013 | Razzaque et al. |
| 8,554,307 B2 | 10/2013 | Razzaque et al. |
| 8,585,598 B2 | 11/2013 | Razzaque et al. |
| 8,641,621 B2 | 2/2014 | Razzaque et al. |
| 8,670,816 B2 | 3/2014 | Green et al. |
| 8,690,776 B2 | 4/2014 | Razzaque et al. |
| 8,831,310 B2 | 9/2014 | Razzaque et al. |
| 9,107,698 B2 | 8/2015 | Razzaque et al. |
| 9,265,572 B2 | 2/2016 | Fuchs et al. |
| 9,282,947 B2 | 3/2016 | Razzaque et al. |
| 9,364,294 B2 | 6/2016 | Razzaque et al. |
| 9,398,936 B2 | 7/2016 | Razzaque et al. |
| 9,659,345 B2 | 5/2017 | Razzaque et al. |
| 9,675,319 B1 | 6/2017 | Razzaque et al. |
| 9,901,406 B2 | 2/2018 | State et al. |
| 9,949,700 B2 | 4/2018 | Razzaque et al. |
| 10,127,629 B2 | 11/2018 | Razzaque et al. |
| 10,136,951 B2 | 11/2018 | Razzaque et al. |
| 10,188,467 B2 | 1/2019 | Razzaque et al. |

(56) References Cited

U.S. PATENT DOCUMENTS

| | | |
|---|---|---|
| 10,278,778 B2 | 5/2019 | State et al. |
| 10,314,559 B2 | 6/2019 | Razzaque et al. |
| 10,398,513 B2 | 9/2019 | Razzaque et al. |
| 10,433,814 B2 | 10/2019 | Razzaque et al. |
| 10,733,700 B2 | 8/2020 | Keller et al. |
| 10,772,686 B2 | 9/2020 | State et al. |
| 10,820,944 B2 | 11/2020 | State et al. |
| 10,820,946 B2 | 11/2020 | Heaney et al. |
| 2001/0007919 A1 | 7/2001 | Shahidi |
| 2001/0016804 A1 | 8/2001 | Cunningham et al. |
| 2001/0031920 A1 | 10/2001 | Kaufman et al. |
| 2001/0041838 A1 | 11/2001 | Holupka et al. |
| 2001/0045979 A1 | 11/2001 | Matsumoto et al. |
| 2002/0010384 A1 | 1/2002 | Shahidi et al. |
| 2002/0032772 A1 | 3/2002 | Olstad et al. |
| 2002/0049375 A1 | 4/2002 | Strommer et al. |
| 2002/0077540 A1 | 6/2002 | Kienzle, III |
| 2002/0077543 A1 | 6/2002 | Grzeszczuk et al. |
| 2002/0103431 A1 | 8/2002 | Toker et al. |
| 2002/0105484 A1 | 8/2002 | Navab et al. |
| 2002/0135673 A1 | 9/2002 | Favalora et al. |
| 2002/0138008 A1 | 9/2002 | Tsujita et al. |
| 2002/0140814 A1 | 10/2002 | Cohen-Solal et al. |
| 2002/0156375 A1 | 10/2002 | Kessmam et al. |
| 2002/0198451 A1 | 12/2002 | Carson |
| 2003/0032878 A1 | 2/2003 | Shahidi |
| 2003/0040743 A1 | 2/2003 | Cosman et al. |
| 2003/0073901 A1 | 4/2003 | Simon et al. |
| 2003/0135119 A1 | 7/2003 | Lee et al. |
| 2003/0163142 A1 | 8/2003 | Paltieli et al. |
| 2003/0164172 A1 | 9/2003 | Chumas et al. |
| 2003/0231789 A1 | 12/2003 | Willis et al. |
| 2003/0233123 A1 | 12/2003 | Kindlein et al. |
| 2004/0034313 A1 | 2/2004 | Leitner |
| 2004/0078036 A1 | 4/2004 | Keidar |
| 2004/0095507 A1 | 5/2004 | Bishop et al. |
| 2004/0116810 A1 | 6/2004 | Olstad |
| 2004/0147920 A1 | 7/2004 | Keidar |
| 2004/0152970 A1 | 8/2004 | Hunter et al. |
| 2004/0181144 A1 | 9/2004 | Cinquin et al. |
| 2004/0215071 A1 | 10/2004 | Frank et al. |
| 2004/0238732 A1 | 12/2004 | State et al. |
| 2004/0243146 A1 | 12/2004 | Chesbrough et al. |
| 2004/0243148 A1 | 12/2004 | Wasielewski |
| 2004/0249281 A1 | 12/2004 | Olstad |
| 2004/0249282 A1 | 12/2004 | Olstad |
| 2004/0254454 A1 | 12/2004 | Kockro |
| 2005/0010098 A1 | 1/2005 | Frigstad et al. |
| 2005/0085717 A1 | 4/2005 | Shahidi |
| 2005/0085718 A1 | 4/2005 | Shahidi |
| 2005/0090733 A1 | 4/2005 | Van Der Lugt et al. |
| 2005/0090742 A1 | 4/2005 | Yoshitaka et al. |
| 2005/0107679 A1 | 5/2005 | Geiger et al. |
| 2005/0111733 A1 | 5/2005 | Fors et al. |
| 2005/0159641 A1 | 7/2005 | Kanai |
| 2005/0182316 A1 | 8/2005 | Burdette et al. |
| 2005/0192564 A1 | 9/2005 | Cosman et al. |
| 2005/0219552 A1 | 10/2005 | Ackerman et al. |
| 2005/0222574 A1 | 10/2005 | Giordano et al. |
| 2005/0231532 A1 | 10/2005 | Suzuki et al. |
| 2005/0240094 A1 | 10/2005 | Pichon et al. |
| 2005/0251148 A1 | 11/2005 | Friedrich |
| 2006/0004275 A1 | 1/2006 | Vija et al. |
| 2006/0020204 A1 | 1/2006 | Serra et al. |
| 2006/0036162 A1 | 2/2006 | Shahidi et al. |
| 2006/0052792 A1 | 3/2006 | Boettiger et al. |
| 2006/0058609 A1 | 3/2006 | Olstad |
| 2006/0058610 A1 | 3/2006 | Olstad |
| 2006/0058674 A1 | 3/2006 | Olstad |
| 2006/0058675 A1 | 3/2006 | Olstad |
| 2006/0100505 A1 | 5/2006 | Viswanathan |
| 2006/0122495 A1 | 6/2006 | Kienzle |
| 2006/0184040 A1 | 8/2006 | Keller et al. |
| 2006/0193504 A1 | 8/2006 | Saigo et al. |
| 2006/0229594 A1 | 10/2006 | Francischelli et al. |
| 2006/0235290 A1 | 10/2006 | Gabriel et al. |
| 2006/0235538 A1 | 10/2006 | Rochetin et al. |
| 2006/0241450 A1 | 10/2006 | Da Silva et al. |
| 2006/0253030 A1 | 11/2006 | Altmann et al. |
| 2006/0253032 A1 | 11/2006 | Altmann et al. |
| 2006/0271056 A1 | 11/2006 | Terrill-Grisoni et al. |
| 2006/0282023 A1 | 12/2006 | Leitner |
| 2006/0293643 A1 | 12/2006 | Wallace et al. |
| 2007/0002582 A1 | 1/2007 | Burwell et al. |
| 2007/0016035 A1 | 1/2007 | Hashimoto |
| 2007/0024617 A1 | 2/2007 | Poole |
| 2007/0032906 A1 | 2/2007 | Sutherland et al. |
| 2007/0073155 A1 | 3/2007 | Park et al. |
| 2007/0073455 A1 | 3/2007 | Oyobe et al. |
| 2007/0078346 A1 | 4/2007 | Park et al. |
| 2007/0167699 A1 | 7/2007 | Lathuiliere et al. |
| 2007/0167701 A1 | 7/2007 | Sherman |
| 2007/0167705 A1 | 7/2007 | Chiang et al. |
| 2007/0167771 A1 | 7/2007 | Olstad |
| 2007/0167801 A1 | 7/2007 | Webler et al. |
| 2007/0225553 A1 | 9/2007 | Shahidi |
| 2007/0239281 A1 | 10/2007 | Gotte et al. |
| 2007/0244488 A1 | 10/2007 | Metzger et al. |
| 2007/0255136 A1 | 11/2007 | Kristofferson et al. |
| 2007/0270718 A1 | 11/2007 | Rochetin et al. |
| 2007/0276234 A1 | 11/2007 | Shahidi |
| 2007/0291000 A1 | 12/2007 | Liang et al. |
| 2008/0004481 A1 | 1/2008 | Bax et al. |
| 2008/0004516 A1 | 1/2008 | DiSilvestro et al. |
| 2008/0030578 A1 | 2/2008 | Razzaque et al. |
| 2008/0039723 A1 | 2/2008 | Suri et al. |
| 2008/0051910 A1 | 2/2008 | Kammerzell et al. |
| 2008/0091106 A1 | 4/2008 | Kim et al. |
| 2008/0114235 A1 | 5/2008 | Unal et al. |
| 2008/0146939 A1 | 6/2008 | McMorrow et al. |
| 2008/0161824 A1 | 7/2008 | McMillen |
| 2008/0183080 A1 | 7/2008 | Abraham |
| 2008/0200794 A1 | 8/2008 | Teichman et al. |
| 2008/0208031 A1 | 8/2008 | Kurpad et al. |
| 2008/0208081 A1 | 8/2008 | Murphy et al. |
| 2008/0214932 A1 | 9/2008 | Mollard et al. |
| 2008/0232679 A1 | 9/2008 | Hahn et al. |
| 2008/0287794 A1 | 11/2008 | Li et al. |
| 2008/0287805 A1 | 11/2008 | Li |
| 2008/0287837 A1 | 11/2008 | Makin et al. |
| 2009/0024030 A1 | 1/2009 | Lachaine et al. |
| 2009/0036902 A1 | 2/2009 | DeMaio et al. |
| 2009/0105597 A1 | 4/2009 | Abraham |
| 2009/0118613 A1 | 5/2009 | Krugman et al. |
| 2009/0118724 A1 | 5/2009 | Zvuloni et al. |
| 2009/0131783 A1 | 5/2009 | Jenkins et al. |
| 2009/0137907 A1 | 5/2009 | Takimoto et al. |
| 2009/0196480 A1 | 8/2009 | Nields et al. |
| 2009/0234369 A1 | 9/2009 | Bax et al. |
| 2009/0312629 A1 | 12/2009 | Razzaque et al. |
| 2010/0045783 A1 | 2/2010 | State et al. |
| 2010/0152570 A1 | 6/2010 | Navab |
| 2010/0185087 A1 | 7/2010 | Nields et al. |
| 2010/0198045 A1 | 8/2010 | Razzaque et al. |
| 2010/0198402 A1 | 8/2010 | Greer et al. |
| 2010/0208963 A1 | 8/2010 | Kruecker et al. |
| 2010/0268072 A1 | 10/2010 | Hall et al. |
| 2010/0268085 A1 | 10/2010 | Kruecker et al. |
| 2010/0296718 A1 | 11/2010 | Ostrovsky-Berman et al. |
| 2010/0298705 A1 | 11/2010 | Pelissier et al. |
| 2010/0305448 A1 | 12/2010 | Dagonnau et al. |
| 2010/0312121 A1 | 12/2010 | Guan |
| 2010/0331252 A1 | 12/2010 | Hamrick |
| 2011/0043612 A1 | 2/2011 | Keller et al. |
| 2011/0046483 A1 | 2/2011 | Fuchs et al. |
| 2011/0046486 A1 | 2/2011 | Shin et al. |
| 2011/0057930 A1 | 3/2011 | Keller |
| 2011/0082351 A1 | 4/2011 | Razzaque et al. |
| 2011/0201915 A1 | 8/2011 | Gogin et al. |
| 2011/0201976 A1 | 8/2011 | Sanghvi et al. |
| 2011/0208055 A1 | 8/2011 | Dalal et al. |
| 2011/0230351 A1 | 9/2011 | Fischer et al. |
| 2011/0237947 A1 | 9/2011 | Boctor et al. |
| 2011/0238043 A1 | 9/2011 | Kleven |

(56) References Cited

U.S. PATENT DOCUMENTS

| | | |
|---|---|---|
| 2011/0251483 A1 | 10/2011 | Razzaque et al. |
| 2011/0274324 A1 | 11/2011 | Clements et al. |
| 2011/0282188 A1 | 11/2011 | Burnside et al. |
| 2011/0288412 A1 | 11/2011 | Deckman et al. |
| 2011/0295108 A1 | 12/2011 | Cox et al. |
| 2011/0301451 A1 | 12/2011 | Rohling |
| 2012/0035473 A1 | 2/2012 | Sanghvi et al. |
| 2012/0059260 A1 | 3/2012 | Robinson |
| 2012/0071759 A1 | 3/2012 | Hagy et al. |
| 2012/0078094 A1 | 3/2012 | Nishina et al. |
| 2012/0108955 A1 | 5/2012 | Razzaque et al. |
| 2012/0138658 A1* | 6/2012 | Ullrich .................. A61B 34/76 227/175.1 |
| 2012/0143029 A1 | 6/2012 | Silverstein et al. |
| 2012/0143055 A1 | 6/2012 | Ng et al. |
| 2012/0165679 A1 | 6/2012 | Orome et al. |
| 2012/0215096 A1 | 8/2012 | Gilboa |
| 2012/0230559 A1 | 9/2012 | Itai |
| 2012/0237105 A1 | 9/2012 | Mielekamp |
| 2012/0259210 A1 | 10/2012 | Harhen et al. |
| 2013/0030286 A1 | 1/2013 | Alouani et al. |
| 2013/0044930 A1 | 2/2013 | Li et al. |
| 2013/0079770 A1 | 3/2013 | Kyle, Jr. et al. |
| 2013/0090646 A1 | 4/2013 | Moss et al. |
| 2013/0096497 A1 | 4/2013 | Duindam et al. |
| 2013/0132374 A1 | 5/2013 | Olstad et al. |
| 2013/0144165 A1 | 6/2013 | Ebbini et al. |
| 2013/0151533 A1 | 6/2013 | Udupa et al. |
| 2013/0178745 A1 | 7/2013 | Kyle et al. |
| 2013/0218024 A1 | 8/2013 | Boctor et al. |
| 2013/0249787 A1 | 9/2013 | Morimoto |
| 2014/0016848 A1 | 1/2014 | Razzaque et al. |
| 2014/0051987 A1 | 2/2014 | Kowshik et al. |
| 2014/0058387 A1 | 2/2014 | Kruecker et al. |
| 2014/0078138 A1 | 3/2014 | Martin et al. |
| 2014/0180074 A1 | 6/2014 | Green |
| 2014/0201669 A1 | 7/2014 | Liu et al. |
| 2014/0275760 A1 | 9/2014 | Lee et al. |
| 2014/0275810 A1 | 9/2014 | Keller et al. |
| 2014/0275997 A1 | 9/2014 | Chopra et al. |
| 2014/0343404 A1 | 11/2014 | Razzaque et al. |
| 2014/0350390 A1 | 11/2014 | Kudavelly et al. |
| 2015/0238259 A1 | 8/2015 | Albeck et al. |
| 2015/0257847 A1 | 9/2015 | Higgins et al. |
| 2016/0117857 A1 | 4/2016 | State et al. |
| 2016/0166334 A1 | 6/2016 | Razzaque |
| 2016/0166336 A1 | 6/2016 | Razzaque |
| 2016/0196694 A1 | 7/2016 | Lindeman |
| 2016/0270862 A1 | 9/2016 | Fuchs et al. |
| 2017/0024903 A1 | 1/2017 | Razzaque |
| 2017/0065352 A1 | 3/2017 | Razzaque |
| 2017/0099479 A1 | 4/2017 | Browd et al. |
| 2017/0128139 A1 | 5/2017 | Razzaque et al. |
| 2017/0323424 A1 | 11/2017 | Razzaque et al. |
| 2017/0348067 A1* | 12/2017 | Krimsky ................ A61B 34/10 |
| 2017/0360395 A1 | 12/2017 | Razzaque et al. |
| 2018/0263713 A1 | 9/2018 | State |
| 2018/0289344 A1 | 10/2018 | Green et al. |
| 2019/0021681 A1 | 1/2019 | Kohli |
| 2019/0060001 A1 | 2/2019 | Kohli et al. |
| 2019/0167354 A1 | 6/2019 | Heaney et al. |
| 2019/0180411 A1 | 6/2019 | Keller |
| 2019/0216547 A1 | 7/2019 | Heaney et al. |
| 2019/0223958 A1 | 7/2019 | Kohli |
| 2019/0247130 A1 | 8/2019 | State |
| 2019/0321107 A1 | 10/2019 | State et al. |
| 2020/0046315 A1 | 2/2020 | State |
| 2020/0138402 A1 | 5/2020 | Kohli |

FOREIGN PATENT DOCUMENTS

| | | |
|---|---|---|
| JP | H07-116164 A | 5/1995 |
| JP | 2005-058584 | 3/2005 |
| JP | 2005-323669 | 11/2005 |
| JP | 2009-517177 | 4/2009 |
| WO | WO 96/005768 | 2/1996 |
| WO | WO 97/015249 | 5/1997 |
| WO | WO 97/017014 | 5/1997 |
| WO | WO 97/029682 | 8/1997 |
| WO | WO 99/26534 | 6/1999 |
| WO | WO 01/039683 | 6/2001 |
| WO | WO 03/032837 | 4/2003 |
| WO | WO 03/034705 | 4/2003 |
| WO | WO 03/105289 | 12/2003 |
| WO | WO 05/010711 | 2/2005 |
| WO | WO 07/019216 | 2/2007 |
| WO | WO 07/067323 A2 | 6/2007 |
| WO | WO 07/067323 A3 | 9/2007 |
| WO | WO 08/017051 A2 | 2/2008 |
| WO | WO 09/063423 | 5/2009 |
| WO | WO 09/094646 | 7/2009 |
| WO | WO 10/057315 | 5/2010 |
| WO | WO 10/096419 A2 | 8/2010 |
| WO | WO 11/014687 A2 | 2/2011 |
| WO | WO 12/169990 | 12/2012 |
| WO | WO 13/116240 | 8/2013 |
| WO | WO 18/080844 | 5/2018 |

OTHER PUBLICATIONS

U.S. Appl. No. 15/041,868, filed Feb. 11, 2016, Fuchs et al.
U.S. Appl. No. 15/068,323 including its ongoing prosecution history, including without limitation Office Actions, Amendments, Remarks, and any other potentially relevant documents, filed Mar. 11, 2016, Razzaque et al.
U.S. Appl. No. 15/182,346, filed Jun. 14, 2016, Razzaque et al.
U.S. Appl. No. 15/199,630, filed Jun. 30, 2016, Razzaque et al.
U.S. Appl. No. 15/799,639, filed Oct. 31, 2017, Green et al.
U.S. Appl. No. 15/882,709, filed Jan. 29, 2018, State et al.
U.S. Appl. No. 15/995,059, filed Apr. 17, 2018, Kohli et al.
U.S. Appl. No. 16/052,289, filed Aug. 1, 2018, Kohli et al.
U.S. Appl. No. 16/178,002, filed Nov. 1, 2018, Heaney et al.
U.S. Appl. No. 16/177,894, filed Nov. 1, 2018, Keller et al.
U.S. Appl. No. 16/209,021, filed Dec. 4, 2018, Razzaque et al.
U.S. Appl. No. 16/255,629, filed Jan. 23, 2019, Kohli.
U.S. Appl. No. 16/920,560 including its ongoing prosecution history, including without limitation Office Actions, Amendments, Remarks, and any other potentially relevant documents, filed Jul. 1, 2020, Keller et al.
U.S. Appl. No. 17/071,256 including its ongoing prosecution history, including without limitation Office Actions, Amendments, Remarks, and any other potentially relevant documents, filed Oct. 15, 2020, Heaney et al.
U.S. Appl. No. 17/071,459 including its ongoing prosecution history, including without limitation Office Actions, Amendments, Remarks, and any other potentially relevant documents, filed Oct. 15, 2020, State et al.
"3D Laparoscope Technology," http://www.inneroptic.com/tech_3DL.htm, copyright 2007 InnerOptic Technology, Inc. printed Sep. 19, 2007, 2 pages.
"AIM 3D Needle Placement Software from InnerOptic", Medgadget, Sep. 21, 2012.
AIM Section 5: 510k Summary, submitted by InnerOptic Technology, Inc., in 5 pages, submission date May 17, 2012.
"Cancer Facts & Figures 2004," www.cancer.org/downloads/STT/CAFF_finalPWSecured.pdf, copyright 2004 American Cancer Society, Inc., printed Sep. 19, 2007, 60 pages.
Cancer Prevention & Early Detection Facts & Figures 2004; National Center for Tobacco-Free Kids; 2004; American Cancer Society; USA.
"David Laserscanner <-Latest News <-Institute for Robotics and Process Control <-Te . . . ," http://www/rob.cs.tu-bs.de/en/news/david, printed Sep. 19, 2007, 1 page.
"InnerOptic's AIM System Receives DA 510(K) Clearance", InnerOptic Technology, Inc., Sep. 18, 2012.
"Laser scanned 3d model Final" video, still image of video attached, http://www.youtube.com/watch?v+DaLglgmoUf8, copyright 2007 YouTube, LLC, printed Sep. 19, 2007, 2 pages.

(56) References Cited

OTHER PUBLICATIONS

"Olympus Endoscopic Ultrasound System," www.olympusamerica. com/msg_section/download_brochures/135_b_gfum130.pdf, printed Sep. 20, 2007, 20 pages.
"Point Grey Research Inc.—Imaging Products—Triclops SDK Samples," http://www.ptgrey.com/products/triclopsSDK/samples. asp, copyright 2007 Point Grey Research Inc., printed Sep. 19, 2007, 1 page.
"Robbins, Mike—Computer Vision Research—Stereo Depth Perception," http://www.compumike.com/vision/stereodepth.php, copyright 2007 Michael F. Robbins, printed Sep. 19, 2007, 3 pages.
"RUE, Registered Ultrasound-Endoscope," copyright 2007 InnerOptic Technology, Inc., 2 pages.
Advertisement, "Inspeck 3DC 3D Capturor," Inspeck 3DC 3D Capturor (www.inspeck.com), 1998.
Advertisement, "Virtual 3D High Speed Non-Contact Surface Perception," Virtual 3-D Technologies Corporation (www.virtual3dtech. com)., Dec. 21, 1998.
Advertisements, "Virtuoso," Visual Interface, Inc. (www.visint. com), Dec. 21, 1998.
Akka, "Automatic Software Control of Display Parameters for Stereoscopic Graphics Images," SPIE vol. 1669: Stereoscopic Displays and Applications III, pp. 31-38 (1992).
Ali et al., "Near Infrared Spectroscopy and Imaging to Probe Differences in Water Content in Normal and Cancer Human Prostate Tissues," Technology in Cancer Research & Treatment; Oct. 2004; 3(5):491-497; Adenine Press.
Aylward et al., Analysis of the Parameter Space of a Metric for Registering 3D Vascular Images, in W. Niessen and M. Viergever (Eds.): MICCAI 2001, LNCS 2208, pp. 932-939, 2001.
Aylward et al., Registration and Analysis of Vascular Images, International Journal of Computer Vision 55(2/3), 123-138, 2003.
Aylward, et al., Intra-Operative 3D Ultrasound Augmentation, Proceedings of the IEEE International Symposium on Biomedical Imaging, Washington, Jul. 2002.
Azuma et al., "Improving Static and Dynamic Registration in an Optical See-Through HMD," Paper Presented at SIGGRAPH '94 Annual Conference in Orlando, FL, 17 pages (1994).
Azuma, "A Survey of Augmented Reality," Presence: Teleoperators and Virtual Environments 6, 4:1-48 (Aug. 1997).
Badler et al., "Simulating Humans: Computer Graphics, Animation, and Control," Oxford University Press (1993).
Bajura, Michael et al., "Merging Virtual Objects with the Real World: Seeing Ultrasound Imagery within the Patient," Computer Graphics, Proceedings of SIGGRAPH 1992, vol. 26(2), pp. 203-210, available from www.cs.unc.edu/~fuchs/publications/ MergVirtObjs92.pdf, printed Sep. 20, 2007, 8 pages.
Benavides et al., "Multispectral digital colposcopy for in vivo detection of cervical cancer," Optics Express; May 19, 2003; 11(10) Optical Society of America; USA.
Beraldin, J.A. et al., "Optimized Position Sensors for Flying-Spot Active Triangulation Systems," Proceedings of the Fourth International Conference on a 3-D Digital Imaging and Modeling (3DIM), Banff, Alberta, Canada, Oct. 6-10, 2003, pp. 334-341, NRC 47083, copyright 2003 National Research Council of Canada, http://iit-iti. nrc-cnrc.gc.ca/iit-publications-iti/docs/NRC-47083.pdf, printed Sep. 19, 2007, 9 pages.
Billinghurst, M. et al., Research Directions in Handheld AR; Int. J. of Virtual Reality 5(2),51-58 (2006).
Blais, F., "Review of 20 Years of Range Sensor Development," Journal of Electronic Imaging, 13(1):231-240, Jan. 2004, NRC 46531, copyright 2004 National Research Council of Canada, http://iit-iti.nrc-cnrc.gc.ca/iit-publications-iti/docs/NRC-46531.pdf, printed Sep. 19, 2007, 14 pages.
Bouguet, Jean-Yves, "Camera Calibration Toolbox for Matlab," www.vision.caltech.edu/bouguetj/calib_doc, printed Sep. 20, 2007, 5 pages.
Buxton et al.; "Colposcopically directed punch biopsy: a potentially misleading investigation," British Journal of Obstetrics and Gynecology; Dec. 1991; 98:1273-1276.

Caines, Judy S. et al. Stereotaxic Needle Core Biopsy of Breast Lesions Using a Regular Mammographic Table with an Adaptable Stereotaxic Device, American Journal of Roentgenology, vol. 163, No. 2, Aug. 1994, pp. 317-321. Downloaded from www.ajrorline. org on Jul. 10, 2013.
Cantor et al., "Cost-Effectiveness Analysis of Diagnosis and Management of Cervical Squamous Intraepithelial Lesions," Diagnostic Strategies for SILs; Feb. 1998; 91(2):270-277.
Catalano et al. "Multiphase helical CT findings after percutaneous ablation procedures for hepatocellular carcinoma." Abdom. Imaging, 25(6),2000, pp. 607-614.
Chiriboga et al., "Infrared Spectroscopy of Human Tissue. IV. Detection of Dysplastic and Neoplastic Changes of Human Cervical Tissue Via Infrared Microscopy," Cellular and Molecular Biology; 1998; 44(1): 219-229.
Crawford, David E. et al., "Computer Modeling of Prostate Biopsy: Tumor Size and Location—Not Clinical Significance—Determine Cancer Detection," Journal of Urology, Apr. 1998, vol. 159(4), pp. 1260-1264, 5 pages.
Deering, Michael "High Resolution Virtual Reality." Proceedings of SIGGRAPH '92, Computer Graphics, 26(2), 1992, pp. 195-202.
Depiero et al., "3-D Computer Vision Using Structured Light: Design, Calibration and Implementation Issues," The University of Tennessee, pp. 1-46, (1996).
Dodd, G.D. et al. "Minimally invasive treatment of malignant hepatic tumors: at the threshold of a major breakthrough." Radiographies 20(1),2000, pp. 9-27.
Drascic et al., "Perceptual Issues in Augmented Reality," SPIE vol. 2653: Stereoscopic Displays and Virtual Reality Systems III, pp. 123-134 (Feb. 1996).
Dumoulin, C.L. et al, Real-Time Position Monitoring of Invasive Devices Using Magnetic Resonance, Magnetic Resonance in Medicine, vol. 29, Issue 3, Mar. 1993, pp. 411-415.
Edwards et al., Video See-Through Design for Merging of Real and Virtual Environments, VRAIS '93, pp. 1-11 (1993).
Fahey et al., "Meta-analysis of Pap Test Accuracy; American Journal of Epidemiology," 1995 141(7):680-689; The John Hopkins University School of Hvqiene and Public Health; USA.
Foxlin et al., "An Inertial Head-Orientation Tracker with Automatic Drift Compensation for Use with HMD's," Proceedings of the 1994 Virtual Reality Software and Technology Conference, Aug. 23-26, 1994, Singapore, pp. 159-173 (1994).
Fronheiser et al., Real-Time 3D Color Doppler for Guidance of Vibrating Interventional Devices, IEEE Ultrasonics Symposium, pp. 149-152 (2004).
Fuchs, Henry et al. "Augmented Reality Visualization for Laparoscopic Surgery," Proceedings of Medical Image Computing and Computer-Assisted Intervention (MICCAI) 1998, pp. 934-943, available from www.cs.unc.edu/~fuchs/publications /AugRealVis_ LaparoSurg98.pdf, printed Sep. 20, 2007, 10 pages.
Fuchs, et al.: "Optimizing a Head-Tracked Stereo Display System to Guide Hepatic Tumor Ablation," Departments of Computer Sciences and Radiology, and School of Medicine, University of North Carolina at Chapel Hill; InnerOptic Technology, Inc. 2008.
Fuchs, et al.: "Virtual Environments Technology To Aid Needle Biopsies of the Breast," Health Care in the Information Age, Ch. 6, pp. 60-61, Presented in San Diego, Jan. 17-20, 1996, published by IOS Press and Ohmsha Feb. 1996.
Fuhrmann A. et al., Comprehensive calibration and registration procedures for augmented reality; Proc. Eurographics Workshop on Virtual Environments 2001,219-228 (2001).
Garrett, William F. et al., "Real-Time Incremental Visualization of Dynamic Ultrasound Volumes Using Parallel BSP Trees, "Proceedings of IEEE Visualization 1996, pp. 235-240, available from www.cs.unc.edu/~andrei/pubs/1996_VIS_dualBSP_Mac.pdf, printed Sep. 20, 2007, 7 pages.
Georgakoudi et al., "Trimodal spectroscopy for the detection and characterization of cervical precancers in vivo," American Journal of Obstetrics and Gynecology; Mar. 2002; 186(3):374-382; USA.
StereoMirror Technology Webpage, http://www.planar.com/products/ flatpanel_monitors/stereoscopic/(Printed Dec. 29, 2011).
Herline et al., Surface Registration for Use in Interactive, Image-Guided Liver Surgery, Computer Aided Surgery 5:11-17 (2000).

(56) References Cited

OTHER PUBLICATIONS

Holloway, R.; Registration Error Analysis for Augmented Reality; Presence: Teleoperators and Virtual Environments 6(4), 413-432 (1997).
Hornung et al., "Quantitative near-infrared spectroscopy of cervical dysplasia in vivo," Human Reproduction; 1999; 14(11):2908-2916; European Society of Human Reproduction and Embryology.
Howard, M.D., et al.: "An Electronic Device for Needle Placement during Sonographically Guided Percutaneous Intervention", Radiology 2001; 218:905-911.
InnerAim Brochure; 3D Visualization Software for Simpler, Safer, more Precise Aiming, Published no earlier than Apr. 1, 2010.
InVision System Brochure; A "GPS" for Real-Time 3D Needle Visualization & Guidance, Published no earlier than Mar. 1, 2008.
InVision User Manual; Professional Instructions for Use, Published no earlier than Dec. 1, 2008.
Jacobs, Marco C. et al., "Managing Latency in Complex Augmented Reality Systems," ACM SIGGRAPH Proceedings of the Symposium of Interactive 3D Graphics 1997, pp. 49-54, available from www.cs.unc.edu/~us/Latency//ManagingRelativeLatency.html, printed Sep. 20, 2007, 12 pages.
Jolesz, Ferenc A, M.D., et al. MRI-Guided Laser-Induced Interstitial Thermotherapy: Basic Principles, SPIE Institute on Laser-Induced Interstitial Thermotherapy (L1TT), Jun. 22-23, 1995, Berlin, Germany.
Kadi, A Majeed, et al., Design and Simulation of an Articulated Surgical Arm for Guiding Sterotactic Neurosurgery, SPIE vol. 1708 Applications of Artificial Intelligence X: Machine Vision and Robotics (1992). Downloaded from: http://proceedings.spiedigitallibrary.org/ on Jul. 11, 2013.
Kanbara et al., "A Stereoscopic Video See-through Augmented Reality System Based on Real-time Vision-Based Registration," Nara Institute of Science and Technology, pp. 1-8 (2000).
Kato, Amami, et al., A frameless, armless navigational system for computer-assisted neurosurgery, Journal of Neurosurgery, vol. 74, No. 5, May 1991, pp. 845-849.
Keller et al., "What is it in Head Mounted Displays (MDs) that really make them all so terrible?," pp. 1-8 (1998).
Lass, Amir, "Assessment of Ovarian Reserve," Human Reproduction, 2004, vol. 19(3), pp. 467-469, available from http://humrep.oxfordjournals.orgcgi/reprint/19/3/467, printed Sep. 20, 2007, 3 pages.
Lee, et al., "Modeling Real Objects Using Video See-Through Augmented Reality," Proceedings of the Second International Symposium on Mixed Reality, ISMR 2001, pp. 19-26 (Mar. 14-15, 2001).
Lee et al., "Modeling Real Objects Using Video See-Through Augmented Reality," Presence, 11(2):144-157 (Apr. 2002).
Leven et al., DaVinci Canvas: A Telerobotic Surgical System with Integrated, Robot-Assisted, Laparoscopic Ultrasound Capability, in J. Duncan and G. Gerig (Eds.): MICCAI 2005, LNCS 3749, pp. 811-818, 2005.
Levy, et al., An Internet-Connected, Patient Specific, Deformable Brain Atlas Integrated into a Surgical Navigation System, Journal of Digital Imaging, vol. 10, No. 3. Suppl. 1 Aug. 1997: pp. 231-237.
Lindeman, A Low-Cost, Low-latency Approach to Dynamic Immersion in Occlusive Head-Mounted Displays, University of Canterbury, WPI,—Poster from IEEE VR 2016, Mar. 19-23, 2016.
Lipton, "Foundations of the Steroscopic Cinema A Study in Depth," Van Nostrad Reinhold Company, pp. 1-319 (1982).
Livingston, Mark A. et al., "Magnetic Tracker Calibration for Improved Augmented Reality Registration," Presence: Teleoperators and Virtual Environments, 1997, vol. 6(5), pp. 532-546, available from www.cs.unc.edu/~andrei/pubs/1997_Presence_calibr.pdf, printed Sep. 20, 2007, 14 pages.
Matsunaga et al., "The Effect of the Ratio Difference of Overlapped Areas of Stereoscopic Images on each Eye in a Teleoperalion," Stereoscopic Displays and Virtual Reality Systems VII, Proceedings of SPIE, 3957:236-243 (2000).

Meehan, Michael et al., "Effect of Latency on Presence in Stressful Virtual Environment," Proceedings of IEEE Virtual Reality 2003, pp. 141-148, available from http://www.cs.unc.edu/~eve/pubs.html, printed Sep. 20, 2007, 8 pages.
Milgram et al., "Adaptation Effects in Stereo due to Online Changes in Camera Configuration," SPIE vol. 1669-13, Stereoscopic Displays and Applications III, 17 pages (1992).
Mitchell et al., "Colposcopy for the Diagnosis of Squamous Intraepithelial lesions: A metaanalysis," Obstetrics and Gynecology; Apr. 1998; 91(4):626-631.
Nakamoto et al., 3D Ultrasound System Using a Magneto-optic Hybrid Tracker for Augmented Reality Visualization in Laparoscopic Liver Surgery, in T. Dohi and R. Kikinis (Eds.): MICCAI 2002, LNCS 2489, pp. 148-155, 2002.
Nordstrom et al., "Identification of Cervical Intraepithelial Neoplasia (CIN) Using UV-Excited Fluorescence and Diffuse-Reflectance Tissue Spectroscopy," Lasers in Surgery and Medicine; 2001; 29; pp. 118-127; Wiley-Liss, Inc.
Ohbuchi et al. "An Incremental Volume Rendering Algorithm for Interactive 3D Ultrasound Imaging", UNC-CH Computer Science Technical Report TR91-003, (1991).
Ohbuchi et al., "Incremental Volume Reconstruction and Rendering for 3D Ultrasound Imaging," Visualization in Biomedical Computing, SPIE Proceedings, pp. 312-323, (Oct. 13, 1992).
Ohbuchi, "Incremental Acquisition and Visualization of 3D Ultrasound Images," Ph.D. Dissertation, UNC-CH Computer Science Technical Report TR95--023, (1993).
International Search Report and Written Opinion, re PCT Application No. PCT/US2017/057042, dated Feb. 28, 2018.
PCT International Preliminary Report on Patentability, re PCT Application No. PCT/US2017/057042, dated Apr. 30, 2019.
Ohnesorge, Lauren K., "InnerOptic technology wins FDA approval", Triangle Business Journal, Sep. 19, 2012.
Pogue, Brian W. et al., "Analysis of acetic acid-induced whitening of high-grade squamous intraepitheliallesions," Journal of Biomedical Optics; Oct. 2001; 6(4):397-403.
Press Release: Pathfinder and InnerOptic Announce Technology Integration to Enhance Visualization and Outcomes in Liver Surgery, Published Mar. 6, 2013.
Raij, A.B., et al., Comparing Interpersonal Interactions with a Virtual Human to Those with a Real Human; IEEE Transactions on Visualization and Computer Graphics 13(3), 443-457 (2007).
Raz et al., Real-Time Magnetic Resonance Imaging-Guided Focal Laser Therapy in Patients with Low-Risk Prostate Cancer, European Urology 58, pp. 173-177. Mar. 12, 2010.
Robinett et al., "A Computational Model for the Stereoscopic Optics of a Head-Mounted Display," SPIE vol. 1457, Stereoscopic Displays and Applications II, pp. 140-160 (1991).
Rolland et al., Towards Quantifying Depth and Size Perception in Virtual Environments, Presence: Teleoperators and Virtual Environments, Winter 1995, vol. 4, Issue 1, pp. 1-21 and 24-49.
Rosenthal, Michael et al., "Augmented Reality Guidance for Needle Biopsies: An Initial Randomized, Controlled Trial in Phantoms," Proceedings of Medical Image Analysis, Sep. 2002, vol. 6(3), pp. 313-320, available from www.cs.unc.edu/~fuchs/publications/AugRealGuida_NeedleBiop02.pdf, printed Sep. 20, 2007, 8 pages.
Rosenthal, Michael et al., "Augmented Reality Guidance for Needle Biopsies: A Randomized, Controlled Trial in Phantoms," Proceedings of MICCAI 2001, eds. W. Niessen and M. Viergever, Lecture Notes in Computer Science, 2001, vol. 2208, pp. 240-248, available from www.cs.unc.edu/~us/AugmentedRealityAssistance.pdf, printed Sep. 20, 2007, 9 pages.
Screenshots from video produced by the University of North Carolina, produced circa 1992.
"Sony Introduces Head-Mounted Display for Endoscopic Surgery" (Jul. 23, 2013), retrieved Sep. 27, 2016, 5 pages, available at http://www.medgaget.com/2013/07/sony-introduces-head-mounted-display-for-endoscopic-surgery.html.
"Sony Introduces 'head-mount image processing unit' for endoscopic image display" (Jul. 23, 2013), retrieved Sep. 27, 2016, 14 pages, available at http://www.sony.net/SonyInfo/News/Press/201307/13-085E/index.html.

(56) References Cited

OTHER PUBLICATIONS

Splechtna et al, Comprehensive calibration and registration procedures for augmented reality; Proc. Eurographics Workshop on Virtual Environments 2001, 219-228 (2001).

State et al., "Case Study: Observing a Volume Rendered Fetus within a Pregnant Patient," Proceedings of IEEE Visualization 1994, pp. 364-368, available from www.cs.unc.edu/~fuchs/publications/cs-ObservVolRendFetus94.pdf, printed Sep. 20, 2007, 5 pages.

State et al., "Interactive Volume Visualization on a Heterogeneous Message-Passing Multicomputer," Proceedings of 1995 Symposium on Interactive 3D Graphics, 1995, pp. 69-74, 208, available from www.cs.unc.edu/~andrei/pubs/1995_I3D_vol2_Mac.pdf, printed Sep. 20, 2007.

State et al., "Simulation-Based Design and Rapid Prototyping of a Parallax-Free, Orthoscopic Video See-Through Head-Mounted Display," Proceedings of International Symposium on Mixed and Augmented Reality (ISMAR) 2005, available from www.cs.unc.edu/~andrei/pubs/2005_ISMAR_VSTHMD_design.pdf, printed Sep. 20, 2007, 4 pages.

State et al., "Stereo Imagery from the UNC Augmented Reality System for Breast Biopsy Guidance" Proc. Medicine Meets Virtual Reality (MMVR) 2003 (Newport Beach, CA, Jan. 22-25, 2003).

State et al., "Superior Augmented Reality Registration by Integrating Landmark Tracking and Magnetic Tracking," ACM SIGGRAPH Computer Graphics, Proceedings of SIGGRAPH 1996, 10 pages (Aug. 1996).

State et al., "Technologies for Augmented Reality Systems: Realizing Ultrasound-Guided Needle Biopsies," Proc. SIGGRAPH 96 (New Orleans, LA, Aug. 4-9, 1996). In Computer Graphics Proceedings, Annual Conference Series, 1996, ACM SIGGRAPH, pp. 439-446.

State, Andrei "Exact Eye Contact with Virtual Humans." Proc. IEEE International Workshop on Human Computer Interaction 2007 (Rio de Janeiro, Brazil, Oct. 20, 2007), pp. 138-145.

State, et al.: Contextually Enhanced 3D Visualization for Multi-Born Tumor Ablation Guidance, Departments of Computer Science and Radiology, and School of Medicine, University of North Carolina at Chapel Hill; InnerOptic Technology, Inc. 2008, Chapel Hill, NC, pp. 70-77.

Symons et al., "What are You Looking at? Acuity for Triadic Eye Gaze," J. Gen. Psychology 131(4), pp. 451-469 (2004).

Takacs et al., "The Virtual Human Interface: A Photorealistic Digital Human," IEEE Computer Graphics and Applications 23(5), pp. 38-45 (2003).

Takagi et al., "Development of a Stereo Video See-through HMD for AR Systems," IEEE, pp. 68-77 (2000).

Takayama et al., "Virtual Human with Regard to Physical Contact and Eye Contact," Entertaining Computing 2005, LNCS, vol. 3711, pp. 268-278 (2005).

Ultraguide 1000 System, Ultraguide, www.ultraguideinc.com, 1998.

Van Staveren et al., "Light Scattering in Intralipid—10% in the wavelength range of 400-1100 nm," Applied Optics; Nov. 1991; 30(31):4507-4514.

Viola et al., "Alignment by Maximization of Mutual Information," International Journal of Computer Vision, vol. 24, No. 2, pp. 137-154 (1997).

Viola, Paul A., Alignment by Maximization of Mutual Information, Ph.D. Dissertation, MIT—Artificial Intelligence Laboratory Technical Report No. 1548 (Jun. 1995), 156 pages.

Ware et al., "Dynamic Adjustment of Stereo Display Parameters," IEEE Transactions on Systems, Many and Cybernetics, 28(1):1-19 (1998).

Watson et al., "Using Texture Maps to Correct for Optical Distortion in Head-Mounted Displays," Proceedings of the Virtual Reality Annual Symposium '95, IEEE, pp. 1-7 (1995).

Welch, Hybrid Self-Tracker: An Inertial/Optical Hybrid Three-Dimensional Tracking System, University of North Carolina Chapel Hill Department of Computer Science, TR 95-048 (1995).

Yinghui et al., Real-Time Deformation Using Modal Analysis on Graphics Hardware, GRAPHITE 2006, Kuala Lumpur, Malaysia, Nov. 29-Dec. 2, 2006.

Zitnick et al., "Multi-Base Stereo Using Surface Extraction," Visual Interface Inc., (Nov. 24, 1996).

\* cited by examiner

MEDICAL DEVICE NAVIGATION USING A VIRTUAL 3D SPACE

CROSS-REFERENCE TO RELATED APPLICATIONS

The present application is a continuation of U.S. patent application Ser. No. 16/366,537, filed on Mar. 27, 2019 which is a continuation of U.S. patent application Ser. No. 15/415,398, filed on Jan. 25, 2017, which claims priority benefit to U.S. Provisional Application No. 62/413,925, each of which is hereby incorporated herein by reference in its entirety. Any and all applications for which a foreign or domestic priority claim is identified in the Application Data Sheet as filed with the present application are incorporated by reference under 37 CFR 1.57 and made a part of this specification.

BACKGROUND

Various systems are available to aid a healthcare provider to guide a medical device in a patient or to provide a user viewing an object with additional information. The systems can provide image guidance cues to aid the healthcare provider or user and can also provide additional information for the user's benefit.

DETAILED DESCRIPTION

Figure 1A:
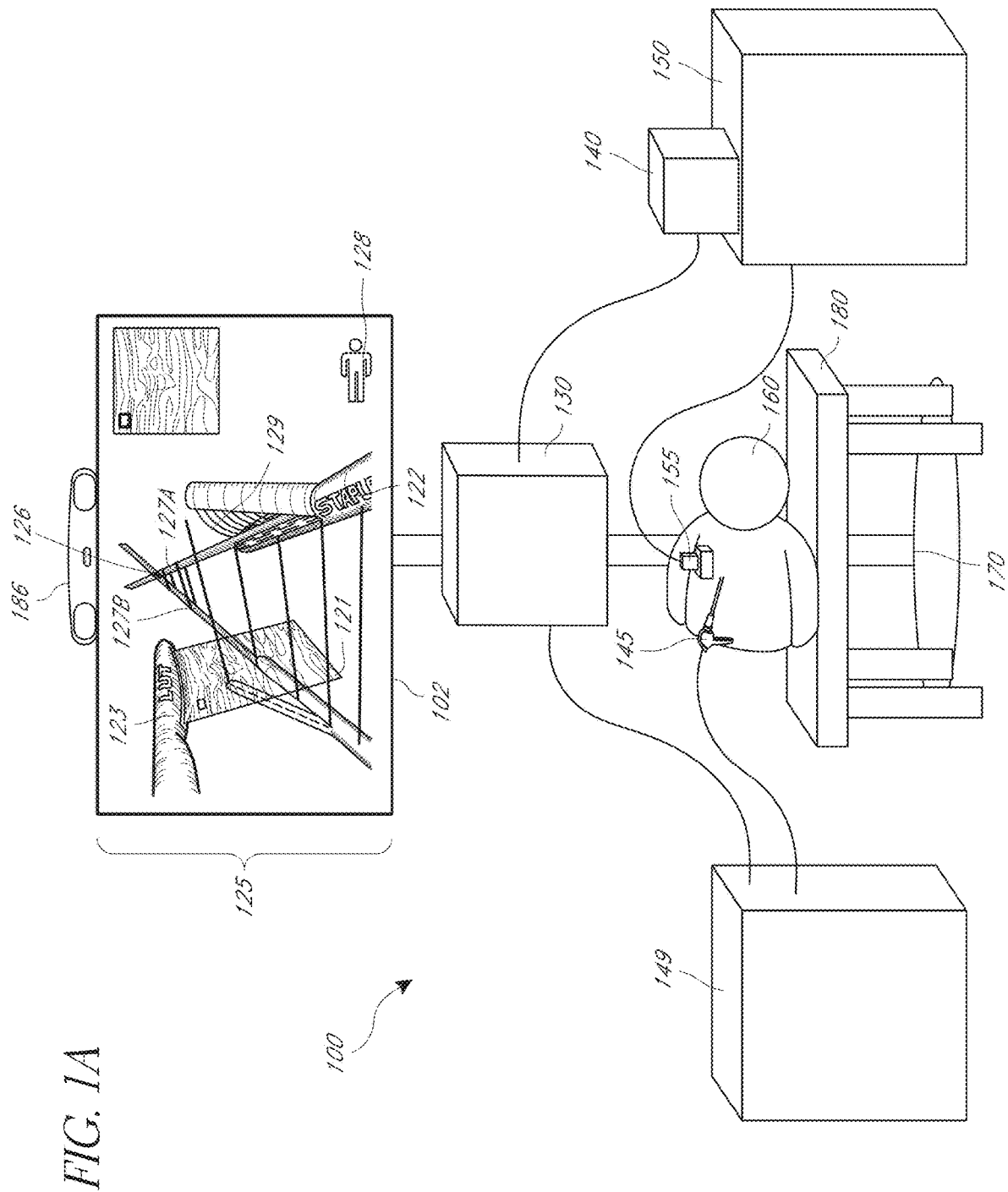
FIG. 1A is a diagram illustrating an embodiment of an environment for image-guided medical procedures.

Implementations disclosed herein provide systems, methods, and apparatus for displaying medical images, such as, but not limited to ultrasound, CT, and/or MRI images, facilitating medical device insertion into tissue by an operator. Certain embodiments pertain to a free-hand medical device guidance system. The system can provide the healthcare provider manual control over the medical device, while making the spatial relationships between the target, medical device and medical image (also referred to as an image slice or rendered medical image), or image area corresponding to the medical image (also referred to as an image slice area or scan area), more intuitive via a visual display. Using this visual feedback, the operator can adjust the medical device's position, orientation, or trajectory. Certain of the contemplated embodiments can be used in conjunction with systems described in greater detail in U.S. patent application Ser. No. 13/014,587, filed Jan. 26, 2011, entitled SYSTEMS, METHODS, APPARATUSES, AND COMPUTER-READABLE MEDIA FOR IMAGE MANAGEMENT IN IMAGE-GUIDED MEDICAL PROCEDURES and U.S. patent application Ser. No. 13/753,274, filed Jan. 29, 2013, entitled MULTIPLE MEDICAL DEVICE GUIDANCE (the '274 Application), U.S. patent application Ser. No. 14/212,933, filed Mar. 14, 2014, entitled MEDICAL DEVICE GUIDANCE, U.S. patent application Ser. No. 15/199,630, filed Jun. 30, 2016, entitled LOUPE DISPLAY, and U.S. patent application Ser. No. 14/872,930, filed Oct. 1, 2015, entitled AFFECTED REGION DISPLAY (the '930 Application), each of which is hereby incorporated by reference in its entirety.

Medical interventions typically involve using an instrument to resect, cauterize, staple, seal, or otherwise manipulate soft tissue and organs. A physician must take great care to minimize blood loss and minimize damage to ancillary tissue while performing these tissue-damaging interventions. This is even more difficult with minimally-invasive surgeries, such as laparoscopic, endoscopic, and robotic surgeries. A physician may use ultrasound to image the internal structures of an organ before stapling, transecting, resecting, sealing, or grasping tissue, helping her avoid critical structures such as blood vessels. However, even with ultrasound imaging, there is a significant possibility of inadvertent damage to surrounding tissue and blood vessels during these procedures. This is because it is not obvious in the externally displayed medical image where a given internal structure is located relative to the medical device.

The system can aid the healthcare provider in guiding one or more medical devices through or around tissue of the patient and/or placing the medical devices. The system can be used to aid in stapling, transecting, resecting, sealing, and/or grasping tissue. Additionally, the system can be used for treatment of tumors, fibroids, cysts, damaged blood vessels, or other damages internal structures of a patient. The system can be used during open surgery, laparoscopic surgery, endoscopic procedures, robotic surgeries, biopsies, and/or interventional radiology procedures.

The system can be used in conjunction with live intraoperative ultrasound (U/S), pre-operative CT, or any cross-sectional medical imaging modality (e.g. MRI, OCT, etc.). In addition, the system can use a variety of techniques to determine the position and/or orientation of one or more medical devices. For example, the system can use the NDI Aurora magnetic system, NDI Polaris optical system, etc. In some embodiments, a position sensor can be embedded inside, or affixed to each medical device, at the tip, along the shaft, and/or on the handle. Sensors can be built into the medical devices or attached after manufacturing, as described in greater detail in U.S. application Ser. No. 14/212,184, filed Mar. 14, 2014, entitled SENSOR MOUNT, incorporated herein in its entirety.

Each medical device can be associated with one or more sensors, which can continually, or repeatedly, report position and/or orientation, or a single sensor can be used for all the medical devices. In some embodiments where one sensor is used, the healthcare provider can attach the sensor to the particular medical device that she is intentionally repositioning, and then, once she has placed that medical device, she can remove the sensor and attach it to the next medical device she is repositioning. In some embodiments, the medical devices can be manipulated by the healthcare provider. In certain embodiments, the system can be used with a robotic manipulator, where the robot controls the medical devices. In some embodiments, visually-detectable fiducials can be used to determine position and/or orientation for one or more of the medical devices.

In some embodiments, the handles of medical devices can have push-button switches, to allow the user to select a medical device, indicate a tissue target, etc. The handle can also have an indicator light to indicate to the users which medical device is selected. Finally, the handle can have an encoder to detect how much length of electrode has been exposed by the user, and report this information to the guidance system and therapeutic generator.

Image Guidance Systems

FIG. 1A is a diagram illustrating an embodiment of a system for image management in image-guided medical procedures. In some embodiments, the position sensing unit 140 can track medical devices within a tracking area and provide data to the image guidance unit 130. The medical devices can include invasive medical devices, such as, but not limited to, graspers, staplers, vessel sealers, electrocautery devices, resecting devices, transecting devices, scalpels, biopsy needles, ablation needles, surgical needles, nerve-block needles, or other needles, catheters, stents, laparoscopes or laparoscopic cameras, ultrasound transducers, or other instruments that enter a part of the body, and non-invasive medical devices that do not enter the body, such as, but not limited to, ultrasound transducers, probes, or other external imaging devices, etc. The medical devices can also include medical imaging devices that provide or aid in the selection of medical images for display. In some embodiments, the medical imaging device can be any device that is used to select a particular medical image for display. The medical imaging devices can include invasive medical devices, such as laparoscopic cameras, and non-invasive medical devices, such as external ultrasound transducers.

Although only two medical devices 145 and 155 are shown in FIG. 1, it will be understood that additional medical devices can be tracked and associated data can be provided to the image guidance unit 130. The image guidance unit 130 can process or combine the data and show image guidance data on display 120. This image guidance data can be used by a healthcare provider to guide a procedure and improve care. There are numerous other possible embodiments of system 100. For example, many of the depicted components can be joined together to form a single component and can be implemented in a single computer or machine. Further, additional position sensing units can be used in conjunction with position sensing unit 140 to track all relevant medical devices 145 and 155, as discussed in more detail below. Additional imaging units 150 can be included, and combined imaging data from the multiple imaging units 150 can be processed by image guidance unit 130 and shown on display unit 120. Additionally, two or more surgical systems 149 can also be included.

Information about and from multiple surgical systems 149 and attached medical devices 145 (and additional medical devices not shown) can be processed by image guidance unit 130 and shown on display 120. These and other possible embodiments are discussed in more detail below. It will be understood that any combination of the display objects (such as, but not limited to medical display objects (e.g., virtual medical device, medical image, ghost display objects, etc.) and/or image guidance cues (e.g., trajectory indicators, intersection indicators, plane indicators, ghost display objects, etc.)) described herein can be displayed concurrently, or simultaneously. Further, reference to displaying objects "concurrently" and/or "simultaneously" is to be interpreted broadly and may refer to displaying objects in such a way that to a human observer the objects are visible at the same time.

Imaging unit 150 can be coupled to image guidance unit 130. In some embodiments, imaging unit 150 can be coupled to a second display unit (not shown). The second display unit can display imaging data from imaging unit 150. The imaging data displayed on display unit 120 and displayed on second display unit can be the same or different. In some embodiments, the imaging unit 150 is an ultrasound machine, the movable imaging device 155 is an ultrasound transducer or ultrasound probe, and the second display unit is a display associated with the ultrasound machine 150 that displays the medical images from the ultrasound machine 150. In some embodiments, a movable imaging unit 155 can be connected to image guidance unit 130. The movable imaging unit 155 can be useful for allowing a user to indicate what portions of a first set of imaging data are to be displayed. For example, the movable imaging unit 155 can be an ultrasound transducer 155, a stapler or other medical device, for example, and can be used by a user to indicate what portions of imaging data, such as a pre-operative CT scan, to show on a display unit 120 as image 125. Further, in some embodiments, there can be a third set of pre-operative imaging data that can be displayed with the first set of imaging data.

In some embodiments, system 100 comprises a display unit 120 and a position sensing unit 140 communicatively coupled to image guidance unit 130. In some embodiments, position sensing unit 140, display unit 120, and image guidance unit 130 are coupled to the stand 170. Image guidance unit 130 can be used to produce images 125 that are displayed on display unit 120. The images 125 produced on display unit 120 by the image guidance unit 130 can be determined based on ultrasound or other visual images from the first medical device 145 and second medical device 155. In the illustrated embodiment, the images 125 include a 2D viewing area and a 3D viewing area. In the 2D viewing area, some or all of the display objects can be displayed as 2D objects. For instance, the 2D viewing area can include a 2D view of each of an ultrasound slice, a virtual medical device corresponding to the first medical device, a virtual imaging device corresponding to the second medical device, intersection indicator, trajectory indicators and/or other image guidance cues. It will be understood that some or all of the display objects in the 2D viewing area can be displayed as 3D objects. In the illustrated embodiment, the 3D viewing area includes perspective views of each of the medical image 121, the virtual medical device 122, a displayed affected region 129, the virtual imaging device 123, intersection indicator 126, trajectory and other image guidance cues 127A, 127B (generically referred as image guidance cues 127 and/or trajectory indicators 127), and a patient orientation indicator 128. It will be understood that any combination of the aforementioned display objects can be displayed in the 2D view and/or 3D view as desired.

As a non-limiting example, if the first medical device 145 is a stapler 145 having a joint member and two limb members coupled to the joint member at different angles and the second medical device 155 is an ultrasound probe 155, then images 125 produced on display 120 can include the images, or video, from the ultrasound probe 155 (e.g., medical image 121) combined with other medical display objects and image guidance cues, such as display object trajectories (e.g., trajectory indicators 127) or affected region 129 (e.g., trajectory of area corresponding to a volume located between the first limb member and the second limb member), determined based on the emplacement of the stapler 145. If the first medical device 145 is an ultrasound probe 145 and the second medical device 155 is a laparoscopic camera 155, then images 125 produced on display 120 can include the video from the laparoscopic camera 155 combined with ultrasound data superimposed on the laparoscopic image. More medical devices can be added to the system. For example, the system can include a stapler, ultrasound probe, ablation needle, laparoscopic camera, scalpel, grasper, vessel sealer, electrocauterizer, resecting device, transecting device and/or any other surgical instrument or medical device. The system can also process and/or display collected data, such as preoperative CT scans, X-Rays, MRIs, laser scanned 3D surfaces etc.

The term "emplacement" as used herein is a broad term and may refer to, without limitation, position and/or orientation or any other appropriate location information. The term "pose" as used herein is a broad term encompassing its plain and ordinary meaning and may refer to, without limitation, position and orientation or any other appropriate location information. In some embodiments, the imaging data obtained from one or both of medical devices 145 and 155 can include other modalities such as a CT scan, MRI, open-magnet MRI, optical coherence tomography ("OCT"), positron emission tomography ("PET") scans, fluoroscopy, ultrasound, or other preoperative, or intraoperative 2D or 3D anatomical imaging data. In some embodiments, medical devices 145 and 155 can also be scalpels, implantable hardware, or any other device used in surgery. Any appropriate surgical system 149 or imaging unit 150 can be attached to the corresponding medical instruments 145 and 155.

As noted above, images 125 produced can also be generated based on live, intraoperative, or real-time data obtained using the second medical device 155, which is coupled to second imaging unit 150. The term "real time" as used herein is a broad term and has its ordinary and customary meaning, including without limitation instantaneously or nearly instantaneously. The use of the term real time can also mean that actions are performed or data is obtained with the intention to be used immediately, upon the next cycle of a system or control loop, or any other appropriate meaning. Additionally, as used herein, real-time data can be data that is obtained at a frequency that would allow a healthcare provider to meaningfully interact with the data during surgery. For example, in some embodiments, real-time data can be a medical image of a patient that is updated one time per second. In some embodiments, real-time data can be ultrasound data that is updated multiple times per second.

The medical devices 145, 155 can be communicatively coupled to the position sensing unit 140 (e.g., sensors embedded or coupled to the medical devices 145, 155 can be communicatively coupled with the position sensing unit 140). The position sensing unit 140 can be part of imaging unit 150 or it can be separate. The position sensing unit 140 can be used to determine the emplacement of first medical device 145 and/or the second medical device 155. In some embodiments, the position sensing unit 140 can include a magnetic tracker and/or one or more magnetic coils can be coupled to medical devices 145 and/or 155. In some embodiments, the position sensing unit 140 can include an optical tracker and/or one or more visually-detectable fiducials can be coupled to medical devices 145 and/or 155. In some embodiments, the position sensing unit 140 can be located below the patient. In such embodiments, the position sensing unit 140 can be located on or below the table 180. For example, in embodiments where the position sensing unit 140 is a magnetic tracker, it can be mounted below the surgical table 180. Such an arrangement can be useful when the tracking volume of the position sensing unit 140 is dependent on the location of the position sensing unit 140, as with many magnetic trackers. In some embodiments, magnetic tracking coils can be mounted in or on the medical devices 145 and 155.

In some embodiments, the position sensing unit 140 can be an electromagnetic measurement system (e.g., NDI Aurora system) using sensor coils for tracking units attached to the first and/or second surgical devices 145 and 155. In some embodiments, the second position sensing unit 140 can be an optical 3D tracking system using fiducials. Such optical 3D tracking systems can include the NDI Polaris Spectra, Vicra, Certus, PhaseSpace IMPULSE, Vicon MX, InterSense IS-900, NaturalPoint OptiTrack, Polhemus FastTrak, IsoTrak, or Claron MicronTracker2. In some embodiments, the position sensing unit 140 can each be an inertial 3D tracking system comprising a compass, accelerometer, tilt sensor, and/or gyro, such as the InterSense InertiaCube or the Nintendo Wii controller. In some embodiments, the position sensing unit 140 can be attached to or affixed on the corresponding surgical device 145 and 155.

In some embodiments, the position sensing units 140, can include sensing devices such as the HiBall tracking system, a GPS device, or signal emitting device that would allow for tracking of the position and/or orientation (e.g., emplacement) of the tracking unit (also referred to as an emplacement sensor). In some embodiments, a position sensing unit 140 can be affixed to either or both of the surgical devices 145 and 155. The surgical devices 145 or 155 can be tracked by the position sensing unit 140. A room coordinate system reference, such as the display 120 can also be tracked by the position sensing unit 140 in order to determine the emplacements of the surgical devices 145 and 155 with respect to the room coordinate system. Devices 145 and 155 can also include or have coupled thereto one or more accelerometers, which can be used to estimate movement, position, and location of the devices.

In some embodiments, the position sensing unit 140 can be an Ascension Flock of Birds, Nest of Birds, driveBAY, medSAFE, trakSTAR, miniBIRD, MotionSTAR, pciBIRD, or Calypso 2D Localization System and tracking units attached to the first and/or second medical devices 145 and 155 can be magnetic tracking coils.

The term "tracking unit" (also referred to as an emplacement sensor), as used herein, is a broad term encompassing its plain and ordinary meaning and includes without limitation all types of magnetic coils or other magnetic field sensing devices for use with magnetic trackers, fiducials or other optically detectable markers for use with optical trackers, such as those discussed above and below. In some embodiments, the tracking units can be implemented using optical position sensing devices, such as the HiBall tracking system and the position sensing unit 140 can form part of the HiB all tracking system. Tracking units can also include a GPS device or signal emitting device that allows for tracking of the position and/or orientation of the tracking unit. In some embodiments, a signal emitting device might include a radio-frequency identifier (RFID). In such embodiments, the position sensing unit 140 can use the GPS coordinates of the tracking units or can, for example, triangulate the radio frequency signal being emitted by the RFID associated with tracking units. The tracking systems can also include one or more 3D mice.

Images 125 can be produced based on intraoperative or real-time data obtained using first medical device 145, which is coupled to first surgical system 149. In the illustrated embodiment of FIG. 1, the first surgical system 149 is shown as coupled to image guidance unit 130. The coupling between the first surgical system 149 and image guidance unit 130 may not be present in all embodiments. In some embodiments, the coupling between first surgical system 149 and image guidance unit 130 can be included where information about first medical device 145 available to first surgical system 149 is useful for the processing performed by image guidance unit 130. For example, in some embodiments, the first medical device 145 (for example, a stapler) includes a joint member and two limb members coupled to the joint member at different angles and the first surgical system 149 is a stapler navigation system 149. In some embodiments, it can be useful to send a signal about the angle of one or more of the jaws of instruments such as staplers, vessel sealers, and graspers to image guidance unit 130 so that image guidance unit 130 can show an affected region of tissue which is located between the two jaws. In other embodiments, the first surgical system 149 is not coupled to image guidance unit 130. Example embodiments including images and graphics that can be displayed are included below.

In some embodiments, the display unit 120 displays 3D images to a user, such as a healthcare provider. Stereoscopic 3D displays separate the imagery shown to each of the user's eyes. This can be accomplished by a stereoscopic display, a lenticular auto-stereoscopic display, or any other appropriate type of display. The display 120 can be an alternating row or alternating column display. Example alternating row displays include the Miracube G240S, as well as Zalman Trimon Monitors. Alternating column displays include devices manufactured by Sharp, as well as many "auto-stereoscopic" displays (e.g., Philips). In some embodiments, Sony Panasonic 3D passive displays and LG, Samsung, and/or Vizio 3D TVs can be used as well. Display 120 can also be a cathode ray tube. Cathode Ray Tube (CRT) based devices, can use temporal sequencing, showing imagery for the left and right eye in temporal sequential alternation. This method can also be used for projection-based devices, as well as by liquid crystal display (LCD) devices, light emitting diode (LED) devices, and/or organic LED (OLED) devices.

In certain embodiments, the display unit 120 can be a head mounted display worn by the user in order to receive 3D images from the image guidance unit 130. In such embodiments, a separate display, such as the pictured display unit 120, can be omitted. The 3D graphics can be produced using underlying data models, stored in the image guidance unit 130 and projected onto one or more 2D planes in order to create left and right eye images for a head mount, lenticular, or other 3D display. The underlying 3D model can be updated based on the relative emplacements of the various devices 145 and 155, as determined by the position sensing unit(s) 140, and/or based on new data associated with the devices 145 and 155. For example, if the second medical device 155 is an ultrasound probe, then the underlying data model can be updated to reflect the most recent medical image. If the first medical device 145 is a stapler, then the underlying model can be updated to reflect any changes related to the jaws, such as information regarding the affected region or angles of the jaws and/or transecting knife. Any appropriate 3D graphics processing can be used for rendering including processing based on OpenGL, Direct3D, Java 3D, etc. Whole, partial, or modified 3D graphics packages can also be used, such packages including 3DS Max, SolidWorks, Maya, Form Z, Cybermotion 3D, VTK, Slicer, or any others. In some embodiments, various parts of the needed rendering can occur on traditional or specialized graphics hardware. The rendering can also occur on the general CPU, on programmable hardware, on a separate processor, be distributed over multiple processors, over multiple dedicated graphics cards, or using any other appropriate combination of hardware or technique.

One or more components, units, devices, or elements of various embodiments can be packaged and/or distributed as part of a kit. For example, in one embodiment, a stapler, one or more tracking units, 3D viewing glasses, and/or a portion of an ultrasound wand can form a kit. Other embodiments can have different elements or combinations of elements grouped and/or packaged together. Kits can be sold or distributed separately from or with the other portions of the system.

One will readily recognize that there are numerous other examples of image guidance systems which can use, incorporate, support, or provide for the techniques, methods, processes, and systems described herein.

Coordinate Systems

Figure 1B:
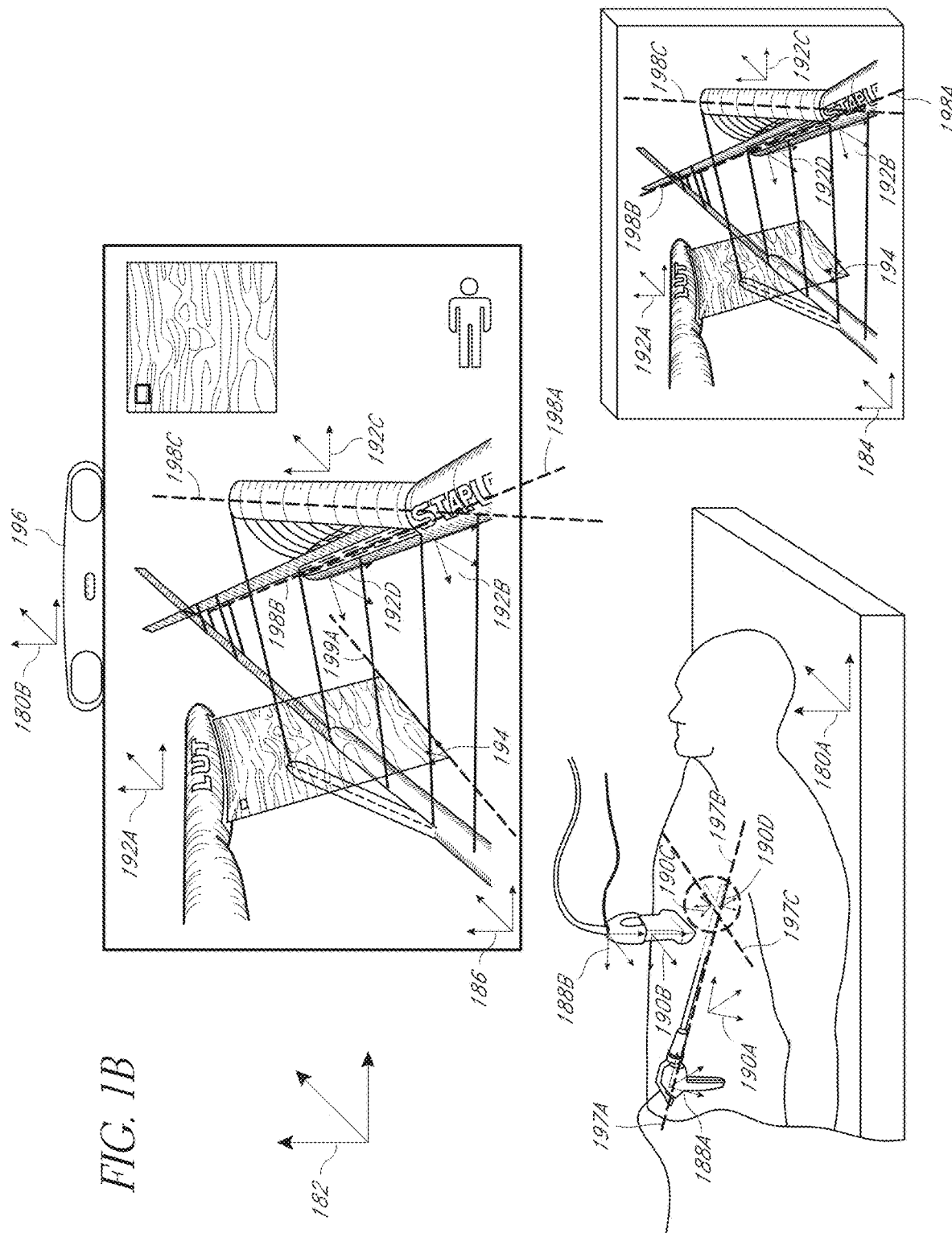
FIG. 1B is a diagram illustrating embodiments of coordinate systems that can be used by the system.

FIG. 1B is a diagram illustrating embodiments of coordinate systems that can be used by the system 100. The system 100 can utilize the coordinate systems to track and display the various display objects on the displays, including, but not limited to one or more position sensing coordinate systems 180A, 180B (generically referred to as 180), one or more room coordinate systems 182, one or more 3D scene coordinate systems 184, one or more display coordinate systems 186, one or more sensor coordinate systems 188A, 188B, one or more medical device coordinate systems 190A, 190B, 190C, 190D, one or more virtual medical device coordinate systems 192A, 192B, 192C, 192D, one or more medical image coordinate systems 194, etc.

A position sensing coordinate system 180 can be used to determine the emplacement of various objects within a position sensing region. For example, in some embodiments, the position sensing coordinate system 180 can refer to the coordinate system 180A used by a magnetic tracker (not shown) tracking objects within a magnetic field volume, or to the coordinate system 180B used by an optical tracker 196 tracking objects within a volume. In some cases, multiple position sensing coordinate systems 180 can be used together. For example, a magnetic position sensing coordinate system 180A can be used in conjunction with a magnetic tracker tracking sensor coils within a position sensing region that are coupled to medical devices and an optical position sensing coordinate system 180B can be used in conjunction with an optical tracker tracking a fiducial coupled to a head mounted display (HMD) or a user, or to an optical tracker analyzing an image captured by an image sensor. It will be understood that any combination of the tracker systems and position sensing coordinate systems 180 can be used as desired. For example, in some cases, a single position sensing coordinate system 180 can be used to track tracking sensors associated with one or more medical devices and/or tracking sensors associated with a user or HMD. Similarly, a different position sensing coordinate system 180 can be used for each tracking sensor, or any combination thereof.

Room coordinate systems 182 can be used to determine the emplacement of objects within a room, such as an operating room. For example, the room coordinate system 182 can be used to determine or identify the relative emplacement of the position sensing unit, medical devices, tracking sensors, user, display, etc. relative to each other within a room.

A 3D scene coordinate system 184, which may also be referred to as a 3D volume or scene graph coordinate system, can be used to determine the emplacement of display objects within a virtual 3D scene. In some cases, the 3D scene coordinate system 184 can identify the relative emplacement of virtual objects within the 3D scene. In certain embodiments, the virtual objects can correspond to real objects, such as to medical devices 145, 155 and/or to computer-generated objects, such as such as trajectory cues 127, affected region 129, etc. Additionally, in certain embodiments, display objects can correspond to real objects, virtual objects, and/or computer generated objects.

A display coordinate system 186 can be used to determine the emplacement of display objects for display on the display 102. For example, the display coordinate system 186 can be used to determine the emplacement of virtual medical devices, medical images, image guidance cues, and the like, within a display 102. In some embodiments, the display coordinate system 186 can be used to determine how the objects within the 3D scene are to be displayed on the display. For example, the display coordinate system 186 can be used to determine the point-of-view location, or eye point, relative to the 3D scene (or 3D volume coordinate system 184) or scene graph for viewing the contents of the 3D scene. As mentioned above, multiple display coordinate systems 186 can be used. For example, left-eye, right-eye, and/or center-eye display coordinate systems 186 can be used to display different perspective of the display objects within a 3D scene, such as when a 3D display and/or an HMD is being used.

A medical image coordinate system 194 can be used in conjunction with medical images used and/or processed by the system. As described previously, the medical images can be ultrasound images, CT image, MRI, images, etc. The images can be different sizes or shapes. For example, one ultrasound can output an image having one size and shape while a different ultrasound can output an image having a different size and/or shape. Similarly, CT, MRI, and ultrasound images may have different sizes and shapes. Accordingly, the medical image coordinate system can be used to identify the particular size and shape of the medical image being used and/or processed by the system 100.

It will be understood that fewer, more, or different coordinate systems can be used as desired. For example, in some embodiments, the 3D scene coordinate system 184 can be omitted or combined with display coordinate system 186 and/or the position sensing coordinate system 180. Furthermore, in some cases, one or more tracking sensor coordinate systems 188A, 188B, medical device coordinate systems 190A, 190B, 190C, 190D, virtual medical device coordinate systems 192A, 192B, 192C, 192D, or other objects etc., can have their own coordinate system. The coordinate systems for the tracking sensors, medical devices, and/or virtual medical devices can be used to identify the dimensions of the sensor/device/display object and relationship of the sensor/device/display object to another sensor/device/display object or other coordinate systems. For example, a medical device coordinate system (or virtual medical device coordinate system) can identify the dimensions of a corresponding medical device or virtual medical device, as well as the emplacement of a tracking sensor relative to the medical device (or vice versa). Similarly, a medical imaging device coordinate system can identify the dimensions of the corresponding medical imaging device (or virtual medical imaging device) and/or an emplacement of a medical image relative to the medical imaging device (non-limiting example: the emplacement of an ultrasound image relative to the corresponding ultrasound transducer), or vice versa. The system 100 can use various coordinate systems to determine the emplacement of a portion or the entire object with respect to each other and with respect to the other coordinate systems.

The system 100 can use the various coordinate systems to determine emplacement of objects relative to each other and determine how to display the display objects on a display, such as the display 102. As a non-limiting example, to display a virtual rendering of an ultrasound transducer 123 and ultrasound image 121 on the display 102, the system 100 can determine the emplacement of a magnetic tracking sensor coupled to the ultrasound transducer 155 within a magnetic position sensing coordinate system 180. Using a magnetic tracking sensor coordinate system 188B, the system 100 can determine the location of each portion of the magnetic tracking sensor within the magnetic position sensing coordinate system 180. The system 100 can also determine the emplacement of each portion the ultrasound transducer 155 within the magnetic position sensing coordinate system by mapping the ultrasound transducer coordinate system 190B to the magnetic tracking sensor coordinate system 188B (or vice versa) and/or to the magnetic position sensing coordinate system 180.

In addition, the system 100 can map each portion of the ultrasound image 121 corresponding to the ultrasound transducer 155 to the magnetic position sensing coordinate system 180 by mapping an ultrasound image coordinate system 194 to the ultrasound transducer coordinate system 190B, the magnetic tracking sensor coordinate system 188B, and/or to the magnetic position sensing coordinate system 180.

To display the virtual ultrasound transducer 123 and ultrasound image slice 121, the system 100 can map the various objects from the magnetic position sensing coordinate system 180 to a room coordinate system 182, which can identify the relative emplacement of the position sensing coordinate system 180 to a display. The system can then map data to the 3D scene coordinate system 194 and/or the display coordinate system 186. For 3D viewing, the system 100 can map the objects to multiple display coordinate systems 186, such as left-eye and/or right-eye coordinate systems.

With continued reference to the non-limiting example, the system 100 can determine an emplacement of an optical tracking sensor corresponding to a user within an optical position sensing coordinate system 180B. The emplacement of the optical tracking sensor within the optical position sensing coordinate system 180B can be mapped to the room coordinate system 182, the 3D scene coordinate system 184, and/or the display coordinate systems 186 for display. In this way the system 100 can determine the emplacement of the ultrasound transducer 155 and ultrasound image slice 121 relative to the user and display a virtual rendering of the ultrasound transducer 123 and ultrasound image slice 121 within the 3D scene relative to the determined emplacement of the user.

To display the virtual ultrasound transducer 123 and ultrasound image slice 121, the system 100 can map the various objects from the magnetic position sensing coordinate system 180 to a room coordinate system 182, which can identify the relative emplacement of the position sensing coordinate system 180 to a display. The system can then map data to the 3D scene coordinate system 194 and/or the display coordinate system 186. For 3D viewing, the system 100 can map the objects to multiple display coordinate systems 186, such as left-eye and/or right-eye coordinate systems.

Although the non-limiting examples have been described as mapping the various objects and coordinate systems, to a position sensing coordinate system 180, the room coordinate system 182, the 3D scene coordinate system 184, and to display coordinate systems 186, it will be understood that the one or more of the objects or coordinate systems can be mapped directly or indirectly to any other coordinate system. For example, the medical device image can be mapped directly to a left-eye display coordinate system 186, etc. Thus, any of the real or virtual objects described herein may be represented, detected, or imaged in any coordinate system, and conversion between the various coordinate systems can be performed in components of the system such as image guidance unit 130, position sensing unit 140, imager 150, the an HMD, or other components.

Furthermore, it will be understood that once the system 100 determines an emplacement of a medical device in one coordinate system, such as a position sensing coordinate system 180, the system 100 can determine the emplacement of a corresponding virtual medical device in a different coordinate system, such as the 3D scene coordinate system 184 or the screen coordinate system 186, by mapping the coordinates of the first coordinate system to the coordinates of the second coordinate system, or vice versa. Accordingly, references made herein to determining an emplacement of the medical device can also refer to determining an emplacement of a virtual medical device corresponding to the medical device, or vice versa. Similarly, references made herein to determining an emplacement of a display object (non-limiting example: medical image) relative to the medical device can also refer to determining the emplacement of the display object relative to a corresponding virtual medical device.

Depicting Medical Devices

It can often be difficult to discern the content of a 3D scene from a 2D depiction of it, or even from a 3D depiction of it. Therefore, various embodiments herein provide image guidance that can help the healthcare provider better understand the scene, relative emplacements or poses of object in the scene and thereby provide improved image guidance.

Figure 2:
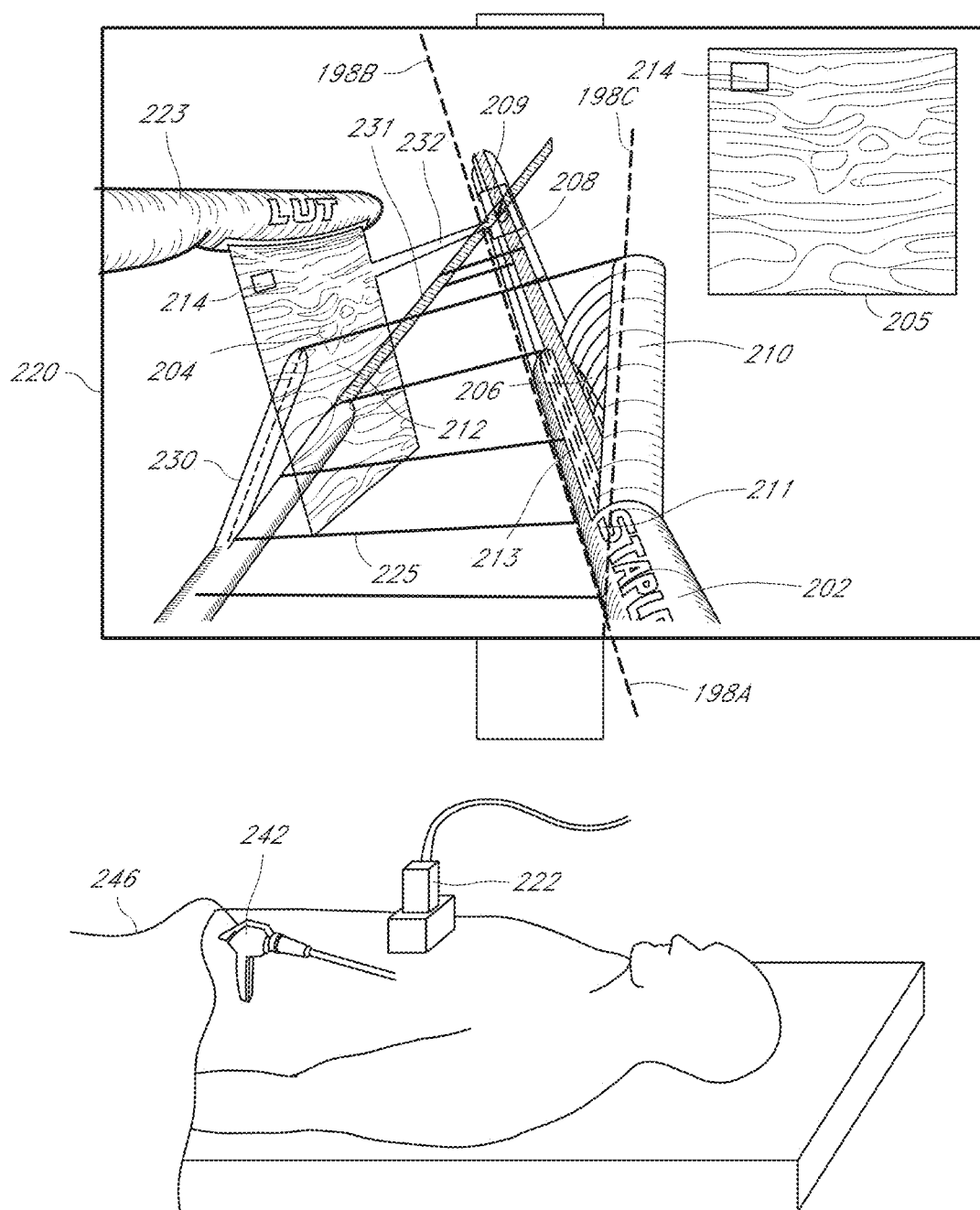
FIG. 2 is a diagram illustrating an embodiment of a rendering of image guidance cues and medical display objects on a display.

FIG. 2 illustrates a perspective view of a virtual rendering 202 of a medical device 242 being displayed on a screen 220 with a perspective view of a medical image 204. In some embodiments, the screen 220 can correspond to the screen of a display unit 120, which can be implemented using a TV, computer screen, head-mounted display, projector, etc. In the illustrated embodiment, the virtual medical device 202 displayed on the screen 220 corresponds to the stapler 242. A wire 246 connecting the stapler 242 to a stapler navigation system is also depicted in FIG. 2.

Although only one virtual medical device 202 is displayed, it will be understood that multiple medical devices can be tracked and displayed concurrently, or simultaneously, on screen 220, as described in greater detail in the '274 Application, previously incorporated by reference. For example, a virtual rendering of the medical imaging device 222 can be displayed.

The virtual medical device 202 (which can also be referred to as an avatar) can be displayed in a virtual 3D space with the screen 220 acting as a window into the virtual 3D space. Thus, as the medical device 242 is moved to the right with respect to a point-of-view location (e.g., the location of the point-of-view for viewing the 3D space), the virtual medical device 202 also moves to the right. Similarly, if the medical device 242 is rotated 90 degrees so that the tip of the medical device is pointing away from the point-of-view location (e.g., at the screen 220), the virtual medical device 202 will likewise show the change in orientation, and show the tip of the virtual medical device 202 in the background and the other end of the virtual medical device 202 in the foreground. In some embodiments, as described in greater detail in U.S. patent application Ser. No. 14/212, 933, filed Mar. 14, 2014, entitled MEDICAL DEVICE GUIDANCE (the '933 Application), incorporated herein by reference in its entirety, the point-of-view location can be a fixed location, such as a predetermined distance/angle from the screen 220 or stand 170 and/or a location configured by the user; or the point-of-view location can by dynamic. For example, the system can track a user in real-time and determine the point-of-view location based at least in part on the tracked location of the user.

Some models of medical devices have markings such as bands around the shaft or jaws to indicate distance along the shaft or jaws. Healthcare providers performing medical device procedures are often familiar with these markings and can use them to help understand the spatial relationship between the medical device and anatomy. In some embodiments, the make and model of the medical device 242 is known to the image guidance system and the virtual medical device 202 displayed in display 220 can resemble medical device 242. The features of medical devices that can be rendered in the scene include the overall shape (diameter, angles, cross sectional shape, curvature, etc.), color, distance markers, angle of the jaws, visuals or echogenic fiduciary markers, the state of deployable elements such as tines, paddles, anchors, resection loops, stiffening or steerable sleeves, temperature, radiation, light or magnetic field sensors, lens, waveguides, fluid transfer channels, and the like.

The type of medical device being used can be input into the image guidance system 100, can be a system default, can be detected by a camera or other device, can be received as data from an attached medical device, such as surgical system 149 in FIG. 1, or the information can be received in any other appropriate manner. Displaying on display 220, a virtual medical device 202 that resembles the medical device 242 can help healthcare providers associate the image guidance data with the real world and can provide more familiar guidance information to a healthcare provider, thereby further aiding the healthcare provider in the guidance task. For example, the healthcare provider can see the familiar markings on the medical device 202 being displayed on the display 220 and therefore be familiar with the distance and relative placement of the displayed medical device 202 with respect to other data, such as tissue 212 seen in a medical image 204, 205. This knowledge of relative placement of items being displayed can help the healthcare provider move the medical device 242 into place. It should be understood that the terms medical device and virtual medical device can sometimes be used interchangeably as they can generally relate to the same object, the medical device being the object in the real world and virtual medical device being a representation of the object, such as an avatar, in virtual space. Additionally, in some instances virtual medical device can sometimes be referred to as virtual surgical instrument, surgical instrument, rendered surgical instrument, rendered medical device, avatar, rendered avatar, and virtual avatar.

Consider an embodiment in which the virtual medical device 202 in the display 220 is a virtual stapler depicting the portion of the stapler that will perform the stapling. The displayed virtual medical device can include a joint member 211, a first limb member 213, and a second limb member 210. If the display 220 also includes ultrasound data, then the doctor can find the tissue she wishes to staple by moving the ultrasound probe 222 until she identifies the target tissue. In various embodiments, she will be able to see the displayed ultrasound data and its location relative to the displayed medical device 202. She can then direct the medical device 242 until she sees, on display 220, that the affected region of the virtual medical device 202 encompasses a desired stapled region of the tissue in the medical image. When she activates the stapler 242, she can have a higher degree of confidence that she has stapled the correct portion of the tissue. Various embodiments of this are discussed below.

As another example, consider the physical markings that can be on the instruments themselves. These markings can help orient a healthcare provider during use of the instrument. In some embodiments, the image guidance unit can represent these markings in the images displayed in the display. For example, certain ultrasound transducers are built with an orientation mark (e.g., a small bump) on one side of the transducing array. That mark can also be shown in the medical image on the scanner's display, to help the healthcare provider understand where the scanned anatomical structures shown on screen are located under the transducer, inside the patient.

In some embodiments, the image guidance system can display a symbolic 3D representation of an orientation mark 214 both next to the motion-tracked ultrasound slice (e.g., moving with the displayed ultrasound slice) and next to the 2D view of the ultrasound slice also displayed by the system. An example of this orientation mark is displayed in FIG. 2, where a small rectilinear volume 214 is shown both in proximity to the ultrasound slice displayed in the 3D view and the ultrasound slice displayed in a 2D view. In some embodiments, the orientation mark 214 corresponds to a feature, such as a physical marking, of the ultrasound probe. In some embodiments, the orientation mark 214 is displayed to provide assistance in associating the 3D view and the 2D view.

It will be understood that a medical image can correspond to image data received from an imaging device, such as an ultrasound transducer. In some embodiments, the image data can correspond to a cross-section of tissue having a certain thickness. In some instances, the imaging device can compact the image data, and/or treat the image data as 2D data, such that there is no perceived thickness. In certain embodiments, when the medical image is displayed in a 3D view, the system can treat the medical image as a 2D or quasi 2D object. In such embodiments, the system can cause the medical image to have little to no perceptible thickness. Accordingly, in certain embodiments, when the medical image is oriented orthogonally or perpendicularly with respect to the point-of-view location, the system can cause the display to display nothing or a line having a relatively small thickness, such as a few pixels, etc. In some cases, the number of pixels used to display the relatively small thickness of the medical image can correspond to the size of the display. For example, more pixels can be used for a larger display and fewer pixels can be used for a smaller display, etc.

Other embodiments can track and display other types of instruments and their features. For example, a healthcare provider may want to track one or more of a stapler, vessel sealer, grasper, scalpel, a biopsy, a cauterizer (including an electrocauterizer and Bovies), forceps, cutting loops on hysteroscopes, harmonic sheers, lasers (including $CO_2$ lasers), etc. For example, in various embodiments, the following devices can be tracked and various aspects of their design displayed on display 220: Olympus™ OES Pro Hystero-Resectoscope, SonoSurg Ultrasonic Surgical System Olympus™ GF-UC 160 Endoscope Wallus™ Embryo Transfer Catheter AngioDynamics™. NanoKnife™, VenaCure™ laser, StarBurst, Uniblade, Habib™. Resector Bovie™ Electrodes, Covidien Evident™, Cool-tip™ Ablation Antennas, Opti4™ Electrodes Microsulis MEA (microwave endometrial ablation), Acculis Halt™ Medical System Optimed BigLumen Aspiration Catheter Optimed Optipure Stent Central venous catheterization introducer medical device (such as those made by Bard and Arrow).

Once tracked, a healthcare provider is able to see image guidance data on display 220 that will allow her to know the relative pose, location, or emplacement of the tracked instrument(s) with respect to one another or with respect to imaging data and will be able to see, on display 220, the features of the instrument rendered in the scene.

With continued reference to FIG. 2, in some embodiments, the image guidance system can constantly display an additional 2D view 205 of the medical image, simultaneous to the 3D depiction 204, so that the medical image is always visible, regardless of the emplacement in which the healthcare provider holds the transducer 222. The 2D view 205 of the medical data can be similar to what a healthcare provider is accustomed to seeing with traditional medical displays, such as ultrasound displays. This can be useful to provide the healthcare provider with imaging to which she is accustomed and allows a healthcare provider to see the medical data regardless of the then-current emplacement of the imaging device with respect to the user.

In some embodiments, the 2D view 205 of the medical image is depicted in the upper right corner of the monitor (though it can be placed in any location). In some embodiments, the guidance system can automatically (and continually) choose a corner in which to render the 2D view 205 of the medical image, based on the 3D position of the medical devices in the rendered scene. For example, in FIG. 2, stapler 242 can be held in the healthcare provider's left hand and the medical device shaft is to the left of the 3D view of the medical image, so that the 2D view 202 of the medical image in the upper right corner of display 220 does not cover any of the 3D features of the medical device (or vice-versa). If the medical device were held in the healthcare provider's right hand, the virtual medical device shaft would appear on the right side. To prevent the 2D view 205 in the corner of display 220 from covering the medical device shaft, the system can automatically move it to a corner that would not otherwise be occupied by graphics or data.

In some embodiments, the system attempts to avoid having the 2D view 205 of the medical image quickly moving among corners of the display in order to avoid overlapping with graphics and data in the display. For example, a function f can be used to determine which corner is most suitable for the 2D medical image to be drawn in. The inputs to f can include the locations, in the screen coordinate system, of the displayed medical device tip, the corners of the 3D view of the medical image, etc. In some embodiments, f s output for any given point in time is independent of f s output in the previous frames, which can cause the medical image to move among corners of the display rapidly. In some embodiments, the image guidance system will filter f s output over time. For example, the output of a filter g, for any given frame, could be the corner, which has been output by f the most number of times over the last n frames, possibly weighting the most recent values for f most heavily. The output of the filter g can be used to determine in which corner of display 220 to display the 2D medical image and the temporal filtering provided by g can allow the 2D view 205 of the medical image display to move more smoothly among the corners of the display 220.

In some embodiments, other appropriate virtual information and/or image guidance cues can be overlaid on the 2D view 205 of the medical image as well as the 3D view 204. Examples include: orientation indicator 214, an indication of the distance between the medical device's tip (for example, the tip of the first limb member or the tip of the second limb member) and the point in the plane of the medical image that is closest to the medical device tip; ghost affected area (e.g., a cross section or outline of the affected region projected on the ultrasound slice); and/or intersection indicators (e.g., a point, box, outline, etc.) indicating an intersection between one or more axes or trajectories of a display object and a plane-of-interest (e.g., a medical image plane, a medical device plane, etc.).

Furthermore, it will be understood that other image guidance cues can be generated and displayed on the display as described in greater detail in the '274 Application, previously incorporated herein by reference. For example, the system 100 can generate and/or display graphical indicators that help indicate the spatial relationship between a medical device and an medical image plane (e.g., graphical image plane indicators) or other plane (e.g., graphical plane indicators), indicators to indicate the relative positions of the medical device(s) and medical image(s), features of interest, annotations, plane indicators, plane intersection indicators, other graphical indicators, approximate medical device location indicators, etc. As described in greater detail above and in the '274 Application, the various image guidance cues can be generated based at least in part on the emplacement information of the medical devices used with the system 100.

Multi-Axis Device

With reference to FIGS. 1B and 2, one or more of the medical devices or the system 100 can be a multi-axis medical device. For instance, the multi-axis medical device 203 can be a number of devices including two or more axes or jaws, such as, but not limited to graspers, staplers, vessel sealers, electrocauterizers, resecting devices, transecting devices and scalpels. As depicted, a distal end of the multi-axis medical device 202 includes a joint member 211, and two limb members 213, 210 coupled to the joint member 211 at different angles. In some examples, the multi-axis medical device 202 can have a number of associated axes. For instance, the joint member 211 can have a joint member axis 198A, the first limb member 213 can have a first axis 198B, and the second limb member 210 can have a second axis 198C that is different from the joint member axis 198A and the first axis 198B. In some embodiments, such as the illustrated embodiment of FIG. 2, the joint member axis 198A is the same as the first axis 198B. However, it will be understood that in some cases, the joint member axis 198A, first axis 198B, and second axis 198C can all be different. For example, the first member 213 may be angled relative to the joint member 211 and the second member 210.

In some examples, the multi-axis medical device 202 can have one or more primary axis and/or one or more secondary axis. For instance, in some embodiments, the primary axis can correspond to the longitudinal axis of a body of a medical device or portion of a medical device where two or more limbs are joined, such as joint member 211 (or joint member axis 198A) and the secondary axis or axes can correspond to the longitudinal axis or axes of the limb members of the medical device, such as limb members 213, 210 (or first axis 198B and/or second axis 198C). In some cases, one or more of the secondary axes can be coincident with the primary axis or parallel to the primary axis. In certain cases, one or more of the secondary axes can move relative to the primary axis.

The one or more limb members 213, 210 can be movable and/or fixed. For instance, in the illustrated embodiment of FIG. 2, the first limb member 213 (or lower jaw) is fixed relative to the joint member 211, and the secondary axis corresponding to the limb member 213 is parallel to the primary axis. In some cases, one or more of the limb members can be an extension of the joint member 211. For example, if the medical device is a stapler with two jaws, the primary axis can correspond to the joint member axis 198A of the stapler or where the two jaws meet and the secondary axes can correspond to the axes of the limb members 198B, 198C.

With continued reference to the embodiment illustrated in FIG. 2, a second secondary axis can correspond to the axis 198C of the second limb member 210 (or upper jaw) and is not parallel to the joint member axis 198A or the first axis 198B in a first configuration. The second limb member 210 can be moveable relative to the joint member 211 and the first limb member 213. In some cases, the second limb member 210 is hingeably connected to the joint member 211. In certain cases, the range of motion of the second limb member 210 can be an operating parameter input into the system 100. In some embodiments, the range of motion of the second limb member 210 is limited by the hinge. In certain embodiments, a limb member (e.g., upper or lower jaw) can be affixed to the joint member 211.

In a second configuration, such as when the multi-axis device is operated or closed, the second limb member 210 can be parallel or approximately parallel (e.g., within 5, 10, 15, or 20 degrees of parallel (+/− a few degrees)) to the joint member 211. Thus, the secondary axis 198C can change relative to the primary axis as the second jaw 210 moves. For example, if the multi-axis device 202 is a stapler, the stapler 202 can be in a first configuration when the stapler in not activated. The stapler may be in a second (or stapling) configuration when the stapler in activated (e.g., the staples are being applied). In the stapling configuration, the second jaw 210 can be parallel (or approximately parallel) to the joint member 205. In such cases, in the first configuration, the secondary axis 198C is not parallel to the primary axis 198A, and in the second configuration, the secondary axis 198C is parallel (or approximately parallel) to the primary axis 198A. Further, while moving from the first configuration to the second configuration, the secondary axis 198C is not parallel to the primary axis 198A.

In certain embodiments, both the first limb member 213 and the second limb member 210 are affixed to the joint member at different angles such that the primary axis and secondary axis or axes are all different (e.g., the joint member axis 198A, the first axis 198B, and the second axis 198C are all nonparallel). Thus, in some examples, there are at least three nonparallel axes between the joint member 311 and limb members—the primary axis, the first secondary axis and the second secondary axis.

Figure 10:
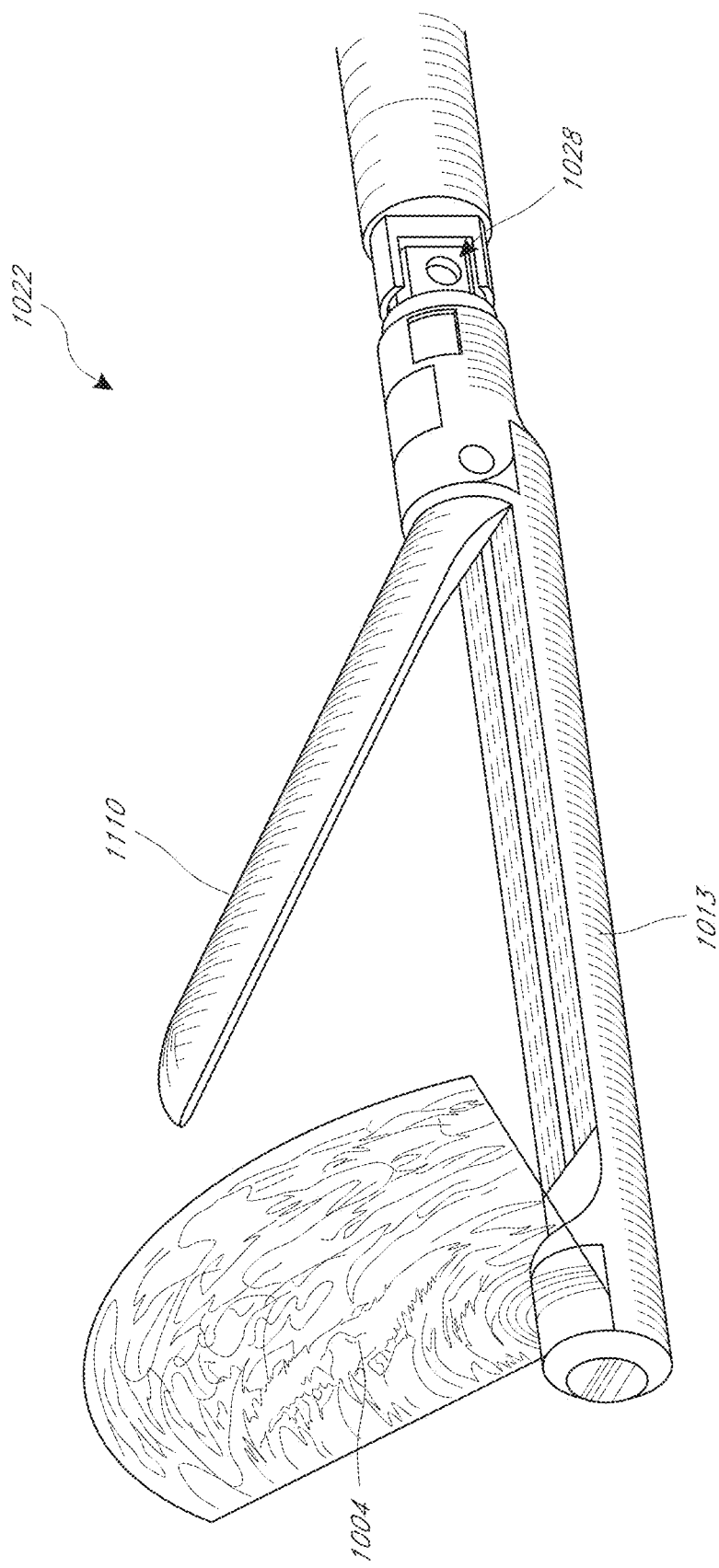
FIG. 10 is a diagram illustrating an embodiment of a medical device having an integrated imaging device.

In some embodiments, the multi-axis medical device 202 can have more than three axes and/or can have more than one primary axis. For instance, the joint member 211 can have more than one axis. As an example, the joint member can include one or more bends or hinges (as depicted in FIG. 10) wherefrom the joint member 211 can be articulated relative to a proximal shaft of the medical device.

Depicting Medical Device Placement, Trajectory, and Other Image Guidance Cues

In certain procedures, the system can provide image prediction information related to the medical devices as image guidance cues. With continued reference to FIG. 2, the display 220 illustrates a 3D model of a multi-axis medical device 202, a second medical device 223, a medical image 204, and image guidance cues. While FIG. 2 depicts the multi-axis medical device as a virtual stapler 202, the virtual medical device 202 could include any two jaw device, including but not limited to a transector, resector, sealer, or grasper. Further, while the depicted multi-axis device includes three axes, in some embodiments, the multi-axis device can include two, three, four, five or more axes. For example, the multi-axis device could include three limb members extending out along nonparallel axes from a joint member.

In the illustrated embodiment, the medical device includes a joint member 211 having a joint member axis 198A, a first limb member 213 having a first axis 198B, and a second limb member 210 having a second axis 198C that is different from the joint member axis 198A and the first axis 198B. As mentioned above, the primary axis can correspond to the joint member axis 198A or longitudinal axis of the joint member 211, and the secondary axes can correspond to the first axis 198B and the second axis 198C. In the illustrated embodiment of FIG. 2, one secondary axis (e.g., first axis 198B) is parallel to the primary axis and another secondary axis (e.g., second axis 198C) is not parallel to the primary axis. However, it should be understood that any of the secondary axis can be parallel or not parallel to the primary axis. It should also be noted that, in some embodiments, a display object includes more than one primary axis.

In some embodiments, a trajectory (or trajectory indicator) of a display object can be determined and displayed. For instance, a trajectory indicator can be displayed to indicate the trajectory of an associated display object, if that display object is moved along a drive path. In some embodiments, the drive path can be dynamic in that it can correlate to the path of the medical device when moved by a user. For instance, the system can determine that the display object (e.g., medical device) is being moved and, in response, can calculate a drive path which corresponding to the path the medical device would take if it continued to move in the same direction. However, it should be understood that the drive path can be predetermined or dynamic. For instance, the drive path can correspond to a path that is parallel to a primary axis of the display object (akin to moving the medical device forward/backward). As another example, the drive path can correspond to a path that is perpendicular to a primary axis of the display object (akin to moving the medical device up/down or side-to-side). Similarly, the drive path can be parallel or perpendicular to a secondary axis. In some embodiments, a display object can have a predetermined drive path when the system determines the display object is not moving and can have a dynamic drive path when the system detects movement.

In a non-limiting example, the display object can be a multi-axis medical device (e.g., a virtual stapler 202) having a joint member 211, a first limb member 213, and second limb member 210. A trajectory can be calculated, determined, and displayed for the first limb member 213, the second limb member 210 and/or the joint member 211. For example, each of the trajectories can be calculated based on a drive path for the medical device. In some cases, the trajectory for each member of the medical device can correspond to the path that that portion of the medical device (i.e., the joint member 211, the first limb member 213, and the second limb member) will follow if the medical device is moved along the drive path. In some embodiments, the system 100 can display a trajectory indicator for a distal portion of each limb member and/or joint member of the medical device. However, it should be understood that a trajectory indicator can be displayed for any and/or all portions of a display object. Similarly, in some embodiments (as illustrated in FIG. 2), a trajectory indicator may be displayed for some portions (e.g., the first limb member) and not displayed for other portions (e.g., the second limb member).

Referring to the non-limiting example above, trajectory indicators (e.g., 308A, 308B, 308C, and 308D of FIG. 3) can indicate a trajectory along an axis that is different from and parallel to the primary axis (non-limiting example: an axis corresponding to a distal portion of a limb member along the drive path). In addition, the trajectory indicators can extend through or to a distal portion (e.g., the tip) of the medical device (e.g., a distal portion of the second limb member 310). In some cases, the intersection indicators can correspond to, or track, an axis that intersects with a limb member axis (or secondary axis) at a distal portion of the limb member and is parallel to the joint member axis (or primary axis) and/or the drive path.

In some embodiments, such as when both limb members are nonparallel to the joint member, the trajectory indicator(s) can be determined based on a trajectory of the medical device along a primary axis (non-limiting example: drive path that is parallel to the primary axis). In such embodiments, the trajectory of the limb members can be determined based on axes that are different from, but parallel to the primary axis and extend through a distal (or other) portion of the limb members.

Figure 3:
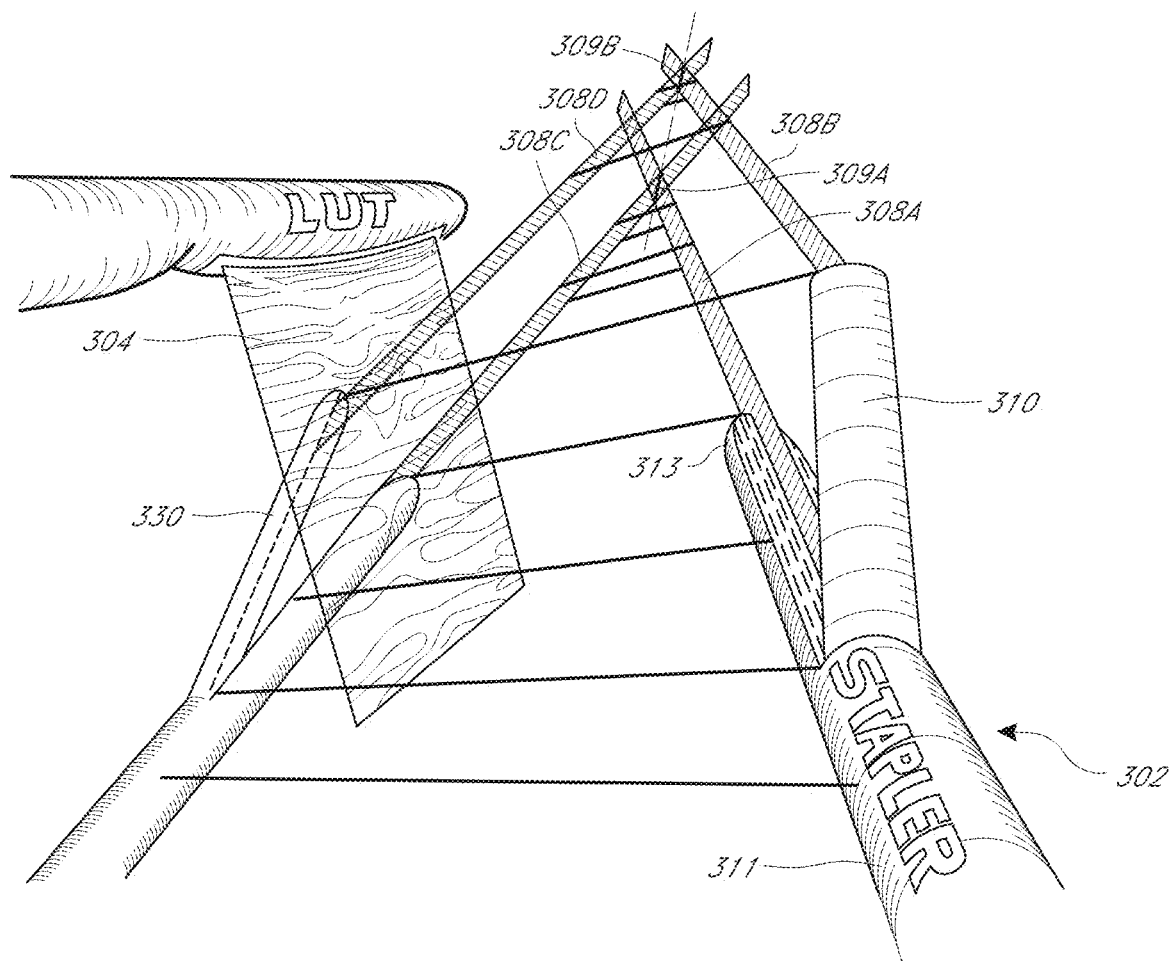
FIG. 3 is a diagram illustrating an embodiment of a rendering of image guidance cues and medical display objects, including a ghost medical device.

While FIG. 2 illustrates a trajectory indicator 208 of a knife path of the first limb member 213, the system can additionally or alternatively include a trajectory indicator of the second limb member 210 (as shown in FIG. 3), joint member 211, and/or a transecting knife (as shown in FIG. 3). In some embodiments, the trajectory indicator can indicate the trajectory of the medical device along a primary axis and/or the secondary axis. As mentioned above, the system can display one or more trajectory indicators, which can indicate the trajectory of a display object if the display object is moved along a drive path. The trajectory (e.g., trajectory indicator 208) of the medical device 202 can be depicted on the display 220 and can show the healthcare provider the projected path that the medical device will take when moved.

A trajectory indicator can be displayed for any display object (for example, virtual medical devices, affected regions, ghost display objects, image guidance cues, etc.) to indicate the trajectory of the display object if moved along a drive path (e.g., corresponding to a primary axis, a secondary axis, an axis parallel to the primary axis, etc.). In some embodiments, a trajectory indicator indicates the trajectory of a display object if the display object is moved along an axis parallel to the axis of another display object's axis or plane.

In some embodiments, as described below, a display object can be geometrically projected onto a plane-of-interest (i.e., the plane to which that the display object is to be projected) to display a ghost display object (e.g., an outline, cross section, or indication of the display object on the plane-of-interest). In a non-limiting example, the ghost display object can be a ghost medical device having a joint member, a first limb member, and second limb member. The system can determine and/or calculate a trajectory of the ghost medical device by determining the trajectory of the joint member, first limb member, and/or second limb member if the ghost medical device is moved along a primary or secondary axis of the ghost medical device. It will be understood that the trajectory of multiple display objects can be determined and displayed simultaneously on screen 220, as described in greater detail in the '274 Application. Further, it will be understood that the ghost display object can correspond to any display object. For example, the ghost display object can correspond a single axis medical device, such as a needle, as described in greater detail in the '274 Application.

In addition, in some examples, as described in greater detail below with respect to FIG. 3, the guidance cues can include a ghost medical device 230 (also referred to as a projected or mapped medical device) on the image plane. In these examples, the system can additionally or alternatively display one or more trajectories (e.g., trajectory indicators) of the ghost medical device, such as trajectory indicator 231.

In some embodiments, to implement trajectory indicators, the image guidance system can draw a number of rings about the joint member axis 198A, the first axis 198B, the second axis 198C, or an axis parallel or perpendicular to the joint member axis 198A, the first axis 198B, or the second axis 198C and emanating from a distal (or other) end of a limb member. The trajectory indicators can be extrapolated beyond the tip of the first limb member, second limb member or joint member. In examples which include a ghost medical device, the image guidance system can draw similar trajectory indicators about the one or more axes corresponding to the ghost medical device 230. For example, ghost medical device 330 can include a first and second limb member from which a trajectory indicator can be drawn. Furthermore, the image guidance system can draw a number of rings about an axis of another medical device (for instance, the imaging device).

A healthcare provider can view and manipulate the emplacement of the medical device 242 and its trajectory (via an associated trajectory indicator) before it enters the patient's body along a drive path. In some embodiments, this is accomplished by the doctor positioning a trajectory indicator (e.g., virtual rings or cues) such that it is coincident (or passes through) an ultrasound representation of a target such as tissue that the doctor has spotted in the ultrasound. Positioning the trajectory indicator(s) such that it is properly aimed at the target can provide guidance to the doctor as she directs a medical device 242 into the body until it reaches its desired target or destination. For example, if the doctor identifies tissue 212 in the medical image which needs attention, she can align the stapler 242 such that the trajectory indicators on display 220 intersect or otherwise indicate that the medical device, if directed along the appropriate axis, will reach the tissue 212.

In some embodiments, it may be advantageous for the doctor to position the trajectory indicator (e.g., virtual rings, cues, etc.) such that it is not coincident (or does not pass through) the ultrasound representation of a target. For example, with respect to a stapler, it may be advantageous to align the stapler such that it is substantially parallel with and on or adjacent to the image plane, rather than aligning the stapler such that it intersects the image plane. By aligning the stapler in this manner, the healthcare provider can use the medical image 204 to see more of what tissue will be affected (e.g., the affected region) when the stapler is activated.

The rings can, in some embodiments, be spaced at regular (e.g., 0.5, 1, or 2 cm) intervals to provide the healthcare provider with visual or guidance cues regarding the distance from the medical device tip to the targeted anatomy. In some embodiments, the spacing of the rings can indicate other aspects of the data, such as the speed of the medical device, the density of the tissue, the distance to a landmark, such as the ultrasound data, or any other appropriate guidance data or property. In some embodiments, the rings or other trajectory indicators can extend beyond the medical device tip, by a distance equal to the length of the medical device shaft. This way, the user knows if the medical device is long enough to reach the target, even before the tip(s) enter the patient. That is, in some embodiments, if the rings do not reach the target with the tip still outside the body, then the tip will not reach the target even when the entire device is inserted into the body. In some embodiments, such as when it is preferable to aim the medical device 202 at a target beyond the medical image 204, the trajectory indicator 308 can extend to or even past the image plane.

Other display markers can be used to show trajectory, such as a dashed, dotted, or solid line, transparent medical device shaft, point cloud, wire frame, etc. In some embodiments, three-dimensional rings can be used and provide depth cues and obscure little of the medical image. Virtual rings or other virtual markers can be displayed semi-transparently, so that they obscure less of the medical image than an opaque marker would.

In addition, connecting lines 225 can also be drawn from a plane-of-interest (e.g., medical image plane) to a display object (e.g., virtual medical device 202) or a display object plane (e.g., virtual medical device plane). In some embodiments, the connecting lines extend orthogonally or perpendicularly from a plane-of-interest to a display object plane or a display object. In some embodiments, the connecting lines extend orthogonally or perpendicularly from a display object plane or a display object to a plane-of-interest. However, it will be understood that in some embodiments the connecting lines 225 are not orthogonal (or perpendicular) to any plane. In some embodiments, the connecting lines 225 can be used to determine or display the difference in angle between a plane-of-interest and a display object plane. In some cases, the connecting lines can have an arc. The arc can be determined by treating the intersection of the two display object trajectories as the center of a sphere or circle and treating the connecting line as a perimeter of the circle or sphere.

Other prediction information can also be displayed as image guidance cues. For example, if a stapler is being tracked by the image guidance system, then a cutting plane corresponding to the trajectory of a transecting knife of the stapler can be displayed. Such a cutting plan can be coplanar with the transecting knife of the stapler and can extend from the transecting knife of the stapler (for instance, along the axis of the first member) to, for instance, a plane-of-interest. For example, the trajectory indicator of the transecting knife (e.g., cutting plane) can show where the stapler would cut if the doctor were to advance the stapler along a drive path. Similar prediction information can be estimable or determinable for graspers, vessel sealers, resecting devices, transecting devices, scalpels cauterizers, lasers, and numerous other medical devices.

Furthermore, the data from two or more devices can be combined and displayed based on their relative emplacements or poses. For example, the system 100 can determine the emplacement of an image plane based on the emplacement information of the ultrasound probe 222. Further, the medical image 204 can be displayed on the image plane with respect to the virtual medical device 202 on the display 220 in a manner that estimates the relative emplacements or poses of an ultrasound probe 222 and the medical device 242. As illustrated in FIG. 2, the image guidance cues associated with the virtual medical device 202, including trajectory indicators, are shown spatially located with the medical image 204 on display 220.

Projecting a Ghost Display Object onto a Plane-of-Interest

In some embodiments, the system 100 can provide additional guidance cues that facilitate understanding of the relationship between the image plane and the medical device(s). For example, display objects (e.g., medical display objects (medical devices, medical images, affected regions, etc.) or image guidance cues (trajectory indicators, intersection indicators, plane indicators, etc.)) can be geometrically projected onto a plane-of-interest such that a shadow, outline (e.g., a dashed, dotted, or solid line), marking, transparent display object, point cloud, wire frame, or other indication of the display object is displayed on the plane-of-interest. In some embodiments, the projected display objects (e.g., projected medical devices, projected medical images, projected image guidance cues, etc.) are known collectively as ghost display objects.

In some embodiments, the plane-of-interest is the plane to which that the display object is to be projected. For example, the plane-of-interest can be an image plane (e.g., the plane corresponding to a medical image), a medical device plane (e.g., the plane corresponding to a virtual medical device), or any other display object plane or other desired plane. In some embodiments, the plane-of-interest can include only a portion of a plane (e.g., the medical image portion of the image plane). However, it will be understood that a plane-of-interest can include more than a portion of any plane including but not limited to the image plane, medical device plane, affected region plane, or other display object plane. In some embodiments, the plane-of-interest can be determined dynamically based on the display object plane. Further, in some cases, the plane-of-interest can be selected to be a plane that is parallel to the display object plane. For example, the plane-of-interest can be selected as the display object plane (as described below) that is parallel to the image plane of a medical image. However, it will be understood that in some cases, the plane-of-interest can be predetermined, such as a display object plane that bisects the display object into halves.

In some embodiments, the display object plane corresponds to any plane that is parallel to a primary or secondary axis of the display object. In some embodiments, the display object plane corresponds to a plane that bisects the display object (e.g., a virtual medical device) into portions (e.g., left and right portions, top and bottom portions, etc.). In some cases, a display object plane can be determined dynamically based on the plane-of-interest. Further, in certain cases, the display object plane can be selected to be a plane that bisects the display object and that is parallel to the plane-of-interest. For example, the display object plane can be selected as a plane (e.g., a plane corresponding to an axis of the display object) that is parallel to the plane-of-interest. Thus, the display object plane can change as the display object moves throughout the system. However, it will be understood that in some cases, the display object plane can be predetermined.

A ghost display object (e.g., projected display object) can be projected onto a plane-of-interest using a variety of techniques. For example, the ghost display object can be an orthographic projection of the display object onto the plane-of-interest. As a non-limiting example, the display object is a virtual medical device and the plane-of-interest is an image plane. The system calculates a plurality of lines which are perpendicular to the image plane. For each perpendicular line that intersects the virtual medical device (or a subset thereof), a point is displayed on the image plane at the location corresponding to the intersecting perpendicular line. As a result, a plurality of points are displayed on the image plane which correspond to the plurality of perpendicular lines (or subset thereof) intersecting the virtual medical device. The plurality of points can illustrate an indication of the virtual medical device on the image plane. In some embodiments, the plurality of points can be referred to as a ghost, a shadow, an outline, a marking, a projection, or an indication of the virtual medical device. It should be understood that the number of perpendicular lines (and the number of corresponding points) can vary across embodiments. For example, in some embodiments, there can be almost infinite perpendicular lines such that a complete representation of the virtual medical device is displayed on the image plane. In some embodiments, the perpendicular lines can be spaced out at predefined intervals such that the ghost medical device includes a dotted outline or dotted representation of the medical device. Similarly, in some cases, the subset of perpendicular lines used to generate the ghost display object can correspond to lines that intersect with a particular portion of the virtual medical device, such as the edge thereby creating an outline on the plane-of-interest.

In some embodiments, a ghost display object can be projected onto a plane-of-interest using a virtual light source. Consider a virtual light source that is at least as large as the display object to be projected or that covers an entire plane (e.g., a light source plane) positioned behind the display object (e.g., distal the plane-of-interest relative to the display object) and parallel to the plane-of-interest, and that emits parallel light waves. In examples such as these, the ghost display object can be displayed on the plane-on-interest as a shadow of the display object. Because the light source is infinitely wide (and can be infinitely far away), the size of the ghost display object can correspond directly with the size of the display object. Further, it will be understood that in some cases, the system can display an outline of the shadow generated by the virtual light source or other indicator.

In some embodiments, a display object can be projected by identifying points on a display object plane that correspond (e.g., intersect) to the display and mapping (e.g., projecting, reproducing, copying) the identified points onto a plane-of-interest. In some embodiments, the identified points on the display object plane can include a plurality of points (e.g., coordinates) that intersect with the corresponding display object. For instance, the plane of a virtual medical device can be a plane that bisects the virtual medical device. The plane can include a plurality of points that intersect with the virtual medical device. In a non-limiting example, to project the virtual medical device onto an image plane, at least some of the plurality of intersecting points can be drawn on the image plane. In certain cases, as described above, the resulting ghost medical device can include an outline or cross-section of the virtual medical device.

In some embodiments, a display object can be projected by identifying or determining which points (e.g., coordinates) of the plane-of-interest are closest (e.g., nearest) to points (e.g., coordinates) of the display object or points of the display object intersecting the display object plane (as described above). Each of the points corresponding to the display object (or the display object plane) can be projected onto the plane-of-interest at the location of the points of the plane-of-interest that were determined to be closest to the identified points of the display object. In some embodiments, projecting can include determining portions of the plane-of-interest that are closest to the display object. The display object can be projected onto those portions of the plane-of-interest that are closest to the display object. In some embodiments, projecting can include determining coordinates of a cross-sectional outline of the display object that are closest to the plane-of-interest.

As a non-limiting example, the ghost display object can be a ghost medical device (for example, a ghost stapler) and the plane-of-interest can be an image plane. The virtual medical device (for example, the virtual stapler) can include a plurality of points on a stapler plane (e.g., a plane corresponding to an axis of the stapler, a plane that bisects the stapler into approximate halves, a plane that is parallel to the image plane, etc.). The system 100 determines which points on the image plane are closest or nearest to the points of the virtual stapler on the stapler plane. The ghost medical device is projected by drawing the points of the virtual medical device onto the determined nearest points of the image plane. In some embodiments, a ghost display object is an outline or other indication of all or a portion of the display object. In some embodiments, the ghost display object is a cross-sectional outline of the display object or a portion thereof. In some embodiments, a ghost display object is a projection of a full or partial representation of the display object. For example, with continued reference to the non-limiting example, the ghost medical device can include a representation of a first limb member, the second limb member, and/or joint member on the image plane.

As a non-limiting example, the ghost display object can be a ghost medical image and the plane-of-interest can be a medical device plane. As mentioned above, the medical device plane can be a plane that bisects the left and right portions (or halves) or top and bottom portions (or halves) of the virtual medical device or portion thereof, such as the joint member. The virtual medical image can include a plurality of points on the image plane. The system 100 determines which points on the medical device plane are closest or nearest to the points of the virtual medical image. The ghost medical image is projected by drawing the points of the virtual medical image onto the determined nearest points of the medical device plane.

As a non-limiting example, the ghost display object is a ghost affected region and the plane-of-interest is an image plane. The affected region can include a plurality of points on a display object plane (for example, a medical device plane, an affected region plane, etc.). The system 100 can determine which points on the image plane are closest or nearest to the points of the affected region on the display object plane. The ghost affected region can be projected by drawing the points from the affected region on the display object plane onto the determined nearest points of the image plane.

In some embodiments, a display object can be projected by determining an arc path and projecting the display object on the plane-of-interest along the arc path. In some embodiments, the system can determine the arc path by first determining an intersection of a display object trajectory and the plane of interest. The system can use the intersection as the center of a sphere and determine an angle between the display object trajectory and plane-of-interest. An arc path can be determined from the angle and each of the points corresponding to the display object (as described above) can then be radially mapped to the plane-of-interest using the arc path. In some embodiments, a distance between each of the points corresponding to the display object and the point of intersection can be determined. In examples such as these, each of the points can then be projected onto the plane-of-interest by placing the points on the plane-of-interest at the same distances they were on the display object plane.

As a non-limiting example, the ghost display object is a ghost medical device and the plane-of-interest is an image plane. The system 100 determines the intersection of the trajectory of the virtual medical device and the image plane. As described above, the virtual medical device can include a plurality of points on the medical device plane. The system 100 determines the distance between the intersection point (i.e., the center of the circle) and each of the plurality points defining the medical device on the medical device plane. The system then projects the points of the medical device onto the image plane at the same distance from the intersection point, but along the image plane.

FIG. 3 illustrates some embodiments of a medical device projected onto an image plane. The ghost medical device 330 can include an outline or other indication of all or a portion of the virtual medical device 302. For example, the system can display a cross-sectional outline of the virtual medical device 302 or a portion thereof. In the illustrated embodiment, the system displays a cross-sectional outline of a side portion of the virtual medical device 302. However, it will be understood that the system can display more, less, or different parts of the medical device. For example, the system can display a projection of a full or partial representation of the first limb member, the second limb member, the limb member, and/or the affected region onto the image plane.

Although FIG. 3 depicts the ghost medical device 330 projected across the entire image plane, in some examples, the ghost medical device 330 is projected on only a portion of the image plane, such as within the medical image. However, it will be understood that the ghost medical device 330 can be projected onto more than a portion of the image plane. Additionally, in some examples, only the affected region or a portion of the affected region is projected onto the plane-of-interest, such as an image plane or medical image, thereby allowing a healthcare provider to see the region of tissue that would be affected if the medical device 302 were positioned on the image plane. However, it will be understood that any portion of the medical device and/or affected region can be project to the plane-of-interest.

In the illustrated embodiment, the system includes trajectory indicators of multiple display objects (e.g., virtual medical device 302 and ghost medical device 330.) For example, FIG. 3 illustrates trajectory indicator 308A and trajectory indicator 308B, which correspond to the first and second limb member, respectively, if the virtual medical device is moved along a projected drive path (e.g., the primary axis.) Similarly, FIG. 3 illustrates trajectory 308C and trajectory 308D corresponding to the ghost first a second limb member, respectively, if the ghost medical device is moved along a projected drive path (e.g., the primary axis of the ghost medical device). It should be noted that a trajectory can be displayed for any display object, including but not limited to a virtual medical device, a ghost medical device, a medical image, a ghost medical image, an affected area, a ghost affected area, etc. In addition, the trajectory can be relative to any axis. In embodiments where a display object has more than one axis, the display can display a trajectory indicator along a primary and/or secondary axis.

Trajectory indicators for ghost display objects can be calculated, determined, and displayed using a variety of techniques. In some embodiments, the trajectory indicators 308C, 308D can be projected onto the plane-of-interest using techniques as described above with respect to projecting a display object onto a plane-of-interest. In some embodiments, the trajectory indicators 308C, 308D can be determined by calculating a trajectory along an axis of the plane-of-interest. In some embodiments, the trajectory indicators 308C, 308D of the ghost medical device 330 correspond to the trajectory indicators 308A, 308B of the medical device 302 such that the trajectory indicators 308C, 308D intersect with trajectory indicators 308A, 308B. In some embodiments, the trajectory indicators 308C, 308D can indicator a trajectory along an axis different than the trajectory axis of the trajectory indicators 308A, 308B such that the trajectory indicators do not intersect. For instance, trajectory indicators 308C, 308D can extend along a secondary axis of the ghost medical device 330 and trajectory indicators 308A, 308B can extend along a primary axis of the virtual medical device 302.

Figure 4:
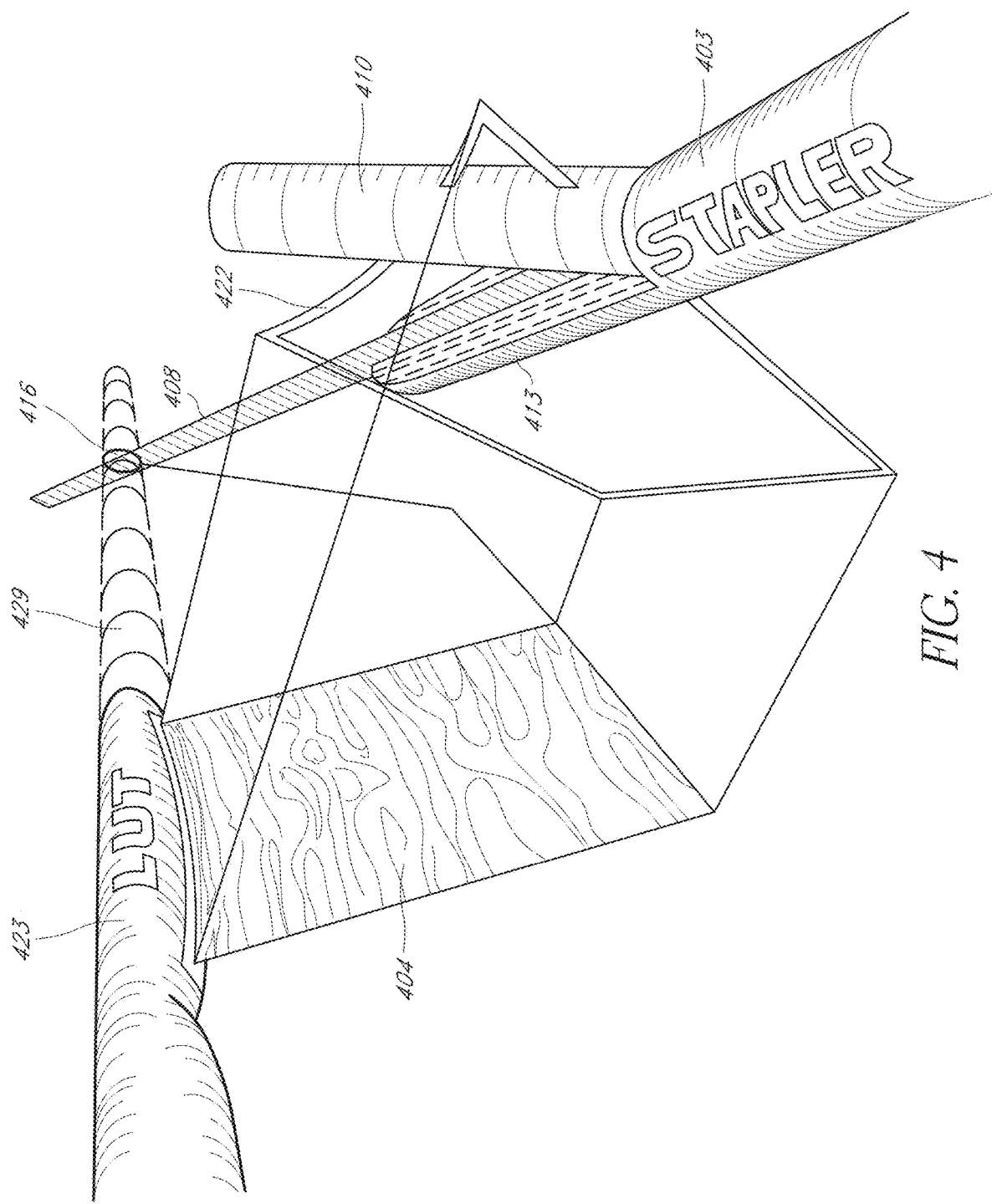
FIG. 4 is a diagram illustrating an embodiment of a rendering of image guidance cues and medical display objects, including a ghost medical image.

FIG. 4 illustrates some embodiments of a medical image (e.g., medical image 304) projected onto a medical device plane. The projected medical image 422 (also referred to as ghost medical image 422) can include an outline or other indication of all or a portion of the medical image 404. For example, the system can display a cross-sectional outline of the medical image 404 or a portion thereof. As a non-limiting, in some instances, the ghost medical image 422 may be projected only within the affected region of the virtual medical device 403. However, it will be understood that the ghost medical image 422 can be displayed in any location relative to the medical device plane. In some examples, the projected medical image 422 can include a cube-shaped representation or a full or partial representation of the medical image. Further, the ghost medical image and/or any other ghost display objects described herein can be displayed in conjunction with any other embodiments described herein.

Intersection Indicators

Referring back to FIG. 2 and as mentioned above, the system can display one or more trajectory indicators 231, 208. For instance, as described above, the system can display trajectory indicator 208 to indicate a trajectory of the medical device 202 along its projected drive path and the system can display trajectory indicator 231 to indicate a trajectory of the ghost display object 230 (e.g., ghost medical device) if moved along its drive path. In some embodiments, because the ghost medical device is a projected version of the virtual medical device, moving the ghost medical device along its projected drive path means moving the virtual medical device along its projected drive path. In some examples, as illustrated in FIG. 4, the system can also display trajectory indicator 429 to indicate a trajectory another medical device 423 (e.g., the ultrasound transducer) if directed along an associated drive path. In some examples, a trajectory of the transecting knife path can also be displayed. As mentioned above, the system can display a trajectory indicator for any medical device or image and along any axis.

In addition to the trajectory indicators, the display 220 can include another image guidance cue in the form of one or more intersection indicators, such as intersection indicator 209 (or intersection indicators 309A, 309B of FIG. 3). The intersection indicators can indicate where one or more portions of the virtual medical device 202 will intersect a plane (for example, the plane corresponding to the medical image 204) if the virtual medical device is moved along an associated drive path and/or where one or more portions or axes of the virtual medical device 202 intersect the plane. In some cases, at the point of intersection 209, the system can display an outline of a portion of the medical device and/or a box or other shape. For example, the system can display a cross-sectional outline of the medical device 202 or a portion thereof. In the illustrated embodiment, the system displays a cross-sectional outline 209 of the lower portion of the medical device 202 and a cross-sectional outline of a knife path 208. However, it will be understood that the system can display more, less, or different parts of the virtual medical device 202. For example, the system can display the upper portion at the point of intersection and display a box around it as well, as desired. Further, additional intersection indicators can be used to show the intersection of one or more trajectories of the virtual medical device and the image plane if the virtual medical device is moved along a different drive path, such as the secondary axis 198C. In addition, trajectory lines can be displayed extending away from the virtual medical device to show where the medical will go if moved forward along its principal or primary axis and/or one or more of the secondary axes. Furthermore, connecting lines 231A, 231B can be drawn from the medical image 204 to the intersection location.

In some examples, the intersection indicator 209 can indicate where the trajectory of the virtual medical device, or trajectory indicator 208, intersects the trajectory of the ghost medical device 230 or trajectory indicator 231. It should be noted that an intersection indicator can be displayed for the intersection of any two or more trajectories or trajectory indicators, or for the intersection of any one or more portions of the virtual medical device with the image plane. For instance, in some examples, as depicted in FIG. 4, the intersection indicator 416 can indicate the intersection between the trajectory of the knife path, or trajectory indicator 408, and the trajectory of the second virtual medical device 423, or trajectory indicator 423.

When data related to two devices or medical devices are displayed with relative emplacement, it can be difficult to orient their relative locations if they do not intersect. In some embodiments, an image guidance system will render relative location information. The relative location information may be shown with color (e.g., objects may be rendered in brighter colors if they are closer), with rendering techniques (e.g., objects may be rendered with transparency so that one object behind another may be visible, but visually appear behind the closer object), with geometry (e.g., a geometric connector may be shown that will allow the viewer to discern the relative relationships), or with any other appropriate technique. For example, in some embodiments, if the intersection indicator is outside of the area of the ultrasound slice, the image guidance system can draw geometry, such as a line (or rectangle) in the plane of the slice to indicate the needle's and medical image's relative positions. In some embodiments, the relative locations could also be represented using vertical and horizontal elements coplanar with the ultrasound or other medical image.

Depicting Affected Region and Other Information

Figure 5:
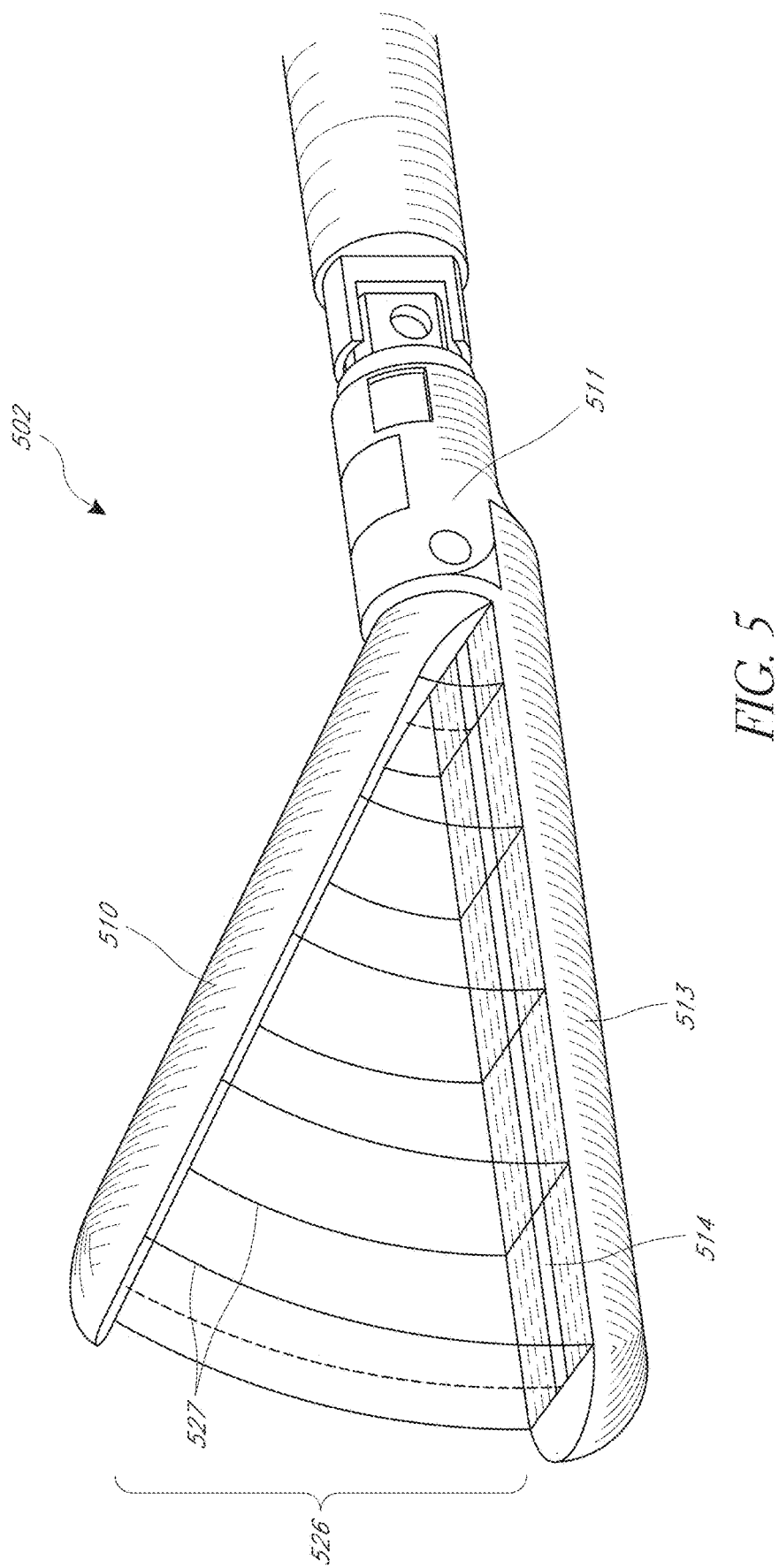
FIG. 5 is a diagram illustrating an embodiment of an affected region associated with a medical device.

Embodiments of the system can include image guidance cues as part of the image guidance data to depict information related to the region or regions that will be affected by the use of medical devices. For example, in some embodiments, an image guidance cue displayed by the image guidance system can include affected region information. The illustrated embodiment of FIG. 5 shows a virtual multi-axis medical device 502 and an additional 3D cue showing the affected region 526 for the multi-axis medical device 502, indicating, for instance, a region of tissue that will be affected when the multi-axis device 502 is activated. In some examples, the affected region can correspond to the inter-jaw area which can be a roughly triangular area with a curved edge, located between the multiple axes.

In some embodiments, the affected region can correspond to the volume located between the two jaws (i.e., the first limb member 513 and the second limb member 510). In some cases, the affected region can be calculated based at least in part on a distance from the hinge. Additional affected sub-regions can be calculated and displayed as well. For example, the plane at which the transecting knife cuts 514 (the line shown in the middle portion of the bottom jaw 513 running generally left to right) can be calculated and shown as well as the one or more planes corresponding to the one or more staples (in the illustrated embodiment, the five lines 527 or bands running transverse to the knife plane.

In some cases, the affected sub-regions can be transverse or perpendicular to each other. For example, an affected knife sub-region can be transverse to an affected staple sub-region. Further, any of the cues described herein can be displayed in conjunction with the aforementioned cues.

In some embodiments, such as when a multi-axis medical device is aimed at the medical image (e.g., a trajectory of the medical device intersects the medical image), the system can display the intersection of the affected region or trajectory of the affected region along a drive path with the medical image (or image plane). Thus, in some embodiments, such as when the medical device is roughly parallel with the image plane (or the medical device trajectory does not intersect with the medical image) the system can project the affected region, or portions thereof, onto the image plane. In examples such as these, the ghost affected region can be a roughly triangular area, which can correspond to the area or volume between the limb members that is projected onto the image plane or medical image. In certain embodiments, such as when the medical device is roughly perpendicular (e.g., with 45 degrees of being perpendicular) to the image plane (or the medical device trajectory intersects with the medical image), the system can display an intersection indicator on the image plane that corresponds to the intersection of the trajectory of the first limb member and the medical image or the intersection of the first limb member with the medical image. In addition, an intersection indicator can be displayed at the intersection of the trajectory of the second limb member and the medical image or the intersection of the second limb member with the medical image.

In some embodiments, the system can use the operating parameters of the medical device 502 and/or measured parameters to determine the affected region (and display the displayed affected region 526). For example, the affected region's size (e.g., girth and length) can be dependent on the length of the first limb member 513, the length of the second limb member 510, the range of movement of the first limb member, the range of movement of the second limb member, etc. These dimensions and operating ranges can be manually entered and/or automatically computed by the guidance system based on device or operating parameters, such as, but not limited to, the medical device make and model, power settings, and the like. Similarly, the system can use measured parameters to determine the affected region, such as, but not limited to, range of motion of the limb member(s), distance between the limb members, available space within the body of the patient, dimensions of tissue to be stapled, etc. For example, in the context of a stapler, the stapler may have a normal range of motion (known as default settings) that can be adjusted based at least in part on the size of the area to be stapled. In some embodiments, the measured parameters can be received in real-time as real-time data. For instance, as distance between the stapler jaws is increased or decreased, the system can display an adjusted affected region. In some examples, the system can use one or more formulas, look-up-tables, fixed or default values, or any other appropriate available information, etc. to determine the affected region.

In addition, the system can determine affected regions prior to operating the medical device and/or during operation of the medical device. For example, prior to operating the medical device, the system can determine one or more affected regions and/or during operation of the medical device, the system can determine one or more dynamic affected regions. In some embodiments, the affected region is static until operation of the medical device and then change as the device is operated. In certain embodiments, the system may rely more on operating parameters of the medical device to determine an initial affected region (i.e., the starting distance between the jaws of the medical device) and measured parameters to determine a dynamic affected region (i.e., as the jaws are opening or closing). However, it will be understood that operating parameters and/or measured parameters can be used to determine the initial affected region and/or the dynamic affected region. In some instance, the medical device 300 is inserted into and/or is moved around inside the patient in a closed or partially closed state in order to reduce the likelihood of causing damage with the medical device. In such examples, the display affected region can correspond to the smaller region located between the first limb member and the second limb member or the displayed affected area can be displayed as if the medical device was fully open.

In some circumstances, the operating parameters, measured parameters, formulas, a look-up-tables, fixed or default values, or other information used to determine the affected regions may include some amount of error or variance. The variance may be due, for instance, to uncertainty regarding the distance between the first limb member 313 and the second limb member 310.

Returning to FIG. 2, the system can also determine the emplacement of the affected region. In some cases, the emplacement of the affected region can be based at least in part on the emplacement of some or all of the corresponding medical device (or virtual medical device), such as medical device 242. For example, the system can receive emplacement data from one or more emplacement sensors associated with the medical device 242 (non-limiting examples: coupled to or integrated with the medical device 242, within an optical path of the medical device, etc.). The system can use the emplacement data to determine the emplacement of the tracked medical device and/or the emplacement of the virtual medical device 202 corresponding to the medical device 242. In some instances, the system can determine the emplacement of the medical device 242 and/or virtual medical device 202 with respect to a point-of-view location.

As yet another example, if the medical device is a stapler and the affected region is a volume located between the first limb member and the second limb member, the emplacement of the affected region can be based at least in part on the emplacement of the stapler (or its virtual version) or at least a portion of it, such as the location(s) on the stapler where the staples are located or portions of the first or second limb members. Specifically, in some embodiments, the affected region can be centered at a location on the medical device, such as the portions on the medical device that move when the medical device is operated. In some examples, if multiple medical devices are used, the posed can be based at least in part on the emplacement of the medical devices.

The system can display the affected region in a variety of ways. Furthermore, although the illustrated embodiment of FIG. 2 includes only one displayed affected region 206, it will be understood that one or more affected regions can be displayed corresponding to each medical device 242 that is displayed on the screen 220 and/or multiple affected regions can be displayed corresponding to a single medical device 242. In some embodiments, the system can display a perspective view of the affected region and/or non-perspective view, such as by displaying the affected region on or with the medical image displayed in the 2D view. Some or all of the affected regions can be displayed as desired. In some embodiments, the portion of the affected region that is displayed can be referred to as the displayed affected.

Although the illustrated embodiment of FIG. 2 refers to the affected region as a volume located between the first limb member and the second limb member, it will be understood that the affected region can correspond to a variety of medical procedures. For example, if a cauterizer is tracked as part of an image guidance system, then the affected region can correspond to a cauterization volume. If a laser is tracked as part of the image guidance system, then the affected region can correspond to a projected laser path. If an ablation needed is tracked as part of the image guidance system, then the affected region can correspond to an ablation volume. Similarly, the affected region can correspond to a biopsy volume, an electroporated volume, cryoablation volume, laser ablation volume, high-frequency focused ultrasound ablation (HIFU) volume, external beam radiation therapy volume, and drilling volume (where the display volume corresponds to the region of bone and other tissue that the manually operated, or computer-controlled drill would remove), depending on the type of medical instrument being used.

As discussed above, in some embodiments, the system 100 projects the affected region (or a portion of the affected region) of the virtual medical device to the image plane or medical image. In some embodiments, the affected region (or a portion of the affected region) is projected onto the plane-of-interest (for example, the image plane) in addition to the ghost medical device. In some embodiments, the affected region (or a portion of the affected region) is projected onto the plane-of-interest without projecting a ghost medical device. In some examples, projecting the ghost medical device and the affected region causes the image plane to be crowded. Thus, projecting only the affected region can make it easier for the physician to see exactly what tissue will be affected. However, it will be understood that more than the affected region can be projected onto the plane-of-interest.

Although FIG. 5 illustrates a multi-axis medical device having two different axes, a multi-axis device can have any number of axes. For example, the multi-axis device can have three, four, five or more axes. As a non-limiting example, the multi-axis medical device can be a three-prong grasper (not shown). The three-prong grasper can have an axis corresponding to each prong and an axis corresponding to its body. In this non-limiting example, the affected region corresponding to the three-prong grasper can include the region between the three prongs, the region corresponding to the volume that will be affected if the prongs are activated, etc.

Tracking a Medical Instrument

Figure 6:
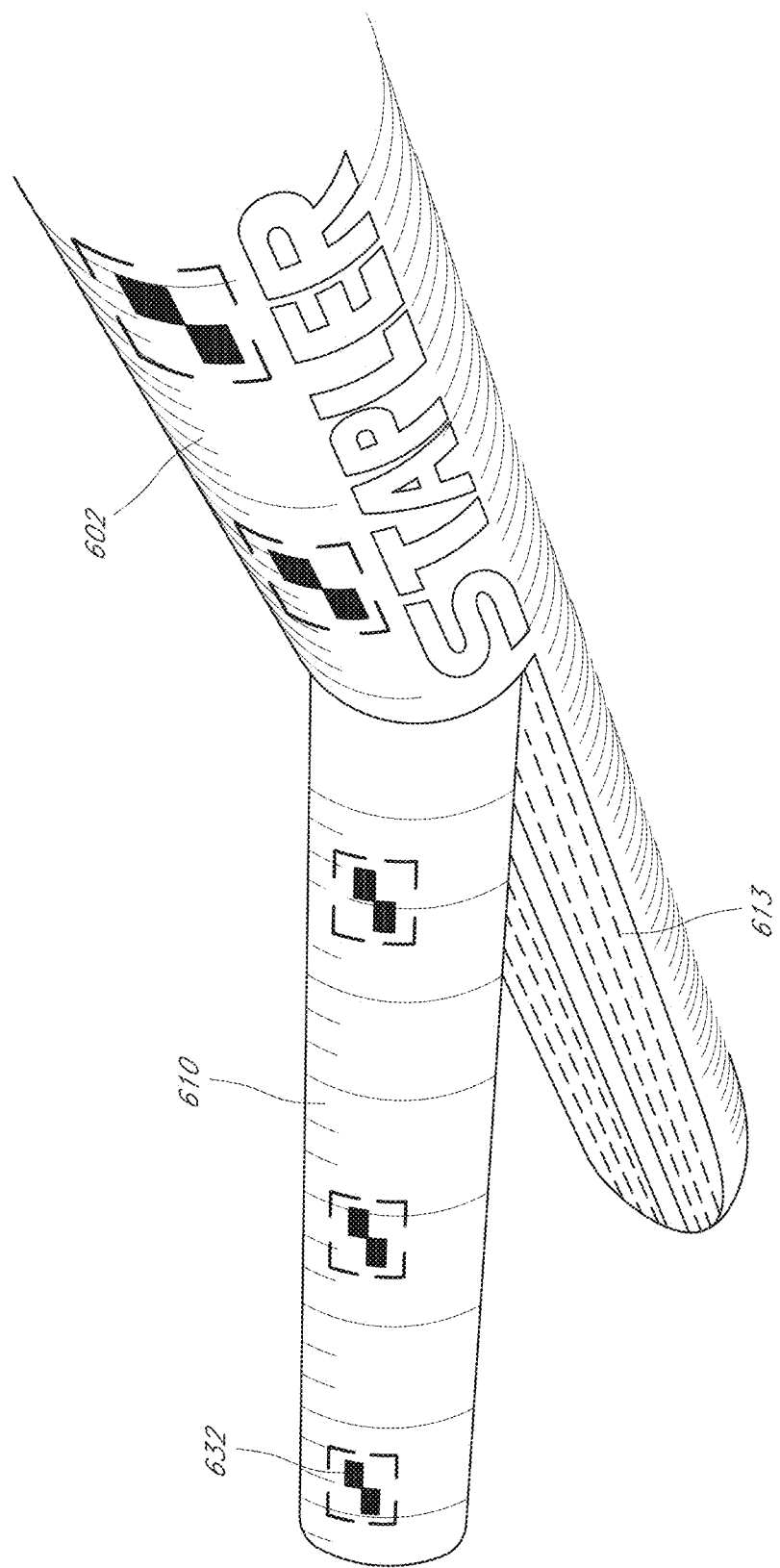
FIG. 6 is a diagram illustrating an embodiment of a medical device having visual tracking fiducials.

FIG. 6 illustrates an embodiment of a displayed medical device 602 having visual tracking fiducials 632. As described above, in some embodiments, the position sensing unit 140 can include an optical tracker and/or the one or more visually-detectable fiducials 632 can be coupled to the one or more medical devices. These markings 632 can be tracked with the optical tracking system using, for instance, laparoscope video. Such marking 632 may be added to any instruments described herein, including but not limited to a transducer, cauterizer, sealer, stapler, transector, resector, grasper, and any other medical device.

It will be understood that the medical device 602 can be tracked in a variety of ways. As shown above, visual tracking fiducials 632 can be placed on different portions of the medical device 602. In some cases, sensors, such as 5 DOF sensors or other sensors can be used. In some embodiments, multiple sensors can be coupled to the medical device 602. For example, one or more sensors can be located on the medical device proximal to the jaw hinge and/or proximal to a second hinge (e.g., second hinge 1028 shown in FIG. 10), and/or one or more sensors can be coupled to a lower portion and/or the upper portion of the first and/or second limb member.

As described above, in some examples, a medical device 602 can also have markings such as bands around the shaft or jaws, for example, to indicate distance along the shaft or jaws. Healthcare providers performing medical device procedures are often familiar with these markings and can use them to help understand the spatial relationship between the medical device and anatomy. In some embodiments, the make and model of the medical device is known to the image guidance system and the virtual medical device 602 displayed in display 220 can resemble medical device 242. The features of medical devices that can be rendered in the scene include the overall shape (diameter, angles, cross sectional shape, curvature, etc.), color, distance markers, angle of the jaws, visuals or echogenic fiduciary markers, the state of deployable elements such as tines, paddles, anchors, resection loops, stiffening or steerable sleeves, temperature, radiation, light or magnetic field sensors, lens, waveguides, fluid transfer channels, and the like.

In addition, the system can use a switch, sensor, or button or other mechanism to determine when the jaw has been closed. For example, a switch or sensor can be near the handle or other actuator used to close the jaw. Once activated, the system can update the virtual display to show that the jaw has been closed. In some examples, as described above, jaw open or closure and distance between the jaws can be operating parameters of the medical device that are used to display the virtual medical device.

Figure 7:
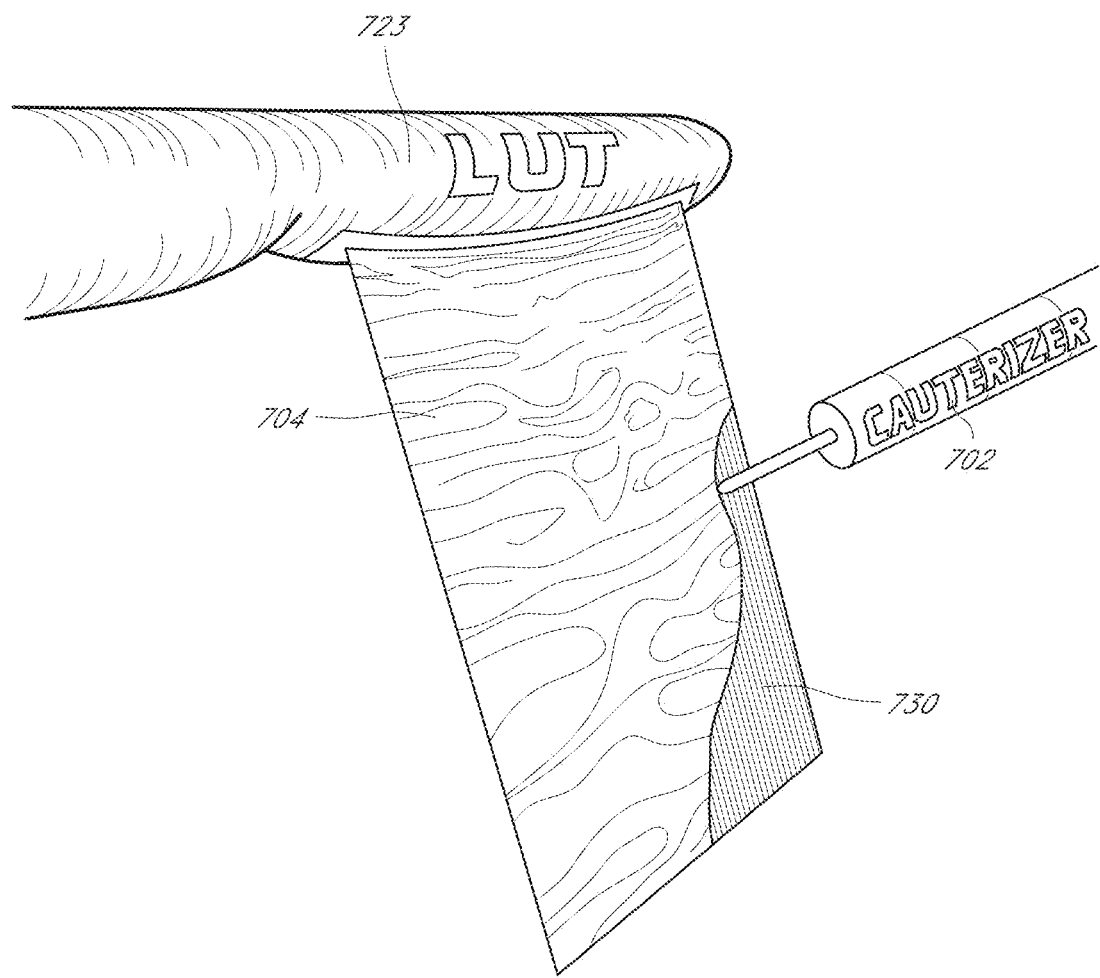
FIG. 7 is a diagram illustrating an embodiment of a rendering of a first and second virtual medical device and a medical image.

In some instances, a first medical device can be used to mark a path for a second medical instrument. Accordingly, the system 100 can track the first medical device such that the system can display the marked path for the second medical device. FIG. 7 illustrates an example of tracking a first medical device (e.g., a cauterizing device 702) which is used to cauterize (or mark) a path (e.g., a stapling, transecting, resecting, grasping path). In this example, the navigation software can assist the physician to cauterize (or mark) tissue while inspecting the medical image relative to the tip of the cauterizing device. While using the medical image for guidance, the cauterizing device 702 and/or tip of the cauterizing device can be tracked and subsequently used as guidance for a second medical device (e.g., a stapler).

Any of the navigation features and/or guidance cues can also be used for with the cauterizing device 730. For instance, the cauterizing device 730 can have associated trajectory indicators, shadow bars, ghost cauterizing device, projections, tip-to-plane distance markers, and any other guidance cues as described herein.

Medical Image can Traverse the Affected Region

In some embodiments, the medical image 804 can traverse the affected region 826 of the medical device 802. In such cases, the system 100 can determine and display a point or area of intersection of the affected region 826 with the medical image 804.

Figure 8:
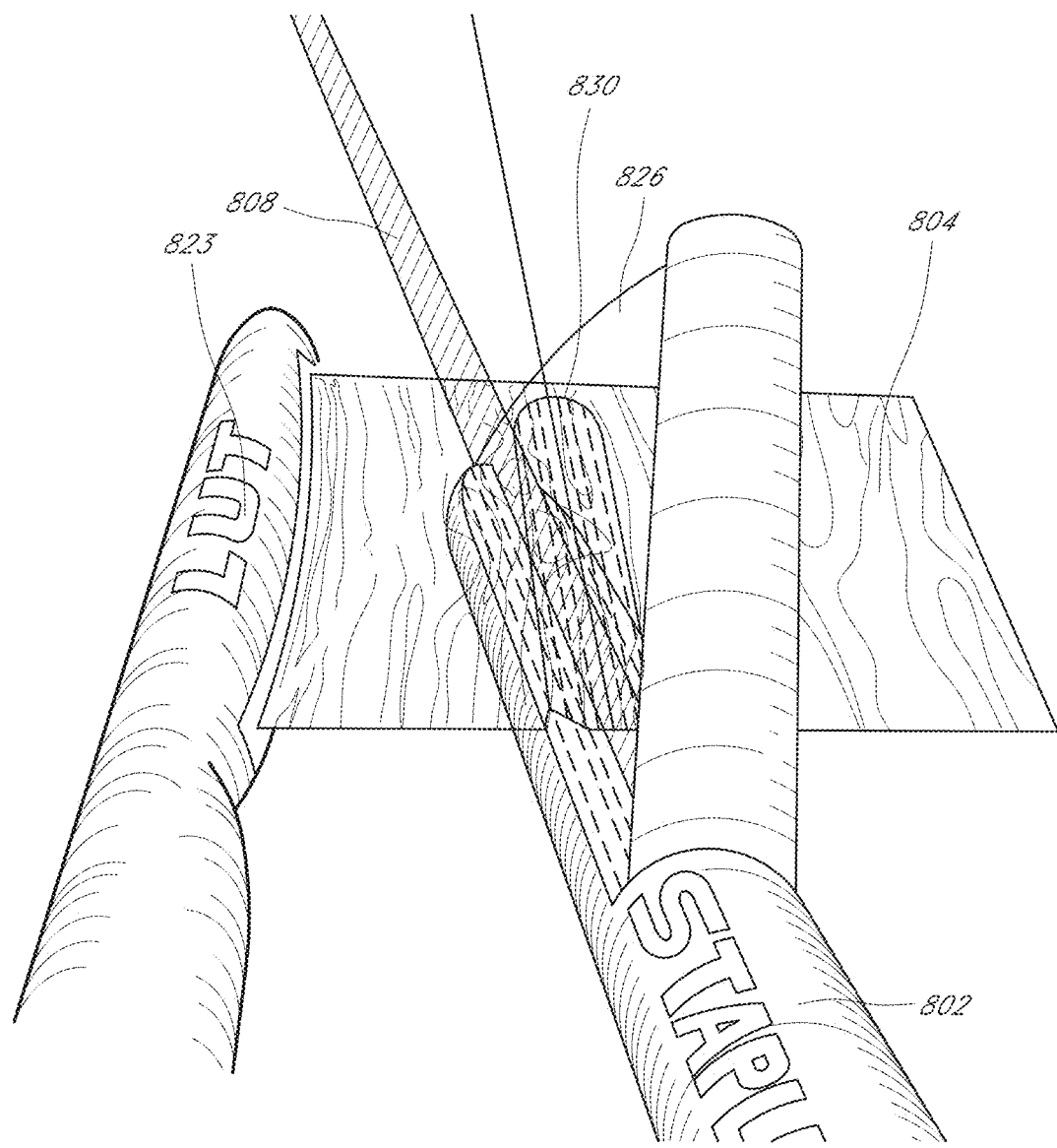
FIG. 8 is a diagram illustrating an embodiment of a rendering first and second virtual medical device.

In some examples, the system 100 can determine and display a point of area of intersection between a plane (for example, an image plane) or image area and an affected region 826. As shown in FIG. 8, an intersection indicator 830 can be projected onto the image plane and/or medical image 804 to illustrate the location on the medical image 804 that the stapler will intersect if the stapler is activated (e.g., closed). In some examples, the depicted intersection indicator can appear like a schematic of the multi-axis device superimposed onto the image plane. In other examples, the intersection indicator 830 can be markings such as the guidance cues described above. Using the intersection indicator 830, the healthcare provider can identify where a medical device will intersect a plane (e.g., the image plane) if the stapler is operated.

Combining an Ultrasound Probe with a Two-Jaw Instrument

In some embodiments, an ultrasound transducer (for example, a miniature ultrasound transducer) can be integrated with a multi-axis instrument such as a transecting stapler, grasper, or vessel sealer. A physician may use the integrated ultrasound transducer and jawed instrument to ensure that the physician can view, in ultrasound, the internal tissue structures before they are stapled, transected, resected, sealed, or grasped, thereby helping the physician avoid critical structures (such as blood vessels). As described above, a 3D viewing area can include perspective views of each of a virtual integrated device, a medical image, navigation cues (e.g. affected region as shown in FIG. 5) or other cues described herein. In some examples, the integrated device can include one or more sensors located at different locations on the device. For example, a sensor can be embedded inside, or affixed to one or more of the joint member, the first limb member, the second limb member, and the ultrasound transducer (such as at the tip, along the shaft, or on a handle). Furthermore, the system can use the known configuration of the device to determine the proper location between the affected region and the medical image for display purposes.

Figure 9:
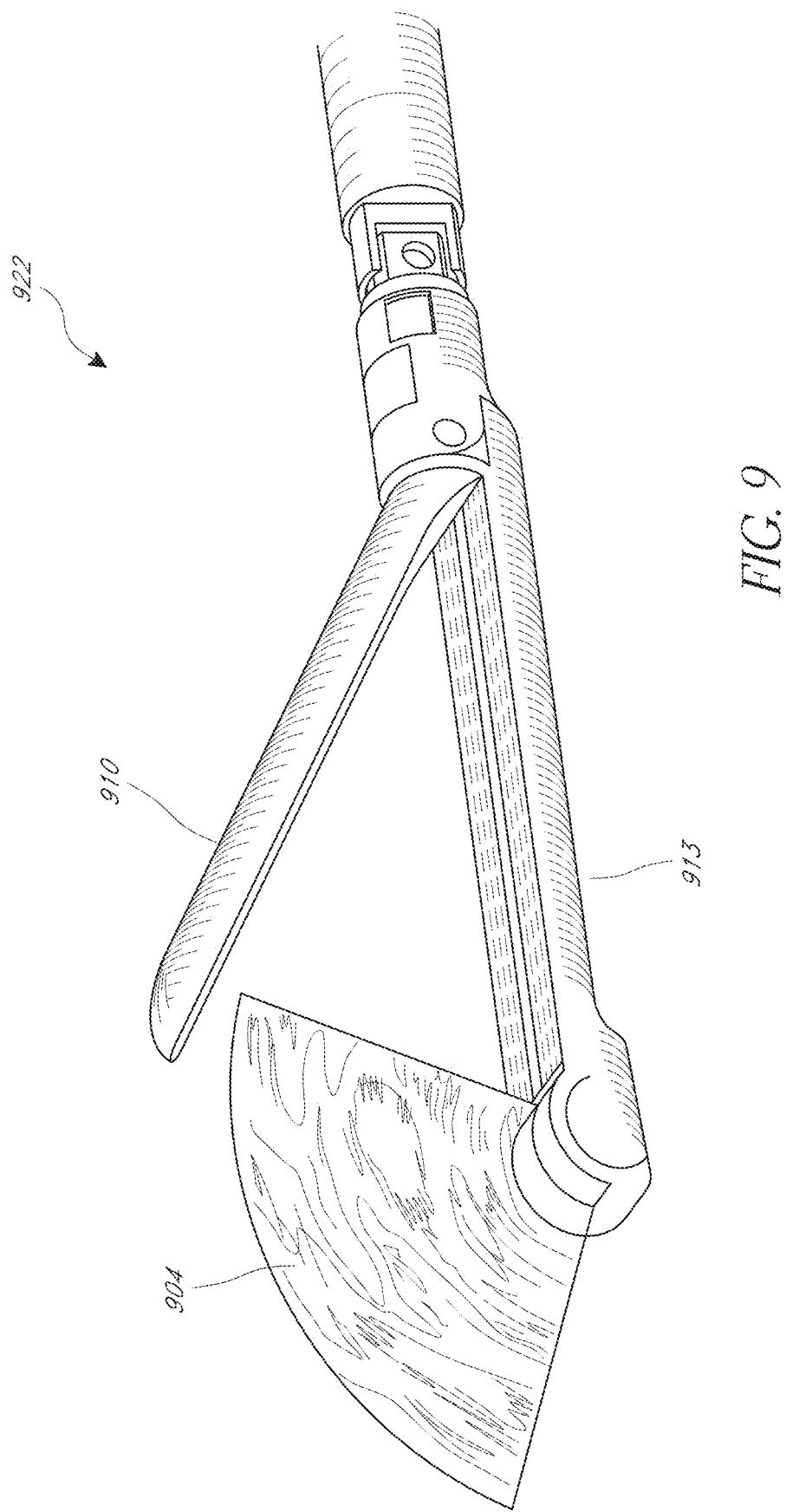
FIG. 9 is a diagram illustrating an embodiment of a medical device having an integrated imaging device.

FIG. 9 is a diagram illustrating an embodiment of a transducer mounted at the tip of the multi-axis instrument 922 such that the scan plane coincides with the inter-jaw plane. This is an elegant way to unify the two areas of interest mentioned previously so that both tissue inspection and tissue-affecting action (such as transection, stapling, resection, or grasping) take place in a single plane. As described above, a 3D viewing area can include perspective views of each at least a portion of the medical image 904, at least a portion of the integrated device 922 (for example, the first limb member 913, the second limb member 910, and/or the ultrasound transducer), a displayed affected region (not shown), and other image guidance cues (not shown).

Although FIG. 9 illustrates the transducer mounted to the tip of the first limb member, the transducer can be mounted anywhere on the medical device. For example, the transducer can be mounted to the second limb member 910 (such as at the tip, along the body, or near the hinge), the first limb member 913 (such as at the tip, along the body, or near the hinge), or the joint member (such as at the tip, along the body, or near/on the hinge).

FIG. 10 illustrates an embodiment of an ultrasound transducer mounted to a multi-axis instrument. In the illustrated embodiment of FIG. 10, the integrated device 1022 includes a transverse-mounted ultrasound transducer. The scanning plane of the transducer can be perpendicular to the path of the transecting knife, the stapler axis (i.e., the joint member axis), and/or the first member axis (i.e., the first axis). The scanning plane of the transducer can also be perpendicular or parallel to the affected staple sub-regions (as described above).

Figure 11:
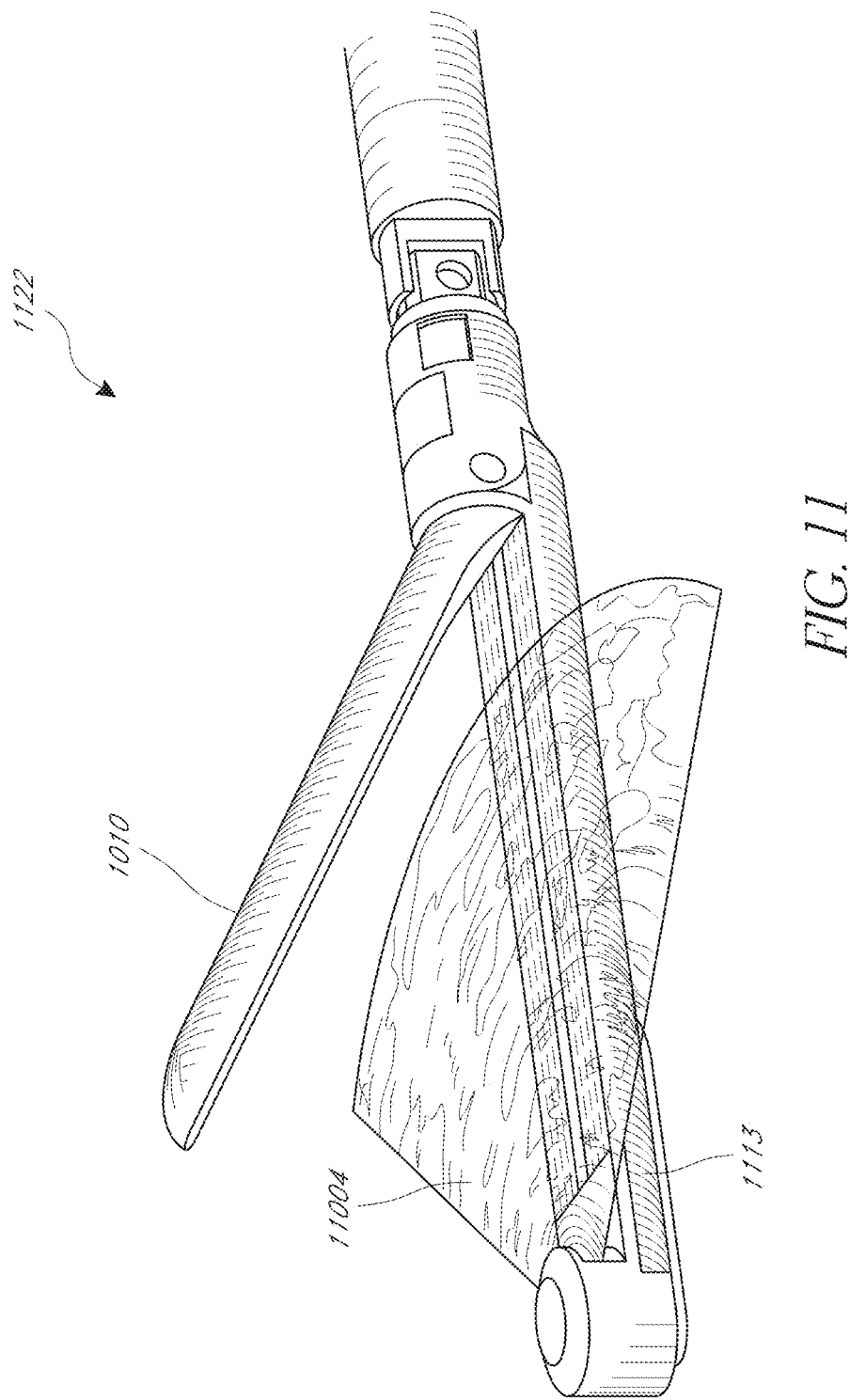
FIG. 11 is a diagram illustrating an embodiment of a medical device having an integrated imaging device.

FIG. 11 illustrates an embodiment of an ultrasound transducer mounted to a multi-axis instrument. In illustrated embodiment of FIG. 11, the integrated device 1122 shows an ultrasound transducer mounted parallel to the rigid stapler surface and scanning "backwards." This design attempts to provide better imaging of the area located exactly between the jaws at the moment of stapling, transecting, resecting, sealing, or grasping.

Figure 12:
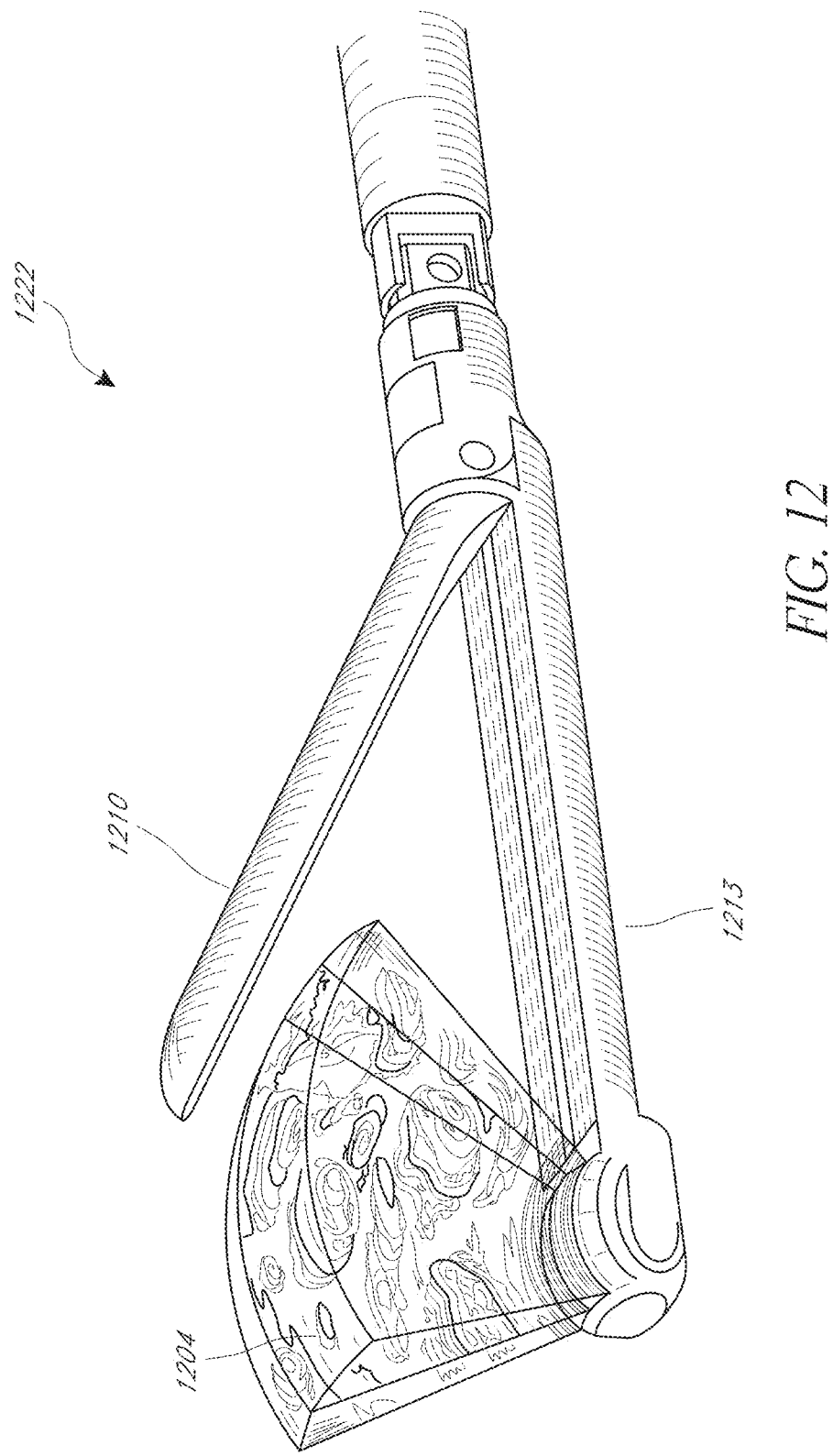
FIG. 12 is a diagram illustrating an embodiment of a medical device having an integrated imaging device.

FIG. 12 illustrates an embodiment of an ultrasound transducer mounted to a multi-axis instrument. In illustrated embodiment of FIG. 12, a 2D phased array miniature transducer is integrated with a multi-axis instrument. The integrated device 1222 can scan a volumetric tissue area between the limb members 1210, 1213. A volumetric rendering method or conventional volume rendering could be used for real-time visualization during stapler guidance. It should be noted that the 2D phased array miniature transducer can be utilized in any of the previous examples.

It will be understood that the ultrasound transducer can be integrated with the medical device in a variety of ways and that FIGS. 9-12 provide non-limiting examples. Further, the transducers can cover a variety of angles. They can be attached to any portion of the multi-axis instrument (such as either the first limb member or the second limb member) and angled differently than shown. In addition, 2D phased arrays can be flat and thus integrate more seamlessly with tool designs than shown, avoiding local tissue displacement at the transducing element.

Flow Diagrams

Figure 13:
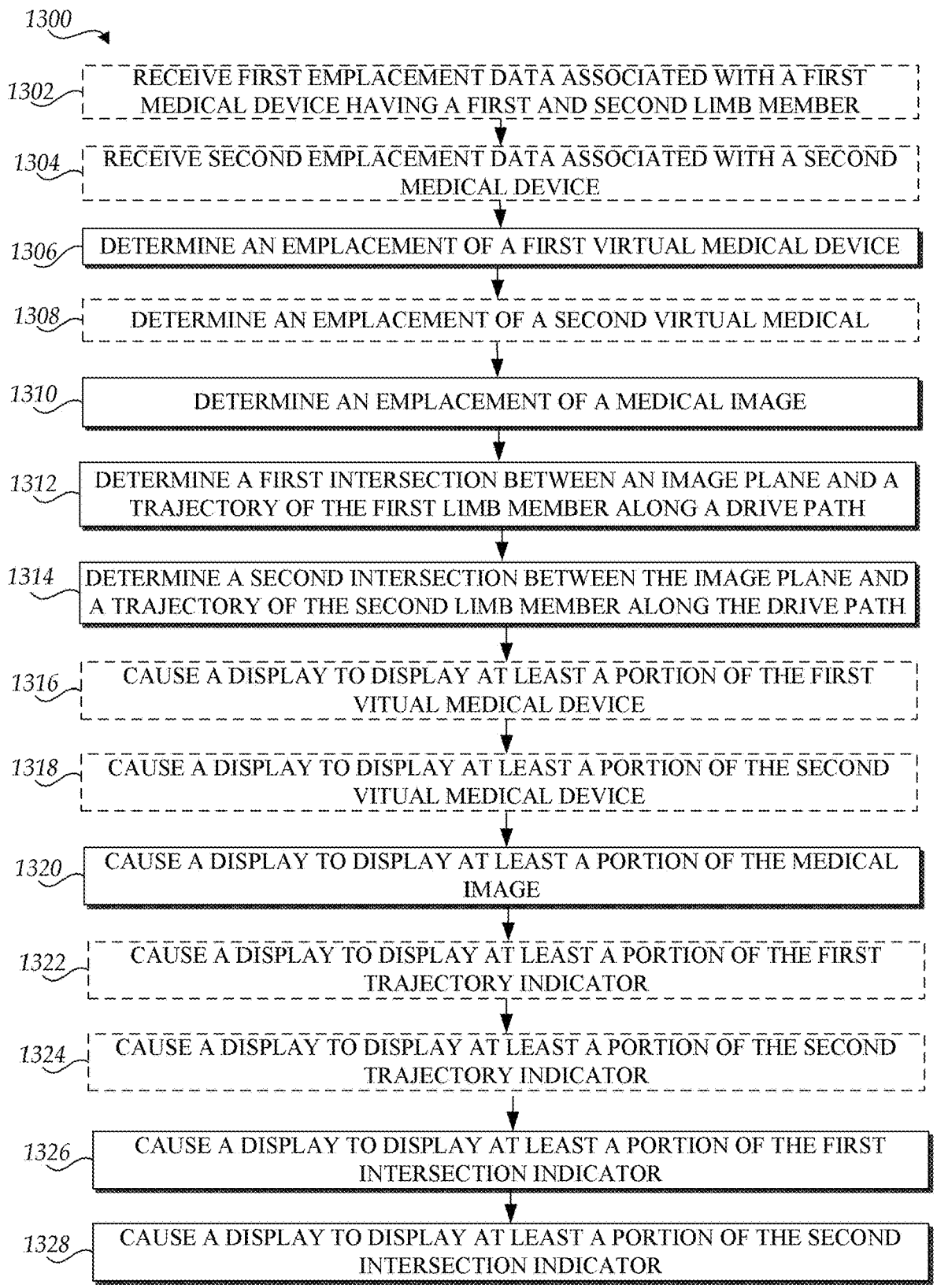
FIG. 13 is a flow diagram illustrative of an embodiment of a routine implemented by the system to determine and cause a display to display one or more intersection indicators corresponding to an intersection between a plane-of-interest and one or more trajectories of a medical device.

FIG. 13 is a flow diagram illustrative of an embodiment of a routine implemented by the system to determine and cause a display to display one or more intersection indicators corresponding to an intersection between a plane-of-interest and one or more trajectories of a medical device. One skilled in the relevant art will appreciate that the elements outlined for routine 1300 can be implemented by one or more computing devices/components that are associated with the system 100, such as the position sensing unit 140, the image guidance unit 130, surgical system 149, an HMD, and/or the imager 150. Accordingly, routine 1300 has been logically associated as being generally performed by the system 100. However, the following illustrative embodiment should not be construed as limiting. Furthermore, it will be understood that the various blocks described herein with reference to FIG. 13 can be implemented in a variety of orders. For example, the system 100 can implement some blocks concurrently or change the order as desired. Furthermore, it will be understood that fewer, more, or different blocks can be used as part of the routine 1300. For example, in some embodiments, the solid blocks are part of routine 1300 and the dotted blocks are not implemented. However, it will be understood that any of the blocks (and more or different blocks) can be implemented as part of routine 1300.

At block 1302, the system 100 receives first emplacement data associated with a first emplacement sensor and/or a first medical device. The first emplacement data can be generated by the first emplacement sensor and/or by a position sensing unit. In some embodiments, the first emplacement sensor can be associated with the first medical device. For example, the first emplacement sensor can be associated with and/or attached to an ultrasound transducer, as described above. In some embodiments, the first medical device is a multi-axis medical device. Furthermore, the first medical device has a joint member having a joint member axis, a first limb member having a first axis, and a second limb member having a second axis that is different from the joint member axis and the first axis. As described above, one or more emplacement sensors can be associated with a first limb member, a second limb member, and/or a joint member of the associated first medical device. The system can receive emplacement data from each of these emplacement sensors.

At block 1304, the system 100 receives second emplacement data associated with a second emplacement sensor and/or a second medical device. The second emplacement data can be generated by the second emplacement sensor and/or by a position sensing unit. In some embodiments, the second emplacement sensor can be associated with the second medical device. For example, the second emplacement sensor can be associated with and/or attached to a stapler, as described above with respect to FIGS. 9-12. In some embodiments, the second medical device is an imaging device such as an ultrasound transducer.

At block 1306, the system 100 can determine an emplacement of a first virtual medical device based at least in part on the received first emplacement data. As described above, the first virtual medical device can correspond to a multi-axis device such as a transecting stapler, grasper, or vessel sealer. In some embodiments, the virtual medical device corresponds to a single-axis device such as an ablation probe.

In some embodiments, the system 100 can use the first emplacement data and one or more characteristics of the associated first medical device (or a corresponding virtual medical device) to determine the emplacement of at least a portion of the first medical device. For example, the at least a portion of the first medical device can include a portion the first limb member, a portion of the second limb member, or a portion of the joint member. As a non-limiting example, the characteristics of the associated first medical device may indicate an emplacement of the second limb member relative to the associated first medical device.

Using the received emplacement data, the system 100 can determine the emplacement of the first medical device, for example, relative to known location of emplacement sensor(s) on the first medical device. For example, the system 100 can use a known relationship between the first emplacement data and the emplacement of the medical device (non-limiting example: the second limb member extends 8 cm. away from the hinge at a 45 degree angle relative to the first limb member) and/or use a known relationship between the emplacement of the emplacement sensor(s) and/or associated medical device (or virtual medical device) and the emplacement of the medical device (non-limiting examples: the first limb member begins 4 cm. from the tip of the first medical device (or first virtual medical device) and ends at the hinge of the first medical device (or first virtual medical device), or the first limb member extends 4 cm. in either direction from the ends of one of the emplacement sensors).

In addition, in certain embodiments, the system 100 can determine the emplacement of the first medical device in one or more coordinate systems by mapping the first emplacement data, from one coordinate system to a second coordinate system. For example, the first emplacement data may be received with respect to a first coordinate system, such as a position sensing coordinate system, and then mapped to a second coordinate system, such as a 3D scene coordinate system and/or a screen coordinate system. The emplacement of the first medical device can be determined with respect to one or more of the coordinate systems. For example, the emplacement of the first medical device can be determined after the first emplacement data has been mapped to the second coordinate system, such as the 3D scene coordinate system and/or the screen coordinate system, or the emplacement of the first medical device can be determined for the first coordinate system, such as the position sensing coordinate system, and then mapped to the 3D scene coordinate system and/or the screen coordinate system.

In certain embodiments, the system 100 can also use point-of-view location (e.g., the location of the point-of-view for viewing the 3D space) to determine the emplacement of the first medical device for viewing. In some embodiments, as described in greater detail in '933 Application, the point-of-view location can be a fixed location, such as a predetermined distance/angle from the screen 220 or stand 170 and or a location configured by the user; or the point-of-view location can by dynamic. For example, the system can track a user in real-time and determine the point-of-view location based at least in part on the tracked location of the user.

In certain embodiments, the system 100 can also use an offset to determine the emplacement of the first virtual medical device for viewing. For example, the system 100 can determine an initial emplacement of the first medical device in the 3D scene coordinate system and/or the screen coordinate system, and then apply an offset to the initial emplacement and/or the system 100 can determine an initial emplacement of the first medical device in the position sensing coordinate system and apply an offset to the initial emplacement prior to mapping the emplacement of the first medical device in the position sensing coordinate system to the 3D scene coordinate system and/or the screen coordinate system.

The offset can be made in one, or a combination of, coordinate systems, and/or with respect to one, or a combination of, axes. In certain embodiments, the offset can be made along a y-axis (up/down) of the position sensing coordinate system, the 3D scene coordinate system and/or the screen coordinate system. For example, the system 100 can adjust the y-coordinate (up/down coordinate) of the determined emplacement of the first medical device (or the first emplacement sensor(s)) in the position sensing coordinate system by the offset amount. When mapped to the 3D scene coordinate system and/or the screen coordinate system, the system 100 can use the adjusted emplacement. As yet another example, the system 100 can adjust the y-coordinate (up/down coordinate) of the determined emplacement of the first medical device (or the first emplacement sensor(s)) in the 3D scene coordinate system and/or the screen coordinate system by the offset amount. Any combination of the above-referenced examples can be used as desired. Furthermore, it will be understood that the offset can be made in any one or any combinations of the coordinate systems and with reference to any one or any combination of the axes. For example, the adjustment can be made along any one or any combination of the x-axis, y-axis, or z-axis.

Furthermore, the offset can be a predetermined offset and/or a dynamic offset. In some embodiments, a predetermined offset can be used. For example, the system 100 can use a static offset based on an average height of males and/or females or average distance between elbows and hands, the height of the user, a distance between the user's elbow and eyes, expected location of a user with respect to the imaged volume, etc. In certain embodiments, the system 100 can use a dynamic offset, such as a determined emplacement of an HMD relative to one or more emplacement sensors, position sensing region, and/or position sensing unit coordinate system. For example, the system 100 can determine the emplacement of an HMD relative to a medical device or imaged area and adjust the offset such that the medical image is always in view on the displays of an HMD. With continued reference to the example, if the wearer crouches down or turns to the side, the system 100 can determine the change in relative emplacement between the HMD and the medical device or imaged area and adjust the offset such that the medical image remains in view in substantially the same emplacement.

In addition, it will be understood that the offset described herein with reference to the first medical device can be applied to any one or any combination of the objects to be displayed and/or to all contents of the virtual 3D scene. In some embodiments, the offset can be applied to some objects to be displayed but not others.

At block 1308, the system 100 can determine an emplacement of a second virtual medical device based at least in part on the received second emplacement data. As described above, the second virtual medical device can correspond to an imaging device such as an ultrasound transducer. The emplacement of the second virtual medical device can be determined in a similar manner as described with respect to the first medical device at block 1306.

At block 1310, the system 100 determines an emplacement of a medical image (e.g., medical image) based at least in part on received second emplacement data. The medical image can be an intra-operative and/or real-time medical image, such as a live ultrasound or intra-operative CT scan, or can be a pre-operative image, such as a pre-operative CT or MRI scan image. A real-time medical image (or real-time medical imaging stream) can refer to a medical image (or real-time medical imaging stream) received in real-time. The medical image received in real-time can correspond to a live image, such as a live medical image generated by an ultrasound or other image, such as a pre-operative or intra-operative CT image or MRI image that is communicated in real-time.

In some embodiments, the system 100 can use the second emplacement data and one or more characteristics of the second emplacement sensor or associated second medical device (or a corresponding second virtual medical device) to determine the emplacement of the medical image. For example, the characteristics may indicate an emplacement of the medical image relative to the second emplacement sensor or associated second medical device (or second virtual medical imaging device).

Using this information, the system 100 can determine the emplacement of the medical image relative to the second emplacement sensor and/or associated second medical device (or second virtual medical imaging device). For example, the system 100 can use a known relationship between the second emplacement data and the emplacement of the medical image (non-limiting example: the medical image begins 2 cm. away from the of the second emplacement data location in a particular direction and ends 5 cm. away) and/or use a known relationship between the emplacement of the second emplacement sensor and/or associated second medical device (or second virtual medical imaging device) and the emplacement of the medical image (non-limiting examples: the medical image begins 4 cm. from the tip of the second medical device (or second virtual medical imaging device) and ends at the tip of the second medical device (or second virtual medical imaging device), or the medical image extends 2 cm. in either direction from the ends of the second emplacement sensor).

In addition, in certain embodiments, the system 100 can determine the emplacement of the medical image in one or more coordinate systems by mapping the first emplacement data, from one coordinate system to a second coordinate system. For example, the second emplacement data may be received with respect to a first coordinate system, such as a position sensing coordinate system, and then mapped to a second coordinate system, such as a 3D scene coordinate system and/or a screen coordinate system. The emplacement of the medical image can be determined with respect to one or more of the coordinate systems. For example, the emplacement of the medical image can be determined after the second emplacement data has been mapped to the second coordinate system, such as the 3D scene coordinate system and/or the screen coordinate system, or the emplacement of the medical image can be determined for the first coordinate system, such as the position sensing coordinate system, and then mapped to the 3D scene coordinate system and/or the screen coordinate system.

In certain embodiments, the system 100 can also use point-of-view location (e.g., the location of the point-of-view for viewing the 3D space) to determine the emplacement of the medical image for viewing. In some embodiments, as described in greater detail in '933 Application, the point-of-view location can be a fixed location, such as a predetermined distance/angle from the screen 220 or stand 170 and or a location configured by the user; or the point-of-view location can by dynamic. For example, the system can track a user in real-time and determine the point-of-view location based at least in part on the tracked location of the user.

As described above with respect to block 1306, in certain embodiments, the system 100 can also use an offset to determine the emplacement of the medical image for viewing. For example, the system 100 can determine an initial emplacement of the medical image in the 3D scene coordinate system and/or the screen coordinate system, and then apply an offset to the initial emplacement and/or the system 100 can determine an initial emplacement of the medical image in the position sensing coordinate system and apply an offset to the initial emplacement prior to mapping the emplacement of the medical image in the position sensing coordinate system to the 3D scene coordinate system and/or the screen coordinate system.

The offset can be made in one, or a combination of, coordinate systems, and/or with respect to one, or a combination of, axes. In certain embodiments, the offset can be made along a y-axis (up/down) of the position sensing coordinate system, the 3D scene coordinate system and/or the screen coordinate system. For example, the system 100 can adjust the y-coordinate (up/down coordinate) of the determined emplacement of the medical image (or the first emplacement sensor) in the position sensing coordinate system by the offset amount. When mapped to the 3D scene coordinate system and/or the screen coordinate system, the system 100 can use the adjusted emplacement. As yet another example, the system 100 can adjust the y-coordinate (up/down coordinate) of the determined emplacement of the medical image (or the first emplacement sensor) in the 3D scene coordinate system and/or the screen coordinate system by the offset amount. Any combination of the above-referenced examples can be used as desired. Furthermore, it will be understood that the offset can be made in any one or any combinations of the coordinate systems and with reference to any one or any combination of the axes. For example, the adjustment can be made along any one or any combination of the x-axis, y-axis, or z-axis.

Furthermore, the offset can be a predetermined offset and/or a dynamic offset. In some embodiments, a predetermined offset can be used. For example, the system 100 can use a static offset based on an average height of males and/or females or average distance between elbows and hands, the height of the user, a distance between the user's elbow and eyes, expected location of a user with respect to the imaged volume, etc. In certain embodiments, the system 100 can use a dynamic offset, such as a determined emplacement of an HMD relative to one or more emplacement sensors, position sensing region, and/or position sensing unit coordinate system. For example, the system 100 can determine the emplacement of an HMD relative to a medical device or imaged area and adjust the offset such that the medical image is always in view on the displays of an HMD. With continued reference to the example, if the wearer crouches down or turns to the side, the system 100 can determine the change in relative emplacement between the HMD and the medical device or imaged area and adjust the offset such that the medical image remains in view in substantially the same emplacement.

In addition, it will be understood that the offset described herein with reference to the medical image can be applied to any one or any combination of the objects to be displayed and/or to all contents of the virtual 3D scene. In some embodiments, the offset can be applied to some objects to be displayed but not others.

At block 1312, the system 100 can determine a first intersection between an image plane and a trajectory of the first limb member along a drive path. As described above with respect to FIGS. 2 and 3, a trajectory can be calculated, determined, and displayed for the first limb member 213, the second limb member 210 and/or the joint member 211. For example, each of the trajectories can be calculated based on a drive path for the medical device. With respect to the first limb member, the trajectory can correspond to the path that the first limb member will follow if the medical device is moved along the drive path.

In some examples, trajectory indicators can indicate a trajectory along an axis that is different from and parallel to the primary axis (non-limiting example: an axis corresponding to a distal portion of the first limb member along the drive path). In addition, the trajectory indicators can extend through a distal portion (e.g., the tip) of the medical device (e.g., a distal portion of the first limb member.

The first intersection indicator can indicate where the first limb member of the first virtual medical device will intersect the image plane (e.g., the plane corresponding to the medical image) if the virtual medical device is moved along an associated drive path and/or where one or more portions or axes of the first virtual medical device intersect the image plane. As described above, the drive path can be predetermined or dynamic.

At block 1314, the system 100 can determine a second intersection between an image plane and a trajectory of the second limb member along the drive path. The second intersection indicator can be determined using the same techniques as described above and described with respect to block 1312. With respect to the second limb member, the trajectory can correspond to the path that the second limb member will follow if the medical device is moved along the drive path. In some embodiments, the trajectory (e.g., the trajectory indicators) can extend through a distal portion (e.g., the tip) of the medical device (e.g., a distal portion of the second limb member.)

The second intersection indicator can indicate where the second limb member of the first virtual medical device will intersect the image plane (e.g., the plane corresponding to the medical image) if the first virtual medical device is moved along an associated drive path and/or where one or more portions or axes of the first virtual medical device intersect the image plane.

As described in greater detail above with reference to FIGS. 2 and 3, the system 100 can determine the points of intersection between one or more trajectories and/or trajectory indicators, one or more axes (or portions) of one or more display objects (for example, a virtual medical device, a ghost display object, an affected region, etc.) and/or one or more planes (e.g., the virtual medical device plane, the image plane, etc.) based on the emplacement information of one or more medical devices.

In a non-limiting example, one or more intersection indicators can be determined and displayed for an intersection between a trajectory of a medical device (for example, a trajectory of the first limb member of a stapler) and a plane-of-interest (for example, an image plane). One or more intersection indicators can also be displayed for an intersection between a trajectory of the second limb member along a drive path (for example, an axis parallel to the primary axis and intersecting the second limb member) and a plane-of-interest (for example, an image plane).

In a non-limiting example, one or more intersection indicators can be displayed for an intersection between a trajectory of a medical device (for example, a stapler, an ultrasound transducer, medical imaging device, etc.) and an affected region (or trajectory of an affected region)

In a non-limiting example, one or more intersection indicators can be displayed for an intersection between a trajectory of a medical device (for example, a stapler, an ultrasound transducer, medical imaging device, etc.) and an axis, trajectory, or plane of a transecting knife.

In a non-limiting example, one or more intersection indicators can be displayed for an intersection between a trajectory of a ghost display object (for example, a ghost medical device, a ghost affected region, a ghost medical image, etc.), a stapler, an ultrasound transducer, medical imaging device, etc., and an a trajectory of another display object (for example, a medical device, an affected region, a medical image, etc.).

At block 1316, the system 100 can cause a display to display a view of a virtual 3D scene including a perspective rendering of at least a portion of the first virtual medical device based at least in part on the determined emplacement of the first virtual medical device. In some embodiments, the 3D rendering of the at least a portion of the first virtual medical device includes at least a portion of the first limb member and at least a portion of the second limb member. However, it will be understood that the 3D rendering of the at least a portion of the first virtual medical device can include any portions of the first virtual device.

As described above, the perspective view or rendering the medical image can be determined and displayed based at least in part on a point-of-view location. The point-of-view location can be a fixed point-of-view location or a dynamic point-of-view location. For example, the point-of-view location can be with respect to a set location in front of the display and/or can be based on a tracked location of the display, the HMD, or the user. In some embodiments, the point-of-view location is determined based at least in part on the relative emplacement of an HMD or user with respect to the position sensing region or imaged volume, or the emplacement of an HMD within a position sensing coordinate system. In embodiments, in which the point-of-view location is based on a tracked location, the system 100 can enable the user to view different perspective views of the virtual 3D scene based on the changing emplacement of the tracked object (HMD, user) relative to the medical devices 145, 155 or the position sensing region.

In certain embodiments, the system 100 can determine multiple emplacements for the first virtual medical device. For example, the system 100 can determine the emplacement for the medical image for a right-eye view and a left-eye view of a stereoscopic display, such for a HMD. In this way, each display for the HMD can display the medical image from a slightly different perspective corresponding to a right-eye view and a left-eye view, etc.

At block 1316, the system 100 can include the medical image in the virtual 3D scene and cause the display to concurrently display a perspective rendering of at least a portion of the second virtual medical device based at least in part on the determined emplacement of the second virtual medical device, similar to the display of the medical described above with reference to block 1314. In some embodiments, the display of the second virtual medical device can be based at least in part on dimensions of a corresponding real medical device (non-limiting examples: size, shape, or other appearance). As described above with respect to block 1314, the perspective view or rendering the medical image can be determined and displayed based at least in part on a point-of-view location.

At block 1318, the system 100 can cause a display to display a view of a virtual 3D scene including a perspective rendering of at least a portion of the medical image based at least in part on the determined emplacement of the medical image. As described above with respect to block 1314, the perspective view or rendering the medical image can be determined and displayed based at least in part on a point-of-view location.

At blocks 1322 and 1324, the system 100 can cause a display to display the first and second trajectory indicators. As described above, a healthcare provider can use the displayed trajectory indicators to view and manipulate the emplacement of the medical device and its trajectory before it enters the patient's body along a drive path. In some embodiments, this is accomplished by the doctor positioning a trajectory indicator such that it is coincident (or passes through) an ultrasound representation of a target such as tissue that the doctor has spotted in the ultrasound. Positioning the trajectory indicator(s) such that it is properly aimed at the target can provide guidance to the doctor as she directs a medical device into the body until it reaches its desired target or destination. For example, if the doctor identifies tissue in the medical image which needs attention, she can align the medical such that the trajectory indicators on display intersect or otherwise indicate that the medical device, if directed along the appropriate axis, will reach the tissue.

At blocks 1326 and 1328, the system 100 can cause a display to display the first and second intersection indicators. As described above, using the intersection indicators, the healthcare provider can identify where a medical device (e.g., a multi-axis device) will intersect the plane (e.g., the image plane) if moved along a drive path (e.g., a primary, a secondary axis, axis parallel to the primary or secondary axis, etc.). Based on the desired placement of the medical device, the healthcare provider can change the position and orientation of the medical device as desired. Thus, the intersection indicators as well as the trajectory indicators can aid a healthcare provider during the placement of a medical device. Furthermore, the system can calculate distances between the planes and the tips of the medical devices or other portions of the medical devices. The calculated distances can be displayed and/or used to display the medical devices.

In some embodiments, the system 100 can determine and display a point of intersection between a plane of interest (for example, an image plane, a medical device plane, etc.) and one or more medical device trajectories. For example, the system can determine and display a point of intersection between an image plane and a joint member trajectory. In some embodiments, the system 100 can determine and display a point of intersection between a medical device plane and another medical device trajectory. In some embodiments, the system 100 can determine and display a point of intersection between a ghost display object (or trajectory of a ghost display object) and a plane (for example, an image plane, a medical device plane, etc.). In some embodiments, a point of intersection can be determined and displayed between a ghost display object (or its trajectory) and a medical device plane. For example, if the ghost display object is a ghost medical device, an intersection indicator can be displayed at the intersection of a trajectory of the ghost joint member and the medical device plane. Alternatively or in addition, an intersection indicator can be displayed at the intersection of the trajectory of the ghost second limb member along the drive path and the medical image. In some examples, the point(s) of intersection are located on the image plane, within the medical image. In other examples, the point(s) of intersection are located on the image plane, outside of the medical image.

It will be understood that the various blocks described herein can be implemented in a variety of orders, and that the system 100 can implement one or more of the blocks concurrently and/or change the order, as desired. For example, the system 100 can concurrently receive the emplacement data from different sources, concurrently receive the medical image, or receive the data in any order. Similarly, the system 100 can concurrently determine the emplacement of the medical image and/or one or more virtual medical devices, etc.

Furthermore, it will be understood that fewer, more, or different blocks can be used as part of the routine 1300. For example, the routine 1300 can include blocks for receiving emplacement data associated with additional emplacement sensors or medical devices, determining emplacements of one or more medical devices, corresponding virtual medical devices, other display objects, displays, and/or users. In some embodiments, the routine 1300 can include determining an emplacement of a medical device associated with the medical image and determining the emplacement of the medical image based at least in part on the determined emplacement of the medical device (or corresponding virtual medical device), and display the virtual medical device concurrently with the medical image. Furthermore, the system 100 can determine and display a variety of image guidance cues, such as trajectory indicators, affected region indicators, intersection indicators, medical devices in different states or configurations, ghost display objects, as described in greater detail above, and below with reference to FIG. 14. In addition, in some cases, the routine 1300 can omit certain blocks, such as, but not limited to, blocks 1302, 1304, 1308, 1316, 1318, 1322, and/or 1324. For example, in some embodiments, the system may not determine emplacement of or display a portion of the second display object and/or may not display a portion of the first medical device, first trajectory indicator, and/or second trajectory indicator, etc.

Figure 14:
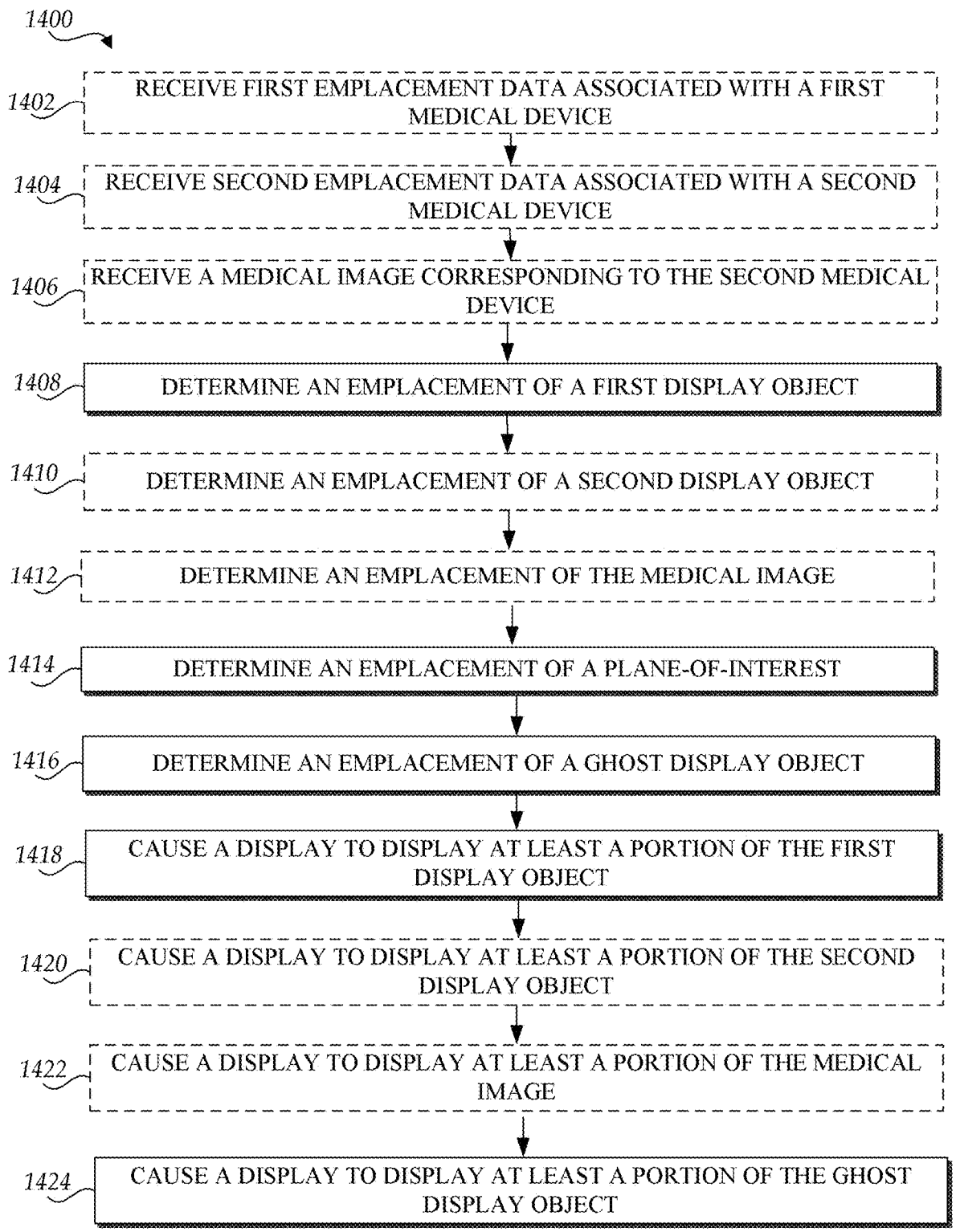
FIG. 14 is a flow diagram illustrative of an embodiment of a routine implemented by the system to project a display object onto a plane-of-interest to display a ghost display object.

FIG. 14 is a flow diagram illustrative of an embodiment of a routine implemented by the system to project a display object onto a plane-of-interest to display a ghost display object. One skilled in the relevant art will appreciate that the elements outlined for routine 1400 can be implemented by one or more computing devices/components that are associated with the system 100, such as the position sensing unit 140, the image guidance unit 130, surgical system 149, an HMD, and/or the imager 150. Accordingly, routine 1400 has been logically associated as being generally performed by the system 100. However, the following illustrative embodiment should not be construed as limiting. Furthermore, it will be understood that the various blocks described herein with reference to FIG. 14 can be implemented in a variety of orders. For example, the system 100 can implement some blocks concurrently or change the order, as desired. Furthermore, it will be understood that fewer, more, or different blocks can be used as part of the routine 1400. For example, in some embodiments, the solid blocks are part of routine 1400 and the dotted blocks are not implemented. However, it will be understood that any of the blocks (and more or different blocks) can be implemented as part of routine 1400.

At block 1402, as also described above with reference to block 1302 of FIG. 13, the system 100 receives first emplacement data associated with a first emplacement sensor and/or a first medical device. In some embodiments, the first emplacement sensor can be associated with the first medical device. In some embodiments, the first medical device is a multi-axis medical device. Furthermore, the first medical device can have a joint member having a joint member axis, a first limb member having a first axis, and a second limb member having a second axis that is different from the joint member axis and the first axis. As described above, one or more emplacement sensors can be associated with a first limb member, a second limb member, and/or a joint member of the associated first medical device.

At block 1404, as also described above with reference to block 1304 of FIG. 13, the system 100 receives second emplacement data associated with a second emplacement sensor and/or a second medical device.

At block 1406, the system 100 receives a medical image corresponding to the second medical device.

At block 1408, as described similarly above with reference to block 1306 of FIG. 13, the system 100 determines an emplacement of a first display object based at least in part on received first emplacement data. In some embodiments, the first display object can be a multi-axis medical device having a joint member, a first limb member, and a second limb member. In some embodiments, the second display object can be any medical display objects (e.g., virtual medical device, medical image, ghost display object, etc.) and/or any image guidance cue (e.g., trajectory indicator, intersection indicator, plane indicator, ghost display object, etc.).

At block 1410, the system 100 determines an emplacement of a second display object based at least in part on received second emplacement data. In some embodiments, the second display object can be a medical image. In some embodiments, display object can be any medical display objects (e.g., virtual medical device, medical image, ghost display object, etc.) and/or any image guidance cue (e.g., trajectory indicator, intersection indicator, plane indicator, ghost display object, etc.).

At block 1412, as also described above with reference to block 1310 of FIG. 13, the system 100 determines an emplacement of a medical image (e.g., medical image) based at least in part on received second emplacement data.

At block 1414, the system 100 determines an emplacement of a plane-of-interest. In some embodiments, the plane-of-interest is the plane to which that the display object is to be projected. For example, the plane-of-interest can be an image plane (e.g., the plane corresponding to a medical image), a medical device plane (e.g., the plane corresponding to a virtual medical device), or any other display object plane or other desired plane. In some embodiments, the plane-of-interest can include only a portion of a plane (e.g., the medical image portion of the image plane). However, it will be understood that a plane-of-interest can include more than a portion of any plane including but not limited to the image plane, medical device plane, affected region plane, or other display object plane. In some embodiments, the plane-of-interest can be determined dynamically based on the display object plane. Further, in some cases, the plane-of-interest can be selected to be a plane that is parallel to the display object plane. For example, the plane-of-interest can be selected as the display object plane (as described below) that is parallel to the image plane of a medical image. However, it will be understood that in some cases, the plane-of-interest can be predetermined, such as a display object plane that bisects the display object into halves.

In some embodiments, the display object plane corresponds to any plane that is parallel to a primary or secondary axis of the display object. In some embodiments, a virtual medical device plane can correspond to a plane that bisects the virtual medical device lengthwise or along its longitudinal axis. For example, the plane can bisect the virtual medical device into left and right portions (non-limiting examples: halves or other division), top and bottom portions (non-limiting examples: halves or other division), upper-right and lower left portions, upper-left and lower right portions, etc. In some cases, a display object plane can be determined dynamically based on the plane-of-interest. Further, in certain cases, the display object plane can be selected to be a plane that bisects the display object and that is parallel to the plane-of-interest. For example, the display object plane can be selected as a plane (e.g., a plane corresponding to an axis of the display object) that is parallel to the plane-of-interest. Thus, the display object plane can change as the display object moves throughout the system. However, it will be understood that in some cases, the display object plane can be predetermined. The emplacement of the plane-of-interest can be determined using a similar technique as described above.

At block 1416, the system 100 determines an emplacement of a ghost display object. The emplacement of the ghost display object can be determined using a variety of techniques, as described above. For examples, a ghost object can be projected onto the plane-of-interest. A ghost display object (e.g., projected display object) can be projected onto a plane-of-interest using a variety of techniques. For example, the ghost display object can be an orthographic projection of the display object onto the plane-of-interest. As a non-limiting example, the display object is a virtual medical device and the plane-of-interest is an image plane. The system calculates a plurality of lines which are perpendicular to the image plane. For each perpendicular line that intersects the virtual medical device (or a subset thereof), a point is displayed on the image plane at the location corresponding to the intersecting perpendicular line. As a result, a plurality of points are displayed on the image plane which correspond to the plurality of perpendicular lines (or subset thereof) intersecting the virtual medical device. The plurality of points can illustrate an indication of the virtual medical device on the image plane. In some embodiments, the plurality of points can be referred to as a ghost, a shadow, an outline, a marking, a projection, or an indication of the virtual medical device. It should be understood that the number of perpendicular lines (and the number of corresponding points) can vary across embodiments. For example, in some embodiments, there can be almost infinite perpendicular lines such that a complete representation of the virtual medical device is displayed on the image plane. In some embodiments, the perpendicular lines can be spaced out at predefined intervals such that the ghost medical device includes a dotted outline or dotted representation of the medical device. Similarly, in some cases, the subset of perpendicular lines used to generate the ghost display object can correspond to lines that intersect with a particular portion of the virtual medical device, such as the edge thereby creating an outline on the plane-of-interest.

In some embodiments, a ghost display object can be projected onto a plane-of-interest using a virtual light source. Consider a virtual light source that is at least as large as the display object to be projected or that covers an entire plane (e.g., a light source plane) positioned behind the display object (e.g., distal the plane-of-interest relative to the display object) and parallel to the plane-of-interest, and that emits parallel light waves. In examples such as these, the ghost display object can be displayed on the plane-on-interest as a shadow of the display object. Because the light source is infinitely wide (and can be infinitely far away), the size of the ghost display object can correspond directly with the size of the display object. Further, it will be understood that in some cases, the system can display an outline of the shadow generated by the virtual light source or other indicator.

In some embodiments, a display object can be projected by identifying points on a display object plane that correspond (e.g., intersect) to the display and mapping (e.g., projecting, reproducing, copying) the identified points onto a plane-of-interest. In some embodiments, the identified points on the display object plane can include a plurality of points (e.g., coordinates) that intersect with the corresponding display object. For instance, the plane of a virtual medical device can be a plane that bisects the virtual medical device. The plane can include a plurality of points that intersect with the virtual medical device. In a non-limiting example, to project the virtual medical device onto an image plane, at least some of the plurality of intersecting points can be drawn on the image plane. In certain cases, as described above, the resulting ghost medical device can include an outline or cross-section of the virtual medical device.

In some embodiments, a display object can be projected by identifying or determining which points (e.g., coordinates) of the plane-of-interest are closest (e.g., nearest) to points (e.g., coordinates) of the display object or points of the display object intersecting the display object plane (as described above). Each of the points corresponding to the display object (or the display object plane) can be projected onto the plane-of-interest at the location of the points of the plane-of-interest that were determined to be closest to the identified points of the display object. In some embodiments, projecting can include determining portions of the plane-of-interest that are closest to the display object. The display object can be projected onto those portions of the plane-of-interest that are closest to the display object. In some embodiments, projecting can include determining coordinates of a cross-sectional outline of the display object that are closest to the plane-of-interest.

Alternatively, or in addition, a medical image can be projected onto a plane of another medical device (e.g., a multi-axis medical device). In certain embodiments, the system 100 projects at least a portion of the medical image onto a virtual medical device plane of a virtual medical device based at least in part on the determined emplacement of the virtual medical device and the determined emplacement of the medical image and/or medical device associated with the medical image (e.g., a medical imaging device such as an ultrasound transducer). The ghost medical image can be displayed in a 2D view or 3D view and/or as a perspective view.

At steps 1418-1422, as similarly described above with respect to blocks 1316-1320 of FIG. 13, the system 100 can display a 3D rendering of at least a portion of the first display object, the second display object, or the medical image.

At step 1424, the system can display a 3D rendering of at least a portion of the ghost display object. In some embodiments, a ghost display object is an outline or other indication of all or a portion of the display object. In some embodiments, the ghost display object is a cross-sectional outline of the display object or a portion thereof. In some embodiments, a ghost display object is a projection of a full or partial representation of the display object. For example, a ghost medical device can include a representation of medical device having a first limb member, the second limb member, and/or joint member on the image plane. In some embodiments, the system can display a rendering of at least a portion of the medical image projected onto the plane-of-interest.

It will be understood that the various blocks described herein can be implemented in a variety of orders, and that the system 100 can implement one or more of the blocks concurrently and/or change the order, as desired. For example, the system 100 can concurrently receive the emplacement data from different sources, concurrently receive the medical image, or receive the data in any order. Similarly, the system 100 can concurrently determine the emplacement of the medical image and/or one or more virtual medical devices, etc.

Furthermore, it will be understood that fewer, more, or different blocks can be used as part of the routine 1400. For example, the routine 1400 can include blocks for receiving emplacement data associated with additional emplacement sensors or medical devices, determining emplacements of one or more medical devices, corresponding virtual medical devices, other display objects, displays, and/or users. In some embodiments, the routine 1400 can include determining an emplacement of a medical device associated with the medical image and determining the emplacement of the medical image based at least in part on the determined emplacement of the medical device (or corresponding virtual medical device), and display the virtual medical device concurrently with the medical image. Furthermore, the system 100 can determine and display a variety of image guidance cues, such as trajectory indicators, affected region indicators, as described above. In addition, in some cases, the routine 1400 can omit certain blocks, such as, but not limited to, blocks 1402, 1404, 1406, 1410, 1412, 1420, and/or 1422. For example, in some embodiments, the system may not determine emplacement of or display a portion of the second display object and/or the medical image.

In addition, it will be understood that the various blocks described herein with reference to FIG. 13 can be implemented in routine 1400, in a variety of orders. For example, the system 100 can implement some or all of various blocks of FIG. 13 in routine 1400 concurrently or change the order as desired.

Figure 15:
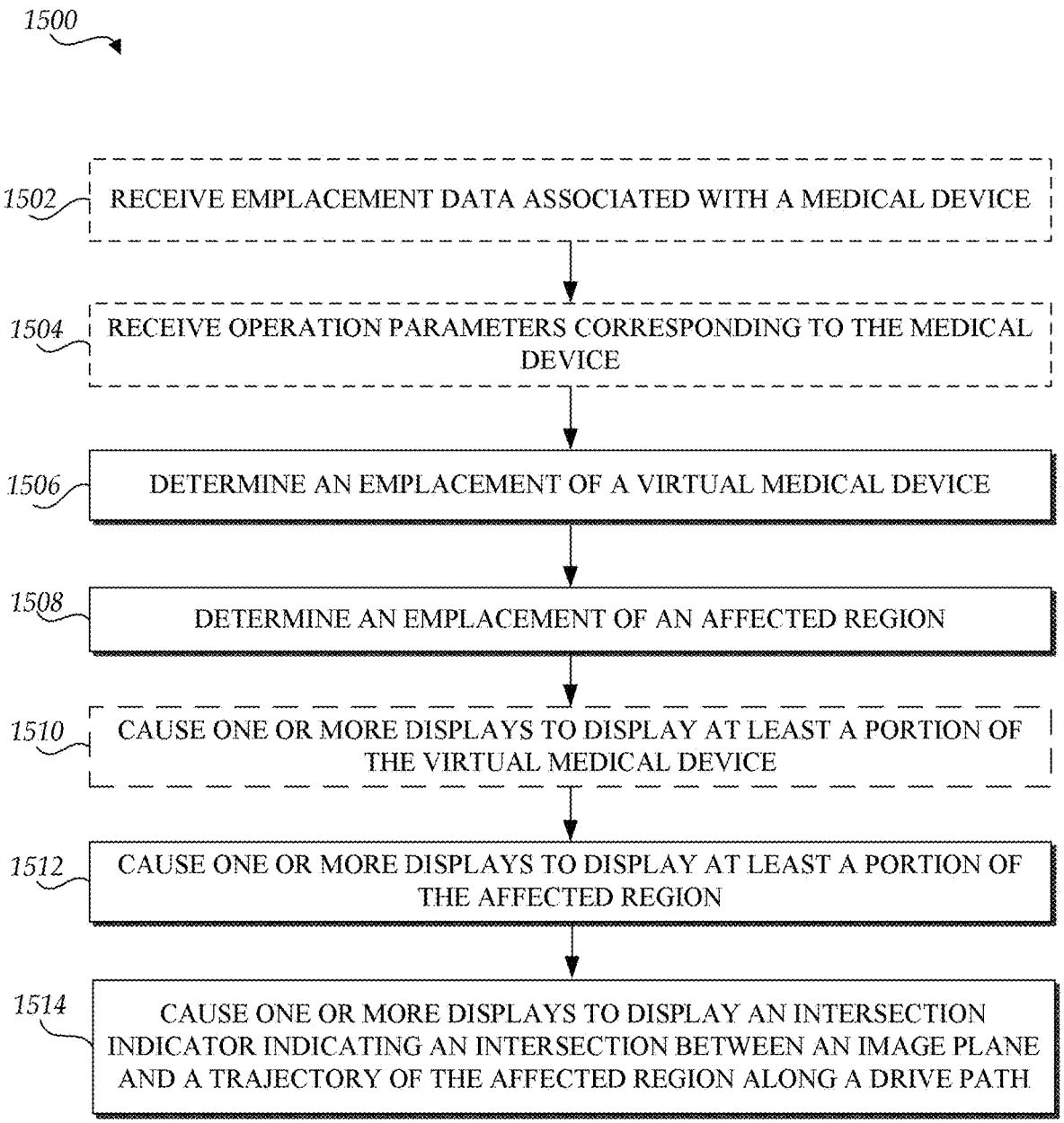
FIG. 15 is a flow diagram illustrative of an embodiment of a routine implemented by the system to display an affected region of a medical device.

FIG. 15 is a flow diagram illustrative of an embodiment of a routine implemented by the system to display an affected region of a medical device. One skilled in the relevant art will appreciate that the elements outlined for routine 1500 can be implemented by one or more computing devices/components that are associated with the system 100, such as the position sensing unit 140, the image guidance unit 130, surgical system 149, and/or imaging unit 150. Accordingly, routine 1500 has been logically associated as being generally performed by the system 100. However, the following illustrative embodiment should not be construed as limiting. Furthermore, it will be understood that the various blocks described herein with reference to FIG. 15 can be implemented in a variety of orders. For example, the system may implement some blocks concurrently or change the order, as desired. Furthermore, it will be understood that fewer, more, or different blocks can be used as part of the routine 1500. For example, in some embodiments, the solid blocks are part of routine 1500 and the dotted blocks are not implemented. However, it will be understood that any of the blocks (and more or different blocks) can be implemented as part of routine 1500.

At block 1502, as also described above with reference to block 1302 of FIG. 13, the system 100 receives first emplacement data associated with a first emplacement sensor and/or a first medical device. In some embodiments, the first emplacement sensor can be associated with the first medical device. In some embodiments, the first medical device can be a multi-axis medical device. Furthermore, the first medical device can have a joint member having a joint member axis, a first limb member having a first axis, and a second limb member having a second axis that is different from the joint member axis and the first axis. As described above, one or more emplacement sensors can be associated with a first limb member, a second limb member, and/or a joint member of the associated first medical device.

At block 1504, the system 100 receives operating parameters of a medical device. As described in greater detail above, the operating parameters can include information regarding make and model, power, dimensions of the medical device (such as length or width of the first limb member and/or the second limb member, angle data, distance from the hinge), range of movement data, etc. The operating parameters can be stored in a non-transitory, computer-readable medium associated with the system 100 and/or can be stored in the medical device. The operating parameters can be manually entered and/or automatically computed by the guidance system.

At block 1506, as also described above with reference to block 1306 of FIG. 13, the system 100 can determine an emplacement of a first virtual medical device based at least in part on the received first emplacement data. As described above, the second virtual medical device can correspond to a multi-axis device such as a transecting stapler, grasper, or vessel sealer. In some embodiments, the virtual medical device corresponds to a single-axis device such as an ablation probe.

At block 1508, the system 100 can determine an emplacement of an affected region. In some embodiments, the system determines the affected region based at least in part on the operating parameters and/or measured parameters. As described previously, an affected region can correspond to a region of tissue that will be affected when the device is operated. As a non-limiting example, the first affected region can correspond to a volume located between the first limb member and the second limb member. In some examples, the first affected region can be one or more sub-regions of the region affected when the medical device (e.g., multi-axis medical device) is operated. For example, the affected region can correspond to the plane at which the transecting knife cuts and/or the one or more planes corresponding to the one or more staples. The emplacement of the affected region can be determined in a similar manner as described above with respect to determining emplacement of a medical image, virtual medical device, ghost display object, etc.

At block 1510, similar to block 1316 of FIG. 13, the system 100 can cause the one or more displays to display a view of a virtual 3D scene including a perspective rendering of at least a portion of the first virtual medical device based at least in part on the determined emplacement of the first virtual medical device. In some embodiments, the 3D rendering of the at least a portion of the first virtual medical device includes at least a portion of the first limb member and at least a portion of the second limb member. However, it will be understood that the 3D rendering of the at least a portion of the first virtual medical device can include any portions of the first virtual device.

At block 1512, the system 100 causes the one or more displays to display at least a portion of the affected region. As described previously, the displayed affected region can be displayed in a 2D view or 3D view and/or as a perspective view. In addition, as described in greater detail above, the displayed affected region can be displayed as a volume, area, and/or line. The displayed affected region can be wire-framed, transparent, semi-transparent, have varied opacity, brightness, and/or focus, include alternating bands/tiles, be textured, include solid or dashed lines, include spikes, etc. In certain embodiments, the at least a portion of the affected region corresponds to portions of the affected region that are unique to it, with respect to other affected regions. In some embodiments, the displayed affected region corresponds to at least a portion of the affected region that is co-located with at least a portion of a medical display object (non-limiting examples: a virtual medical device, medical image, etc.) or its trajectory, also referred to as the surface display region.

At block 1514, the system 100 causes the one or more displays to display an intersection indicator indicating an intersection between an image plane and a trajectory of the affected region along a drive path. As described above, for example with respect to block 1312 of FIG. 3, the drive path can correspond to one of a plurality of paths. For example, in some embodiments, the drive path is parallel to a joint member axis.

In some embodiments (non-limiting examples illustrated in FIGS. 9-12), the medical image or medical image can traverse the affected region of the medical device. For example, the affected region can correspond to a region of tissue that will be affected by a transecting knife and/or staples when a multi-axis device is operated. In some embodiments, the medical image is traverse (or extends across) at least a portion of the affected region.

With continued reference to FIG. 15, it will be understood that fewer or more blocks can be included. For example, as described in greater detail above, the system 100 can receive emplacement data from one or more sensors corresponding to one or more medical devices, determine a emplacement of the medical devices and/or corresponding virtual medical devices (as a non-limiting example, the emplacement can be determined based at least in part on a point-of-view location), cause one or more displays to display the virtual medical devices and/or perspective views thereof, determine emplacement of the affected regions with respect to the virtual medical devices, determine emplacement of and display an medical image, alter the display of the medical image, display the medical display objects in a 2D view, a 3D view, and/or a perspective view, etc. In some cases, the routine 1500 can omit certain blocks, such as, but not limited to, blocks 1502, 1504, and/or 1510. For example, in some embodiments, the system may not display a portion of the virtual medical device, etc.

In addition, it will be understood that the various blocks described herein with reference to FIGS. 13 and/or 14 can be implemented in routine 1500, in a variety of orders. For example, the system 100 can implement some or all of various blocks of FIGS. 13 and/or 14 in routine 1500 concurrently or change the order as desired.

Figure 16:
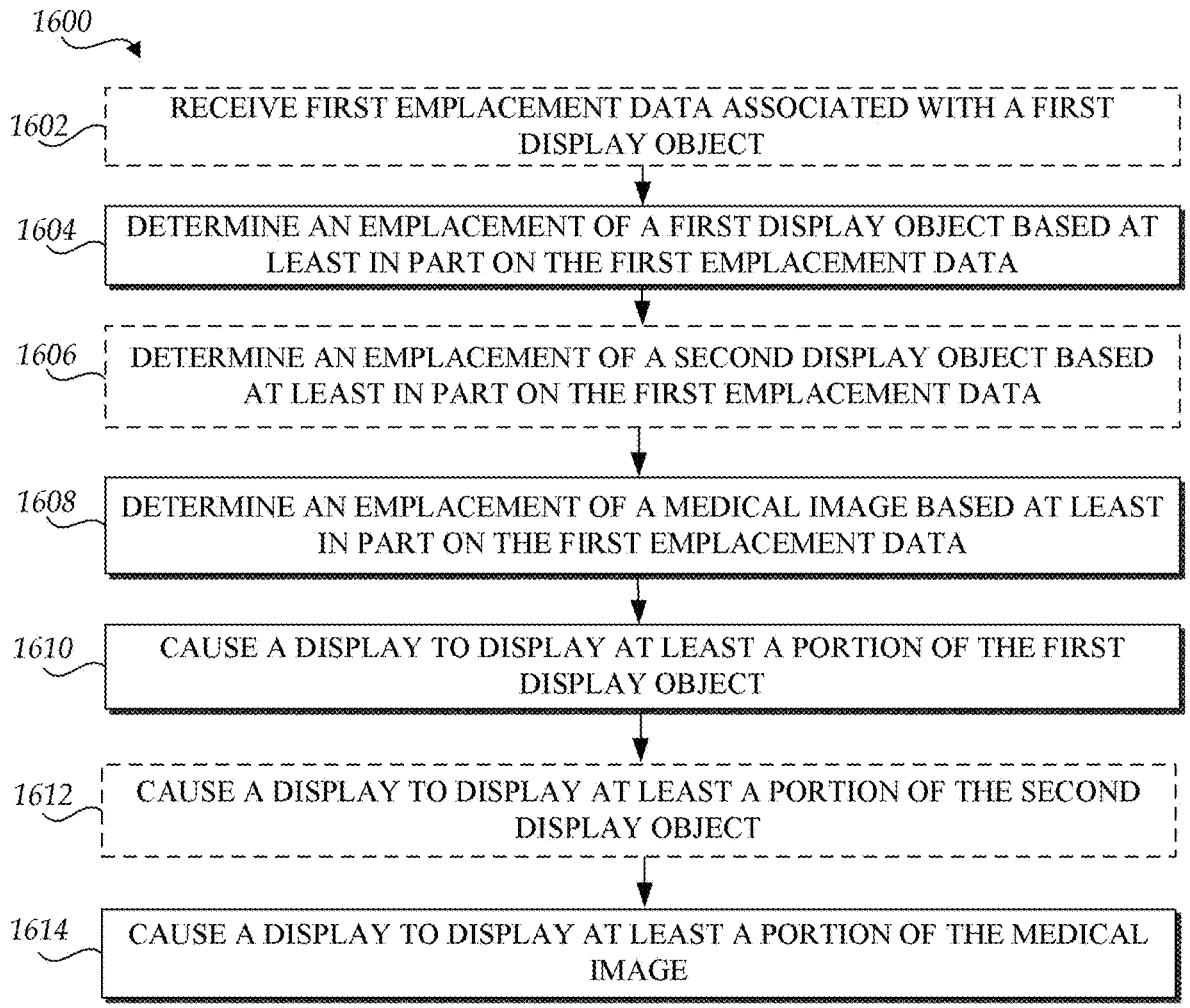
FIG. 16 is a flow diagram illustrative of an embodiment of a routine implemented by the system to determine emplacement of a virtual medical device and a medical image based at least in part on received emplacement data associated with a medical device.

FIG. 16 is a flow diagram illustrative of an embodiment of a routine implemented by the system to determine emplacement of a virtual medical device and a medical image based at least in part on received emplacement data associated with a medical device. One skilled in the relevant art will appreciate that the elements outlined for routine 1600 can be implemented by one or more computing devices/components that are associated with the system 100, such as the position sensing unit 140, the image guidance unit 130, surgical system 149, an HMD, and/or the imager 150. Accordingly, routine 1600 has been logically associated as being generally performed by the system 100. However, the following illustrative embodiment should not be construed as limiting. Furthermore, it will be understood that the various blocks described herein with reference to FIG. 16 can be implemented in a variety of orders. For example, the system 100 can implement some blocks concurrently or change the order as desired. Furthermore, it will be understood that fewer, more, or different blocks can be used as part of the routine 1600. For example, in some embodiments, the solid blocks are part of routine 1600 and the dotted blocks are not implemented. However, it will be understood that any of the blocks (and more or different blocks) can be implemented as part of routine 1600.

In some embodiments, such as those illustrated in in FIGS. 9-12, an ultrasound transducer (for example, a miniature ultrasound transducer) can be integrated with a multi-axis instrument such as a transecting stapler, grasper, or vessel sealer. In examples such as these, an emplacement of a virtual medical device (for example, a stapler) and the emplacement of a virtual medical image can be determined based at least in part on emplacement data associated with a single emplacement sensor.

At block 1602, as described above with reference to block 1303 of FIG. 13, the system 100 receives first emplacement data associated with a first emplacement sensor and/or a first medical device. The first emplacement data can be generated by the first emplacement sensor and/or by a position sensing unit. In some embodiments, the first emplacement sensor can be associated with the first medical device (e.g., a stapler).

At block 1604, as described above with reference to block 1306 of FIG. 13, the system 100 can determine an emplacement of a first virtual medical device based at least in part on the received first emplacement data. As described above, the first virtual medical device can correspond to a multi-axis device such as a transecting stapler, grasper, or vessel sealer. In some embodiments, the virtual medical device corresponds to a single-axis device such as an ablation probe.

At block 1606, similar to block 1308 of FIG. 13, the system 100 can determine an emplacement of a second virtual medical device based at least in part on the received first emplacement data. As described above, a single sensor and/or single emplacement data can be used to determine the emplacement of the first medical device and the second medical device.

At block 1608, similar to block 1310 of FIG. 13, the system 100 can determine an emplacement of a medical image based at least in part on the received first emplacement data. As described above, a single sensor and/or single emplacement data can be used to determine the emplacement of the first medical device, the second medical device, and the medical image. As mentioned above, in some embodiments, because the medical device (for example, the stapler) and the ultrasound transducer are integrated together, both the emplacement of the virtual medical device and the emplacement of the virtual ultrasound transducer (and medical image) can be determined based at least at least in part on the received first emplacement data.

At steps 1610-1614, as similarly described above with respect to blocks 1316-1320 of FIG. 13, the system 100 can display a 3D rendering of at least a portion of the first display object, the second display object, or the medical image. However, it should be noted that each of these display objects are displayed based at least in part on the first emplacement data.

It will be understood that the various blocks described herein can be implemented in a variety of orders, and that the system 100 can implement one or more of the blocks concurrently and/or change the order, as desired. For example, the system 100 can concurrently receive the emplacement data from different sources, concurrently receive the medical image, or receive the data in any order. Similarly, the system 100 can concurrently determine the emplacement of the medical image and/or one or more virtual medical devices, etc.

Furthermore, it will be understood that fewer, more, or different blocks can be used as part of the routine 1600. For example, the routine 1600 can include blocks for receiving emplacement data associated with additional emplacement sensors or medical devices, determining emplacements of one or more medical devices, corresponding virtual medical devices, other display objects, displays, and/or users. In some embodiments, the routine 1600 can include determining an emplacement of a medical device associated with the medical image and determining the emplacement of the medical image based at least in part on the determined emplacement of the medical device (or corresponding virtual medical device), and display the virtual medical device concurrently with the medical image. Furthermore, the system 100 can determine and display a variety of image guidance cues, such as trajectory indicators, affected region indicators, as described above. In some cases, the routine 1600 can omit certain blocks, such as, but not limited to, blocks 1602, 1606, 1612, and/or 1614. For example, in some embodiments, the system may not determine emplacement of or display a portion of the second display object.

In addition, it will be understood that the various blocks described herein with reference to FIGS. 14 and 15 can be implemented in routine 1600, in a variety of orders. For example, the system 100 can implement some or all of various blocks of FIGS. 14 and 15 in routine 1600 concurrently or change the order as desired.

Example Embodiments

Various example embodiments of methods, systems and non-transitory computer-readable medium relating to one or more intersection indicators corresponding to an intersection between a plane-of-interest and one or more trajectories of a medical device can be found in the following clauses:

Clause 1. A method for medical device navigation, the method comprising:
  receiving first emplacement data associated with a first medical device, the first medical device comprising a joint member having a joint member axis, a first limb member having a first axis, and a second limb member having a second axis that is different from the joint member axis and the first axis;
  receiving second emplacement data associated with a second medical device;
  determining an emplacement of a first virtual medical device corresponding to the first medical device based at least in part on the received first emplacement data;
  determining an emplacement of a second virtual medical device corresponding to the second medical device based at least in part on the received second emplacement data;
  determining an emplacement of a medical image based at least in part on the received second emplacement data;
  determining a first intersection between an image plane and a trajectory of the first limb member along a drive path that is parallel to the joint member axis, wherein the image plane corresponds to the medical image;
  determining a second intersection between the image plane and a trajectory of the second limb member along the drive path; and
  causing one or more displays to concurrently display a perspective view of:
    a 3D rendering of at least a portion of the first virtual medical device based at least in part on the determined emplacement of the first virtual medical device, the 3D rendering of the first virtual medical device including at least the first limb member and the second limb member,
    a 3D rendering of at least a portion of the second virtual medical device based at least in part on the determined emplacement of the second virtual medical device,
    a 3D rendering of at least a portion of the medical image based at least in part on the determined emplacement of the medical image,
    a first trajectory indicator corresponding to the trajectory of the first limb member along the drive path,
    a second trajectory indicator corresponding to the trajectory of the second limb member along the drive path,
    a first intersection indicator corresponding to the first intersection, and
    a second intersection indicator corresponding to the second intersection.

Clause 2. A method for medical device navigation, the method comprising:
  determining an emplacement of a first virtual medical device corresponding to a first medical device, the first medical device comprising a joint member having a joint member axis, a first limb member having a first axis, and a second limb member having a second axis that is different from the joint member axis and the first axis;
  determining an emplacement of a medical image;
  determining a first intersection between an image plane corresponding to the medical image and a trajectory of the first limb member along a drive path;
  determining a second intersection between the image plane and a trajectory of the second limb member along the drive path; and
  causing one or more displays to concurrently display a perspective view of:
    a 3D rendering of at least a portion of the medical image based at least in part on the determined emplacement of the medical image,
    a first intersection indicator corresponding to the first intersection, and
    a second intersection indicator corresponding to the second intersection.

Clause 3. The method of Clause 2, further comprising:
  receiving first emplacement data associated with the first medical device;
  receiving second emplacement data associated with a second medical device; and
  determining an emplacement of a second virtual medical device corresponding to the second medical device based at least in part on the received second emplacement data,
  wherein said determining the emplacement of the first virtual medical device is based at least in part on the received first emplacement data and said determining the emplacement of the medical image is based at least in part on the received second emplacement data.

Clause 4. The method of any of the Clauses 2-3, wherein causing the one or more displays to concurrently display a perspective view further comprises causing concurrent display of:
  a 3D rendering of at least a portion of the first virtual medical device based at least in part on the determined emplacement of the first virtual medical device, the 3D rendering of the first virtual medical device including at least the first limb member and the second limb member, or
  a 3D rendering of at least a portion of the second virtual medical device based at least in part on the determined emplacement of the second virtual medical device.

Clause 5. The method of any of the Clauses 2-4, wherein causing the one or more displays to concurrently display a perspective view further comprises causing concurrent display of:
  a first trajectory indicator corresponding to the trajectory of the first limb member along the drive path, or a second trajectory indicator corresponding to the trajectory of the second limb member along the drive path.

Clause 6. The method of any of the Clauses 2-5, wherein the drive path is parallel to at least one of the joint member axis, the first axis, or the second axis.

Clause 7. The method of any of the Clauses 2-6, wherein the drive path is perpendicular to at least one of the joint member axis, the first axis, or the second axis.

Clause 8. The method of any of the Clauses 2-7, wherein the drive path is predefined.

Clause 9. The method of any of the Clauses 2-8, wherein the drive path is dynamic and is based at least in part on detected movement of first medical device or the second medical device.

Clause 10. The method of any of the Clauses 2-9, wherein a primary axis of the first medical device is the joint member axis.

Clause 11. The method of any of the Clauses 2-10, wherein a secondary axis of the first medical device is the first axis and/or the second axis.

Clause 12. The method of any of the Clauses 2-11, wherein the first axis is parallel to the joint member axis.

Clause 13. The method of any of the Clauses 2-12, wherein the first axis is different from the joint member axis.

Clause 14. The method of any of the Clauses 2-13, wherein the first intersection indicator includes an outline of a cross-section of the first limb member.

Clause 15. The method of any of the Clauses 2-14, wherein the second intersection indicator includes an outline of a cross-section of the second limb member.

Clause 16. The method of any of the Clauses 2-15, wherein the first intersection indicator and/or the second intersection indicator includes a cross-sectional outline of a knife path and/or the first virtual medical device, wherein the knife path corresponds to a transecting knife of the first medical device.

Clause 17. The method of any of the Clauses 2-16, wherein the first intersection and/or the second intersection indicator includes an indication of at least a portion of the image plane.

Clause 18. The method of any of the Clauses 2-17, wherein the indication of at least a portion of the image plane comprises a box representative of a portion of the image plane.

Clause 19. The method of any of the Clauses 2-18, wherein the first trajectory indicator extends to at least a distal portion of the first limb member and corresponds to an axis along the drive path that is parallel to the joint member axis.

Clause 20. The method of any of the Clauses 2-19, wherein the first trajectory indicator corresponds to an axis that intersects with the first axis at a distal portion of the first limb member and is parallel to the joint member axis and the drive path.

Clause 21. The method of 20, wherein the second trajectory indicator extends to at least a distal portion of the second limb member and corresponds to an axis along the drive path that is different from and parallel to the joint member axis.

Clause 22. The method of any of the Clauses 2-213, wherein the second trajectory indicator corresponds to an axis that intersects with the second axis at a distal portion of the second limb member and is parallel to the joint member axis and the drive path.

Clause 23. The method of any of the Clauses 2-22, further comprising determining a cutting path associated with the first medical device, wherein causing the one or more displays to concurrently display a perspective view further comprises causing concurrent display of the cutting path.

Clause 24. The method of Clause 23, wherein the cutting path corresponds to a trajectory of a knife of the first medical device.

Clause 25. The method of any of the Clauses 2-24, further comprising:
  determining an emplacement of an affected region based at least in part on the determined emplacement of the first virtual medical device,
  wherein causing the one or more displays to concurrently display a perspective view further comprises causing concurrent display of:
    a 3D rendering of at least a portion of the affected region based at least in part on the determined emplacement of the virtual medical device, or
    an affected region intersection indicator indicating an intersection between a trajectory of the affected region along the drive path.

Clause 26. The method of Clause 25, wherein the affected region corresponds to a volume located between the first limb member and the second limb member.

Clause 27. The method of Clause 25, wherein the at least a portion of the affected region comprises a stapling path of at least one staple of the first medical device.

Clause 28. The method of Clause 25, wherein the at least a portion of the affected region comprises a cutting path of a knife of the first medical device.

Clause 29. The method of Clause 25, further comprising determining an intersection between the affected region and the medical image.

Clause 30. The method of Clause 29, wherein the at least a portion of the affected region comprises the intersection between the affected region and the medical image.

Clause 31. The method of Clause 25, further comprising receiving operating parameters corresponding to the first medical device, wherein determining the emplacement of an affected region is based at least in part on the received operating parameters.

Clause 32. The method of any of the Clauses 2-31, further comprising:
  determining an emplacement of a plane-of-interest based at least in part on the determined emplacement of one of the medical image; and
  determining an emplacement of a ghost medical device based at least in part on the determined emplacement of the first virtual medical device and the determined emplacement of the plane-of-interest,
  wherein causing the one or more displays to concurrently display a perspective view further comprises causing concurrent display of:
    a 3D rendering of at least a portion of the ghost medical device on the plane-of-interest based at least in part on the determined emplacement of the ghost medical device.

Clause 33. The method of any of the Clauses 2-32, further comprising:
  determining an emplacement of a plane-of-interest based at least in part on the determined emplacement of one of the first virtual medical device; and
  determining an emplacement of a ghost medical image based at least in part on the determined emplacement of the medical image and the determined emplacement of the plane-of-interest,
  wherein causing the one or more displays to concurrently display a perspective view further comprises causing concurrent display of:

a 3D rendering of at least a portion of the ghost medical image on the plane-of-interest based at least in part on the determined emplacement of the ghost medical image.

Clause 34. The method of any of Clauses 32 or 33, further comprising projecting the display object on the plane-of-interest to display the ghost display object.

Clause 35. The method of Clause 34, wherein projecting comprises determining at least one of portions, points, or coordinates of the plane-of-interest that are closest to the display object.

Clause 36. The method of Clause 34, wherein projecting comprises determining an arc path corresponding to the display object and the plane-of-interest.

Clause 37. The method of Clause 34, wherein projecting comprises determining which of a plurality of connecting lines intersect the display object, wherein the plurality of connecting lines extend orthogonally from the plane-of-interest to the display object.

Clause 38. The method of Clause 34, wherein projecting comprises using a virtual light source that is at least as large as the display object to be projected, wherein the light source is distal the plane-of-interest relative to the display object.

Clause 39. The method of Clause 32, wherein the ghost display object includes a cross-section and/or outline of display object.

Clause 40. The method of Clause 32, wherein the ghost display object includes a cross-section and/or outline of display object.

Clause 41. A system comprising:
a computer system in communication with a display, the computer system comprising a computer processor and a non-transitory storage medium, wherein the computer system is configured to:
  receive first emplacement data associated with a first medical device, the first medical device comprising a joint member having a joint member axis, a first limb member having a first axis, and a second limb member having a second axis that is different from the joint member axis and the first axis,
  receive second emplacement data associated with a second medical device;
  determine an emplacement of a first virtual medical device corresponding to the first medical device based at least in part on the received first emplacement data,
  determine an emplacement of a second virtual medical device corresponding to the second medical device based at least in part on the received second emplacement data,
  determine an emplacement of a medical image based at least in part on the received second emplacement data,
  determine a first intersection between an image plane and a trajectory of the first limb member along a drive path that is parallel to the joint member axis, wherein the image plane corresponds to the medical image,
  determine a second intersection between the image plane and a trajectory of the second limb member along the drive path, and
  cause the display to concurrently display a perspective view of:
    a 3D rendering of at least a portion of the first virtual medical device based at least in part on the determined emplacement of the first virtual medical device, the 3D rendering of the first virtual medical device including at least the first limb member and the second limb member,
    a 3D rendering of at least a portion of the second virtual medical device based at least in part on the determined emplacement of the second virtual medical device,
    a 3D rendering of at least a portion of the medical image based at least in part on the determined emplacement of the medical image,
    a first trajectory indicator corresponding to the trajectory of the first limb member along the drive path,
    a second trajectory indicator corresponding to the trajectory of the second limb member along the drive path,
    a first intersection indicator corresponding to the first intersection, and
    a second intersection indicator corresponding to the second intersection; and
  the display.

Clause 42. A system comprising:
a computer system in communication with a display, the computer system comprising a computer processor and a non-transitory storage medium, wherein the computer system is configured to:
  determine an emplacement of a first virtual medical device corresponding to a first medical device, the first medical device comprising a joint member having a joint member axis, a first limb member having a first axis, and a second limb member having a second axis that is different from the joint member axis and the first axis,
  determine an emplacement of a medical image,
  determine a first intersection between an image plane corresponding to the medical image and a trajectory of the first limb member along a drive path,
  determine a second intersection between the image plane and a trajectory of the second limb member along the drive path, and
  cause the display to concurrently display a perspective view of:
    a 3D rendering of at least a portion of the medical image based at least in part on the determined emplacement of the medical image,
    a first intersection indicator corresponding to the first intersection, and
    a second intersection indicator corresponding to the second intersection; and
  the display.

Clause 43. The system of the Clause 42, wherein the computer system is further configured to:
  receive first emplacement data associated with the first medical device;
  receive second emplacement data associated with a second medical device;
  determine an emplacement of a second virtual medical device corresponding to the second medical device based at least in part on the received second emplacement data;
  determine the emplacement of the first virtual medical device based at least in part on the received first emplacement data; and
  determine the emplacement of the medical image is based at least in part on the received second emplacement data.

Clause 44. The system of any of clauses 42 or 43, wherein the computer system is further configured to cause the display to concurrently display a perspective view of:
  a 3D rendering of at least a portion of the first virtual medical device based at least in part on the determined emplacement of the first virtual medical device, the 3D rendering of the first virtual medical device including at least the first limb member and the second limb member, or a 3D rendering of at least a portion of the second virtual medical device based at least in part on the determined emplacement of the second virtual medical device.

Clause 45. The system of any of clauses 42-44, wherein the computer system is further configured to cause the display to concurrently display a perspective view of:

a first trajectory indicator corresponding to the trajectory of the first limb member along the drive path, or a second trajectory indicator corresponding to the trajectory of the second limb member along the drive path.

Clause 46. The system of any of clauses 42-45, wherein the drive path is parallel to at least one of the joint member axis, the first axis, or the second axis.

Clause 47. The system of any of clauses 42-46, wherein the drive path is perpendicular to at least one of the joint member axis, the first axis, or the second axis.

Clause 48. The system of any of clauses 42-47, wherein the drive path is predefined.

Clause 49. The system of any of clauses 42-48, wherein the drive path is dynamic and is based at least in part on detected movement of first medical device or the second medical device.

Clause 50. The system of any of clauses 42-49, wherein a primary axis of the first medical device is the joint member axis.

Clause 51. The system of any of clauses 42-50, wherein a secondary axis of the first medical device is the first axis and/or the second axis.

Clause 52. The system of any of clauses 42-51, wherein the first axis is parallel to the joint member axis.

Clause 53. The system of any of clauses 42-52, wherein the first axis is different from the joint member axis.

Clause 54. The system of any of clauses 42-53, wherein the first intersection indicator includes an outline of a cross-section of the first limb member.

Clause 55. The system of any of clauses 42-54, wherein the second intersection indicator includes an outline of a cross-section of the second limb member.

Clause 56. The system of any of clauses 42-55, wherein the first intersection indicator and/or the second intersection indicator includes a cross-sectional outline of a knife path and/or the first virtual medical device, wherein the knife path corresponds to a transecting knife of the first medical device.

Clause 57. The system of any of clauses 42-56, wherein the first intersection and/or the second intersection indicator includes an indication of at least a portion of the image plane.

Clause 58. The system of clause 57, wherein the indication of at least a portion of the image plane comprises a box representative of a portion of the image plane.

Clause 59. The system of clause 45, wherein the first trajectory indicator extends to at least a distal portion of the first limb member and corresponds to an axis along the drive path that is parallel to the joint member axis.

Clause 60. The system of clause 45, wherein the first trajectory indicator corresponds to an axis that intersects with the first axis at a distal portion of the first limb member and is parallel to the joint member axis and the drive path.

Clause 61. The system of clause 45, wherein the second trajectory indicator extends to at least a distal portion of the second limb member and corresponds to an axis along the drive path that is different from and parallel to the joint member axis.

Clause 62. The system of clause 45, wherein the second trajectory indicator corresponds to an axis that intersects with the second axis at a distal portion of the second limb member and is parallel to the joint member axis and the drive path.

Clause 63. The system of any of clauses 42-62, wherein the computer system is further configured to determine a cutting path associated with the first medical device and cause the display to concurrently display a perspective view of the cutting path.

Clause 64. The system of clause 63, wherein the cutting path corresponds to a trajectory of a knife of the first medical device.

Clause 65. The system of any of clauses 42-64, wherein the computer system is further configured to:

determine an emplacement of an affected region based at least in part on the determined emplacement of the first virtual medical device; and causing the display to concurrently display a perspective view of:

a 3D rendering of at least a portion of the affected region based at least in part on the determined emplacement of the virtual medical device, or an affected region intersection indicator indicating an intersection between a trajectory of the affected region along the drive path.

Clause 66. The system of clause 65, wherein the affected region corresponds to a volume located between the first limb member and the second limb member.

Clause 67. The system of clause 65, wherein the at least a portion of the affected region comprises a stapling path of at least one staple of the first medical device.

Clause 68. The system of clause 65, wherein the at least a portion of the affected region comprises a cutting path of a knife of the first medical device.

Clause 69. The system of clause 65, wherein the at least a portion of the affected region comprises the intersection between the affected region and the medical image.

Clause 70. The system of any of clauses 42-69, wherein the computer system is further configured to determine an intersection between the affected region and the medical image.

Clause 71. The system of any of clauses 42-70, wherein the computer system is further configured to receive operating parameters corresponding to the first medical device and determine the emplacement of an affected region based at least in part on the received operating parameters.

Clause 72. The system of any of clauses 42-70, wherein the computer system is further configured to:

determine an emplacement of a plane-of-interest based at least in part on the determined emplacement of one of the medical image;

determine an emplacement of a ghost medical device based at least in part on the determined emplacement of the first virtual medical device and the determined emplacement of the plane-of-interest; and cause the display to concurrently display a perspective view of a 3D rendering of at least a portion of the ghost medical device on the plane-of-interest based at least in part on the determined emplacement of the ghost medical device.

Clause 73. The system of any of clauses 42-70, wherein the computer system is further configured to:

determine an emplacement of a plane-of-interest based at least in part on the determined emplacement of one of the first virtual medical device;

determine an emplacement of a ghost medical image based at least in part on the determined emplacement of the medical image and the determined emplacement of the plane-of-interest; and cause the display to currently display a perspective view of a 3D rendering of at least a portion of the ghost medical image on the plane-of-interest based at least in part on the determined emplacement of the ghost medical image.

Clause 74. The system of any one of clause 72 or 73, wherein the computer system is further configured to project the display object on the plane-of-interest to display the ghost display object.

Clause 75. The system of the Clause 74, wherein the computer system is further configured to determine at least one of portions, points, or coordinates of the plane-of-interest that are closest to the display object.

Clause 76. The system of any of clauses 74 or 75, wherein the computer system is further configured to determine an arc path corresponding to the display object and the plane-of-interest.

Clause 77. The system of any of clauses 74-76, wherein the computer system is further configured to determine which of a plurality of connecting lines intersect the display object, wherein the plurality of connecting lines extend orthogonally from the plane-of-interest to the display object.

Clause 78. The system of any of clauses 74-77, wherein the computer system further comprises a virtual light source that is at least as large as the display object to be projected, wherein the light source is distal the plane-of-interest relative to the display object.

Clause 79. The system of any of clauses 74-78, wherein the ghost display object includes a cross-section and/or outline of display object.

Clause 80. The system of any of clauses 74-79, wherein the ghost display object includes a cross-section and/or outline of display object.

Clause 81. A non-transitory computer-readable medium comprising computer executable instructions that when executed by one or more processors cause the one or more processors to:
receive first emplacement data associated with a first medical device, the first medical device comprising a joint member having a joint member axis, a first limb member having a first axis, and a second limb member having a second axis that is different from the joint member axis and the first axis,
receive second emplacement data associated with a second medical device;
determine an emplacement of a first virtual medical device corresponding to the first medical device based at least in part on the received first emplacement data,
determine an emplacement of a second virtual medical device corresponding to the second medical device based at least in part on the received second emplacement data,
determine an emplacement of a medical image based at least in part on the received second emplacement data,
determine a first intersection between an image plane and a trajectory of the first limb member along a drive path that is parallel to the joint member axis, wherein the image plane corresponds to the medical image,
determine a second intersection between the image plane and a trajectory of the second limb member along the drive path, and
cause the display to concurrently display a perspective view of:
a 3D rendering of at least a portion of the first virtual medical device based at least in part on the determined emplacement of the first virtual medical device, the 3D rendering of the first virtual medical device including at least the first limb member and the second limb member,
a 3D rendering of at least a portion of the second virtual medical device based at least in part on the determined emplacement of the second virtual medical device,
a 3D rendering of at least a portion of the medical image based at least in part on the determined emplacement of the medical image,
a first trajectory indicator corresponding to the trajectory of the first limb member along the drive path,
a second trajectory indicator corresponding to the trajectory of the second limb member along the drive path,
a first intersection indicator corresponding to the first intersection, and
a second intersection indicator corresponding to the second intersection.

Clause 82. A non-transitory computer-readable medium comprising computer executable instructions that when executed by one or more processors cause the one or more processors to:
determine an emplacement of a first virtual medical device corresponding to a first medical device, the first medical device comprising a joint member having a joint member axis, a first limb member having a first axis, and a second limb member having a second axis that is different from the joint member axis and the first axis,
determine an emplacement of a medical image,
determine a first intersection between an image plane corresponding to the medical image and a trajectory of the first limb member along a drive path,
determine a second intersection between the image plane and a trajectory of the second limb member along the drive path, and
cause the display to concurrently display a perspective view of:
a 3D rendering of at least a portion of the medical image based at least in part on the determined emplacement of the medical image,
a first intersection indicator corresponding to the first intersection, and
a second intersection indicator corresponding to the second intersection.

Clause 83. The non-transitory computer-readable medium of clause 82, wherein the computer executable instructions further cause the one or more processors to:
receive first emplacement data associated with the first medical device;
receive second emplacement data associated with a second medical device;
determine an emplacement of a second virtual medical device corresponding to the second medical device based at least in part on the received second emplacement data;
determine the emplacement of the first virtual medical device based at least in part on the received first emplacement data; and
determine the emplacement of the medical image is based at least in part on the received second emplacement data.

Clause 84. The non-transitory computer-readable medium of clauses 82 or 83, wherein the computer executable instructions further cause the one or more processors to cause the display to concurrently display a perspective view of:

a 3D rendering of at least a portion of the first virtual medical device based at least in part on the determined emplacement of the first virtual medical device, the 3D rendering of the first virtual medical device including at least the first limb member and the second limb member, or a 3D rendering of at least a portion of the second virtual medical device based at least in part on the determined emplacement of the second virtual medical device.

Clause 85. The non-transitory computer-readable medium of clauses 82-84, wherein the computer executable instructions further cause the one or more processors to cause the display to concurrently display a perspective view of:

a first trajectory indicator corresponding to the trajectory of the first limb member along the drive path, or a second trajectory indicator corresponding to the trajectory of the second limb member along the drive path.

Clause 86. The non-transitory computer-readable medium of any of clauses 82-85, wherein the drive path is parallel to at least one of the joint member axis, the first axis, or the second axis.

Clause 87. The non-transitory computer-readable medium of any of clauses 82-86, wherein the drive path is perpendicular to at least one of the joint member axis, the first axis, or the second axis.

Clause 88. The non-transitory computer-readable medium of any of clauses 82-87, wherein the drive path is predefined.

Clause 89. The non-transitory computer-readable medium of any of clauses 82-88, wherein the drive path is dynamic and is based at least in part on detected movement of first medical device or the second medical device.

Clause 90. The non-transitory computer-readable medium of any of clauses 82-89, wherein a primary axis of the first medical device is the joint member axis.

Clause 91. The non-transitory computer-readable medium of any of clauses 82-90, wherein a secondary axis of the first medical device is the first axis and/or the second axis.

Clause 92. The non-transitory computer-readable medium of any of clauses 82-91, wherein the first axis is parallel to the joint member axis.

Clause 93. The non-transitory computer-readable medium of any of clauses 82-92, wherein the first axis is different from the joint member axis.

Clause 94. The non-transitory computer-readable medium of any of clauses 82-93, wherein the first intersection indicator includes an outline of a cross-section of the first limb member.

Clause 95. The non-transitory computer-readable medium of any of clauses 82-94, wherein the second intersection indicator includes an outline of a cross-section of the second limb member.

Clause 96. The non-transitory computer-readable medium of any of clauses 82-95, wherein the first intersection indicator and/or the second intersection indicator includes a cross-sectional outline of a knife path and/or the first virtual medical device, wherein the knife path corresponds to a transecting knife of the first medical device.

Clause 97. The non-transitory computer-readable medium of any of clauses 82-96, wherein the first intersection and/or the second intersection indicator includes an indication of at least a portion of the image plane.

Clause 98. The non-transitory computer-readable medium of clause 97, wherein the indication of at least a portion of the image plane comprises a box representative of a portion of the image plane.

Clause 99. The non-transitory computer-readable medium of clause 85, wherein the first trajectory indicator extends to at least a distal portion of the first limb member and corresponds to an axis along the drive path that is parallel to the joint member axis.

Clause 100. The non-transitory computer-readable medium of clause 85, wherein the first trajectory indicator corresponds to an axis that intersects with the first axis at a distal portion of the first limb member and is parallel to the joint member axis and the drive path.

Clause 101. The non-transitory computer-readable medium of clause 85, wherein the second trajectory indicator extends to at least a distal portion of the second limb member and corresponds to an axis along the drive path that is different from and parallel to the joint member axis.

Clause 102. The non-transitory computer-readable medium of clause 85, wherein the second trajectory indicator corresponds to an axis that intersects with the second axis at a distal portion of the second limb member and is parallel to the joint member axis and the drive path.

Clause 103. The non-transitory computer-readable medium of any of clauses 82-102, wherein the computer system is further configured to determine a cutting path associated with the first medical device and cause the display to concurrently display a perspective view of the cutting path.

Clause 104. The non-transitory computer-readable medium of clause 103, wherein the cutting path corresponds to a trajectory of a knife of the first medical device.

Clause 105. The non-transitory computer-readable medium of any of clauses 82-104, wherein the computer executable instructions further cause the one or more processors to:

determine an emplacement of an affected region based at least in part on the determined emplacement of the first virtual medical device; and causing the display to concurrently display a perspective view of:

a 3D rendering of at least a portion of the affected region based at least in part on the determined emplacement of the virtual medical device, or an affected region intersection indicator indicating an intersection between a trajectory of the affected region along the drive path.

Clause 106. The non-transitory computer-readable medium of clause 105, wherein the affected region corresponds to a volume located between the first limb member and the second limb member.

Clause 107. The non-transitory computer-readable medium of clause 105, wherein the at least a portion of the affected region comprises a stapling path of at least one staple of the first medical device.

Clause 108. The non-transitory computer-readable medium of clause 105, wherein the at least a portion of the affected region comprises a cutting path of a knife of the first medical device.

Clause 109. The non-transitory computer-readable medium of clause 105, wherein the at least a portion of the affected region comprises the intersection between the affected region and the medical image.

Clause 110. The non-transitory computer-readable medium of any of clauses 82-109, wherein the computer executable instructions further cause the one or more processors to determine an intersection between the affected region and the medical image.

Clause 111. The non-transitory computer-readable medium of any of clauses 82-110, wherein the computer executable instructions further cause the one or more processors to receive operating parameters corresponding to the first medical device and determine the emplacement of an affected region based at least in part on the received operating parameters.

Clause 112. The non-transitory computer-readable medium of any of clauses 82-110, wherein the computer executable instructions further cause the one or more processors to:

determine an emplacement of a plane-of-interest based at least in part on the determined emplacement of one of the medical image;

determine an emplacement of a ghost medical device based at least in part on the determined emplacement of the first virtual medical device and the determined emplacement of the plane-of-interest; and cause the display to concurrently display a perspective view of a 3D rendering of at least a portion of the ghost medical device on the plane-of-interest based at least in part on the determined emplacement of the ghost medical device.

Clause 113. The non-transitory computer-readable medium of any of clauses 82-110, wherein the computer executable instructions further cause the one or more processors to:

determine an emplacement of a plane-of-interest based at least in part on the determined emplacement of one of the first virtual medical device;

determine an emplacement of a ghost medical image based at least in part on the determined emplacement of the medical image and the determined emplacement of the plane-of-interest; and cause the display to currently display a perspective view of a 3D rendering of at least a portion of the ghost medical image on the plane-of-interest based at least in part on the determined emplacement of the ghost medical image.

Clause 114. The non-transitory computer-readable medium of any one of clause 112 or 73, wherein the computer executable instructions further cause the one or more processors to project the display object on the plane-of-interest to display the ghost display object.

Clause 115. The non-transitory computer-readable medium of Clause 114, wherein the computer executable instructions further cause the one or more processors to determine at least one of portions, points, or coordinates of the plane-of-interest that are closest to the display object.

Clause 116. The non-transitory computer-readable medium of any of clauses 114 or 115, wherein the computer executable instructions further cause the one or more processors to determine an arc path corresponding to the display object and the plane-of-interest.

Clause 117. The non-transitory computer-readable medium of any of clauses 114-116, wherein the computer executable instructions further cause the one or more processors to determine which of a plurality of connecting lines intersect the display object, wherein the plurality of connecting lines extend orthogonally from the plane-of-interest to the display object.

Clause 118. The non-transitory computer-readable medium of any of clauses 114-117, wherein the computer executable instructions further cause the one or more processors to use a virtual light source that is at least as large as the display object to be projected, wherein the light source is distal the plane-of-interest relative to the display object.

Clause 119. The non-transitory computer-readable medium of any of clauses 114-118, wherein the ghost display object includes a cross-section and/or outline of display object.

Clause 120. The non-transitory computer-readable medium of any of clauses 114-119, wherein the ghost display object includes a cross-section and/or outline of display object.

Clause 121. The method of any of the Clauses 3-40, wherein the received first emplacement data and the received second emplacement data correspond to a first position sensor.

Clause 122. The system of any of clauses 43-80, wherein the received first emplacement data and the received second emplacement data correspond to a first position sensor.

Clause 123. The non-transitory computer-readable medium of any of clauses 83-120, wherein the received first emplacement data and the received second emplacement data correspond to a first position sensor.

Various example embodiments of methods, systems and non-transitory computer-readable medium relating to projecting a display object onto a plane-of-interest to display a ghost display object can be found in the following clauses:

Clause 1. A method for medical instrument navigation, the method comprising:

receiving first emplacement data associated with a first medical device;

receiving second emplacement data associated with a second medical device;

receiving a medical image corresponding to the second medical device;

determining an emplacement of a first display object corresponding to the first medical device based at least in part on the received first emplacement data;

determining an emplacement of a second display object corresponding to the second medical device based at least in part on the received second emplacement data;

determining an emplacement of the medical image based at least in part on the received second emplacement data;

determining an emplacement of a plane-of-interest based at least in part on the emplacement of one of the first display object or the medical image;

determining an emplacement of a ghost display object based at least in part on the determined emplacement of the other of the first display object or the medical image display object and the determined emplacement of the plane-of-interest; and causing one or more displays to concurrently display a perspective view of:
  a 3D rendering of at least a portion of the first display object based at least in part on the determined emplacement of the first display object,
  a 3D rendering of at least a portion of the second display object based at least in part on the determined emplacement of the second display object,
  a 3D rendering of at least a portion of the medical image based at least in part on the determined emplacement of the medical image,
  a 3D rendering of at least a portion of the ghost display object on the plane-of-interest based at least in part on the determined emplacement of the ghost display object.

Clause 2. A method for medical instrument navigation, the method comprising:

determining an emplacement of a display object;

determining an emplacement of a plane-of-interest;

determining an emplacement of a ghost display object based at least in part on the determined emplacement of the display object and the determined emplacement the plane-of-interest; and causing one or more displays to display concurrently display:
　a 3D rendering of at least a portion of the display object, and
　a 3D rendering of at least a portion of the ghost display object on the plane-of-interest.

Clause 3. The method of Clause 2, further comprising:
　receiving first emplacement data associated with a first medical device;
　receiving second emplacement data associated with a second medical device;
　wherein said determining the emplacement of the display object is based at least in part on the received first emplacement data and said determining the emplacement of the plane-of-interest is based at least in part on the received second emplacement data.

Clause 4. The method of Clause 3, further comprising
　receiving a medical image corresponding to the second medical device; and
　determining an emplacement of the medical image based at least in part on the received second emplacement data,
　wherein said determining the emplacement of the plane-of-interest is based at least in part on the determined emplacement of the medical image.

Clause 5. The method of Clause 3, further comprising
　receiving a medical image corresponding to the first medical device; and
　determining an emplacement of the medical image based at least in part on the received first emplacement data,
　wherein said determining the emplacement of the display object is based at least in part on the determined emplacement of the medical image.

Clause 6. The method of any of clauses 2-5, further comprising projecting the display object on the plane-of-interest to display the ghost display object.

Clause 7. The method of any of clauses 6-6, wherein said projecting comprises determining at least one of portions, points, or coordinates of the plane-of-interest that are closest to the display object.

Clause 8. The method of any of clauses 6-7, wherein said projecting comprises determining an arc path corresponding to the display object and the plane-of-interest.

Clause 9. The method of any of clauses 6-8, wherein said projecting comprises determining which of a plurality of connecting lines intersect the display object, wherein the plurality of connecting lines extend orthogonally from the plane-of-interest to the display object.

Clause 10. The method of any of clauses 6-9, wherein said projecting comprises using a virtual light source that is at least as large as the display object to be projected, wherein the virtual light source is distal to the plane-of-interest relative to the display object.

Clause 11. The method of any of clauses 2-10, wherein the ghost display object includes a cross-section and/or outline of display object.

Clause 12. The method of any of clauses 2-11, wherein the ghost display object corresponds to at least one of a virtual medical device, a medical image, or an affected region.

Clause 13. The method of any of clauses 2-12, wherein the plane-of-interest corresponds to at least one of a medical device plane or an image plane.

Clause 14. The method of any of clauses 2-13, wherein the display object is an affected region and wherein the affected region corresponds to a volume located between a first limb member and a second limb member of a medical device.

Clause 15. The method of any of clauses 2-14, wherein the display object is an affected region and wherein the affected region comprises a stapling path of at least one staple of a medical device.

Clause 16. The method of any of clauses 2-15, wherein the display object is an affected region and wherein the affected region comprises a cutting path of a knife of a medical device.

Clause 17. A system comprising:
　a computer system in communication with a display, the computer system comprising a computer processor and a non-transitory storage medium, wherein the computer system is configured to:
　　receive first emplacement data associated with a first medical device,
　　receive second emplacement data associated with a second medical device,
　　receive a medical image corresponding to the second medical device,
　　determine an emplacement of a first display object corresponding to the first medical device based at least in part on the received first emplacement data,
　　determine an emplacement of a second display object corresponding to the second medical device based at least in part on the received second emplacement data,
　　determine an emplacement of the medical image based at least in part on the received second emplacement data,
　　determine an emplacement of a plane-of-interest based at least in part on the emplacement of one of the first display object or the medical image,
　　determine an emplacement of a ghost display object based at least in part on the determined emplacement of the other of the first display object or the medical image display object and the determined emplacement of the plane-of-interest, and
　　cause a display to concurrently display a perspective view of:
　　　a 3D rendering of at least a portion of the first display object based at least in part on the determined emplacement of the first display object,
　　　a 3D rendering of at least a portion of the second display object based at least in part on the determined emplacement of the second display object,
　　　a 3D rendering of at least a portion of the medical image based at least in part on the determined emplacement of the medical image,
　　　a 3D rendering of at least a portion of the ghost display object on the plane-of-interest based at least in part on the determined emplacement of the ghost display object; and
　　the display.

Clause 18. A system comprising:
　a computer system in communication with a display, the computer system comprising a computer processor and a non-transitory storage medium, wherein the computer system is configured to:
　　determine an emplacement of a display object,
　　determine an emplacement of a plane-of-interest,
　　determine an emplacement of a ghost display object based at least in part on the determined emplacement of the display object and the determined emplacement the plane-of-interest, and
　　cause one or more displays to display concurrently display:
　　　a 3D rendering of at least a portion of the display object, and a 3D rendering of at least a portion of the ghost display object on the plane-of-interest; and
the display.

Clause 19. The system of Clause 18, wherein the computer system is further configured to:
receive first emplacement data associated with a first medical device;
receiving second emplacement data associated with a second medical device;
wherein said determining the emplacement of the display object is based at least in part on the received first emplacement data and said determining the emplacement of the plane-of-interest is based at least in part on the received second emplacement data.

The system of Clause 19, wherein the computer system is further configured to:
receive a medical image corresponding to the second medical device;
determine an emplacement of the medical image based at least in part on the received second emplacement data; and
determine the emplacement of the plane-of-interest based at least in part on the determined emplacement of the medical image.

Clause 20. The system of Clause 19, wherein the computer system is further configured to:
receive a medical image corresponding to the first medical device;
determine an emplacement of the medical image based at least in part on the received first emplacement data; and
determine the emplacement of the display object based at least in part on the determined emplacement of the medical image.

Clause 21. The system of any of clauses 18-21, wherein the computer system is further configured to project the display object on the plane-of-interest to display the ghost display object.

Clause 22. The system of any of clauses 21-22, wherein the computer system is further configured to determine at least one of portions, points, or coordinates of the plane-of-interest that are closest to the display object.

Clause 23. The system of any of clauses 21-23, wherein the computer system is further configured to determine an arc path corresponding to the display object and the plane-of-interest.

Clause 24. The system of any of clauses 21-24, wherein the computer system is further configured to determine which of a plurality of connecting lines intersect the display object, wherein the plurality of connecting lines extend orthogonally from the plane-of-interest to the display object.

Clause 25. The system of any of clauses 21-25, wherein the computer system is further configured to use a virtual light source that is at least as large as the display object to be projected, wherein the virtual light source is distal to the plane-of-interest relative to the display object.

Clause 26. The system of any of clauses 18-26, wherein the ghost display object includes a cross-section and/or outline of display object.

Clause 27. The system of any of clauses 18-27, wherein the ghost display object corresponds to at least one of a virtual medical device, a medical image, or an affected region.

Clause 28. The system of any of clauses 18-28, wherein the plane-of-interest corresponds to at least one of a medical device plane or an image plane.

Clause 29. The system of any of clauses 18-29, wherein the display object is an affected region and wherein the affected region corresponds to a volume located between a first limb member and a second limb member of a medical device.

Clause 30. The system of any of clauses 18-30, wherein the display object is an affected region and wherein the affected region comprises a stapling path of at least one staple of a medical device.

Clause 31. The system of any of clauses 18-31, wherein the display object is an affected region and wherein the affected region comprises a cutting path of a knife of a medical device.

Clause 32. A non-transitory computer-readable medium comprising computer executable instructions that when executed by one or more processors cause the one or more processors to:
receive first emplacement data associated with a first medical device,
receive second emplacement data associated with a second medical device,
receive a medical image corresponding to the second medical device,
determine an emplacement of a first display object corresponding to the first medical device based at least in part on the received first emplacement data,
determine an emplacement of a second display object corresponding to the second medical device based at least in part on the received second emplacement data,
determine an emplacement of the medical image based at least in part on the received second emplacement data,
determine an emplacement of a plane-of-interest based at least in part on the emplacement of one of the first display object or the medical image,
determine an emplacement of a ghost display object based at least in part on the determined emplacement of the other of the first display object or the medical image display object and the
determined emplacement of the plane-of-interest, and
cause a display to concurrently display a perspective view of:
a 3D rendering of at least a portion of the first display object based at least in part on the determined emplacement of the first display object,
a 3D rendering of at least a portion of the second display object based at least in part on the determined emplacement of the second display object,
a 3D rendering of at least a portion of the medical image based at least in part on the determined emplacement of the medical image,
a 3D rendering of at least a portion of the ghost display object on the plane-of-interest based at least in part on the determined emplacement of the ghost display object.

Clause 33. A non-transitory computer-readable medium comprising computer executable instructions that when executed by one or more processors cause the one or more processors to:
determine an emplacement of a display object,
determine an emplacement of a plane-of-interest,
determine an emplacement of a ghost display object based at least in part on the determined emplacement of the display object and the determined emplacement the plane-of-interest, and
cause one or more displays to display concurrently display:
a 3D rendering of at least a portion of the display object, and a 3D rendering of at least a portion of the ghost display object on the plane-of-interest.

Clause 34. The non-transitory computer-readable medium of Clause 18, wherein the computer executable instructions further cause the one or more processors to:

receive first emplacement data associated with a first medical device;

receiving second emplacement data associated with a second medical device;

wherein said determining the emplacement of the display object is based at least in part on the received first emplacement data and said determining the emplacement of the plane-of-interest is based at least in part on the received second emplacement data.

Clause 35. The non-transitory computer-readable medium of Clause 19, wherein the computer executable instructions further cause the one or more processors to:

receive a medical image corresponding to the second medical device;

determine an emplacement of the medical image based at least in part on the received second emplacement data; and determine the emplacement of the plane-of-interest based at least in part on the determined emplacement of the medical image.

Clause 36. The non-transitory computer-readable medium of Clause 19, wherein the computer executable instructions further cause the one or more processors to:

receive a medical image corresponding to the first medical device;

determine an emplacement of the medical image based at least in part on the received first emplacement data; and determine the emplacement of the display object based at least in part on the determined emplacement of the medical image.

Clause 37. The non-transitory computer-readable medium of any of clauses 18-21, wherein the computer executable instructions further cause the one or more processors to project the display object on the plane-of-interest to display the ghost display object.

Clause 38. The non-transitory computer-readable medium of any of clauses 21-22, wherein the computer executable instructions further cause the one or more processors to determine at least one of portions, points, or coordinates of the plane-of-interest that are closest to the display object.

Clause 39. The non-transitory computer-readable medium of any of clauses 21-23, wherein the computer executable instructions further cause the one or more processors to determine an arc path corresponding to the display object and the plane-of-interest.

Clause 40. The non-transitory computer-readable medium of any of clauses 21-24, wherein the computer executable instructions further cause the one or more processors to determine which of a plurality of connecting lines intersect the display object, wherein the plurality of connecting lines extend orthogonally from the plane-of-interest to the display object.

Clause 41. The non-transitory computer-readable medium of any of clauses 21-25, wherein the computer executable instructions further cause the one or more processors to use a virtual light source that is at least as large as the display object to be projected, wherein the virtual light source is distal to the plane-of-interest relative to the display object.

Clause 42. The non-transitory computer-readable medium of any of clauses 18-26, wherein the ghost display object includes a cross-section and/or outline of display object.

Clause 43. The non-transitory computer-readable medium of any of clauses 18-27, wherein the ghost display object corresponds to at least one of a virtual medical device, a medical image, or an affected region.

Clause 44. The non-transitory computer-readable medium of any of clauses 18-28, wherein the plane-of-interest corresponds to at least one of a medical device plane or an image plane.

Clause 45. The non-transitory computer-readable medium of any of clauses 18-29, wherein the display object is an affected region and wherein the affected region corresponds to a volume located between a first limb member and a second limb member of a medical device.

Clause 46. The non-transitory computer-readable medium of any of clauses 18-30, wherein the display object is an affected region and wherein the affected region comprises a stapling path of at least one staple of a medical device.

Clause 47. The non-transitory computer-readable medium of any of clauses 18-31, wherein the display object is an affected region and wherein the affected region comprises a cutting path of a knife of a medical device.

Various example embodiments of methods, systems and non-transitory computer-readable medium relating to displaying an affected region of a medical device can be found in the following clauses:

Clause 1. A method for medical instrument navigation, the method comprising:

receiving emplacement data associated with a medical device, the medical device comprising a joint member having a joint member axis, a first limb member having a first axis, and a second limb member having a second axis that is different from the joint member axis and the first axis;

receiving operating parameters corresponding to the medical device;

determining an emplacement of a virtual medical device corresponding to the medical device based at least in part on the received emplacement data;

determining an emplacement of an affected region based at least in part on the received emplacement data and the operating parameters, wherein the affected region corresponds to a volume located between the first limb member and the second limb member; and causing one or more displays to concurrently display a perspective view of:

a 3D rendering of at least a portion of the virtual medical device based at least in part on the determined emplacement of the virtual medical device, the 3D rendering of the virtual medical device including at least the first limb member and the second limb member, and a 3D rendering of at least a portion of the affected region based at least in part on the determined emplacement of the affected region, or an intersection indicator indicating an intersection between an image plane and a trajectory of the affected region along a drive path that is parallel to the joint member axis.

Clause 2. A method for medical instrument navigation, the method comprising:

determining an emplacement of a virtual medical device corresponding to a medical device, the medical device comprising a joint member having a joint member axis, a first limb member having a first axis, and a second limb member having a second axis that is different from the joint member axis and the first axis;

determining an emplacement of an affected region based at least in part on the determined emplacement of the virtual medical device; and causing one or more displays to display at least one of:
a 3D rendering of at least a portion of the affected region based at least in part on the determined emplacement of the virtual medical device, or
an intersection indicator indicating an intersection between an image plane and a trajectory of the affected region along a drive path that is parallel to the joint member axis.

Clause 3. The method of Clause 2, further comprising:
receiving emplacement data associated with the medical device; and
receiving operating parameters corresponding to the medical device,
wherein said determining the emplacement of the virtual medical device is based at least in part on the received emplacement data, wherein said determining the emplacement of the affected region is based at least in part on the received emplacement data and the operating parameters.

Clause 4. The method of Clause 2, wherein the 3D rendering of the virtual medical includes at least the first limb member and the second limb member.

Clause 5. The method of Clause 2, further comprising causing the one or more displays to display a 3D rendering of at least a portion of the virtual medical device based at least in part on the determined emplacement of the virtual medical device, wherein the 3D rendering of the virtual medical device includes at least a first virtual limb member corresponding to the first limb member and a second virtual limb member corresponding to the second limb member.

Clause 6. The method of Clause 2, wherein the affected region corresponds to a volume located between the first limb member and the second limb member.

Clause 7. The method of Clause 2, wherein the affected region comprises a stapling path of at least one staple of the medical device.

Clause 8. The method of Clause 2, wherein the affected region comprises a cutting path of a knife of the medical device.

Clause 9. A system comprising:
a computer system in communication with a display, the computer system comprising a computer processor and a non-transitory storage medium, wherein the computer system is configured to:
receive emplacement data associated with a medical device, the medical device comprising a joint member having a joint member axis, a first limb member having a first axis, and a second limb member having a second axis that is different from the joint member axis and the first axis;
receive operating parameters corresponding to the medical device,
determine an emplacement of a virtual medical device corresponding to the medical device based at least in part on the received emplacement data,
determine an emplacement of an affected region based at least in part on the received emplacement data and the operating parameters, wherein the affected region corresponds to a volume located between the first limb member and the second limb member, and
cause a display to concurrently display a perspective view of:
a 3D rendering of at least a portion of the virtual medical device based at least in part on the determined emplacement of the virtual medical device, the 3D rendering of the virtual medical device including at least the first limb member and the second limb member, and a 3D rendering of at least a portion of the affected region based at least in part on the determined emplacement of the affected region, or
an intersection indicator indicating an intersection between an image plane and a trajectory of the affected region along a drive path that is parallel to the joint member axis; and
the display.

Clause 10. A system comprising:
a computer system in communication with a display, the computer system comprising a computer processor and a non-transitory storage medium, wherein the computer system is configured to:
determine an emplacement of a virtual medical device corresponding to a medical device, the medical device comprising a joint member having a joint member axis, a first limb member having a first axis, and a second limb member having a second axis that is different from the joint member axis and the first axis,
determine an emplacement of an affected region based at least in part on the determined emplacement of the virtual medical device, and
cause a display to display at least one of:
a 3D rendering of at least a portion of the affected region based at least in part on the determined emplacement of the virtual medical device, or
an intersection indicator indicating an intersection between an image plane and a trajectory of the affected region along a drive path that is parallel to the joint member axis; and
the display.

Clause 11. The system of Clause 10, wherein the computer system is further configured to:
receive emplacement data associated with the medical device;
receive operating parameters corresponding to the medical device;
determine the emplacement of the virtual medical device based at least in part on the received emplacement data; and
determine the emplacement of the affected region based at least in part on the received emplacement data and the operating parameters.

Clause 12. The system of any of clauses 10-11, wherein the 3D rendering of the virtual medical includes at least the first limb member and the second limb member.

Clause 13. The system of any of clauses 10-12, wherein the computer system is further configured to cause the display to display a 3D rendering of at least a portion of the virtual medical device based at least in part on the determined emplacement of the virtual medical device, wherein the 3D rendering of the virtual medical device includes at least a first virtual limb member corresponding to the first limb member and a second virtual limb member corresponding to the second limb member.

Clause 14. The system of any of clauses 10-13, wherein the affected region corresponds to a volume located between the first limb member and the second limb member.

Clause 15. The system of any of clauses 10-14, wherein the affected region comprises a stapling path of at least one staple of the medical device.

Clause 16. The system of any of clauses 10-15, wherein the affected region comprises a cutting path of a knife of the medical device.

Clause 17. A non-transitory computer-readable medium comprising computer executable instructions that when executed by one or more processors cause the one or more processors to:

receive emplacement data associated with a medical device, the medical device comprising a joint member having a joint member axis, a first limb member having a first axis, and a second limb member having a second axis that is different from the joint member axis and the first axis;

receive operating parameters corresponding to the medical device, determine an emplacement of a virtual medical device corresponding to the medical device based at least in part on the received emplacement data, determine an emplacement of an affected region based at least in part on the received emplacement data and the operating parameters, wherein the affected region corresponds to a volume located between the first limb member and the second limb member, and cause a display to concurrently display a perspective view of:
  a 3D rendering of at least a portion of the virtual medical device based at least in part on the determined emplacement of the virtual medical device, the 3D rendering of the virtual medical device including at least the first limb member and the second limb member, and
  a 3D rendering of at least a portion of the affected region based at least in part on the determined emplacement of the affected region, or
  an intersection indicator indicating an intersection between an image plane and a trajectory of the affected region along a drive path that is parallel to the joint member axis.

Clause 18. A non-transitory computer-readable medium comprising computer executable instructions that when executed by one or more processors cause the one or more processors to:
  determine an emplacement of a virtual medical device corresponding to a medical device, the medical device comprising a joint member having a joint member axis, a first limb member having a first axis, and a second limb member having a second axis that is different from the joint member axis and the first axis,
  determine an emplacement of an affected region based at least in part on the determined emplacement of the virtual medical device, and
  cause a display to display at least one of:
    a 3D rendering of at least a portion of the affected region based at least in part on the determined emplacement of the virtual medical device, or
    an intersection indicator indicating an intersection between an image plane and a trajectory of the affected region along a drive path that is parallel to the joint member axis.

Clause 19. The non-transitory computer-readable medium of Clause 18, wherein the computer executable instructions further cause the one or more processors to:
  receive emplacement data associated with the medical device;
  receive operating parameters corresponding to the medical device;
  determine the emplacement of the virtual medical device based at least in part on the received emplacement data; and
  determine the emplacement of the affected region based at least in part on the received emplacement data and the operating parameters.

Clause 20. The non-transitory computer-readable medium of any of clauses 18-19, wherein the 3D rendering of the virtual medical includes at least the first limb member and the second limb member.

Clause 21. The non-transitory computer-readable medium of any of clauses 18-20, wherein the computer executable instructions further cause the one or more processors to cause the display to display a 3D rendering of at least a portion of the virtual medical device based at least in part on the determined emplacement of the virtual medical device, wherein the 3D rendering of the virtual medical device includes at least a first virtual limb member corresponding to the first limb member and a second virtual limb member corresponding to the second limb member.

Clause 22. The non-transitory computer-readable medium of any of clauses 18-21, wherein the affected region corresponds to a volume located between the first limb member and the second limb member.

Clause 23. The non-transitory computer-readable medium of any of clauses 18-22, wherein the affected region comprises a stapling path of at least one staple of the medical device.

Clause 24. The non-transitory computer-readable medium of any of clauses 18-23, wherein the affected region comprises a cutting path of a knife of the medical device.

Various example embodiments of methods, systems and non-transitory computer-readable medium relating to determining emplacement of a virtual medical device and a medical image based at least in part on received emplacement data associated with a medical device can be found in the following clauses:

Clause 1. A method for medical instrument navigation, the method comprising:
  receiving emplacement data associated with a first medical device, the first medical device comprising a joint member having a joint member axis, a first limb member having a first axis, and a second limb member having a second axis that is different from the joint member axis and the first axis;
  determining an emplacement of a first virtual medical device corresponding to the first medical device based at least in part on the received emplacement data;
  determining an emplacement of a second virtual medical device corresponding to a second medical device based at least in part on the received emplacement data;
  determining an emplacement of a medical image based at least in part on the received emplacement data; and
  causing one or more displays to concurrently display a perspective view of:
    a 3D rendering of at least a portion of the first virtual medical device based at least in part on the determined emplacement of the first virtual medical device, the 3D rendering of the first virtual medical device including at least the first limb member and the second limb member,
    a 3D rendering of at least a portion of the second virtual medical device based at least in part on the determined emplacement of the second virtual medical device, and
    a 3D rendering of at least a portion of the medical image based at least in part on the determined emplacement of the medical image.

Clause 2. A method for medical instrument navigation, the method comprising: determining an emplacement of a display object based at least in part on first emplacement data;
  determining an emplacement of a medical image based at least in part on the first emplacement data; and causing one or more displays to concurrently display:
    a 3D rendering of at least a portion of the display object, and
    a 3D rendering of at least a portion of the medical image.

Clause 3. The method of Clause 2, wherein the display object is a first virtual medical device corresponding to a first medical device comprising a joint member having a joint member axis, a first limb member having a first axis, and a second limb member having a second axis that is different from the joint member axis and the first axis.

Clause 4. The method of Clause 3, further comprising:
    receiving the first emplacement data, the first emplacement data associated with the first medical device; and
    determining an emplacement of a second virtual medical device corresponding to a second medical device based at least in part on the received first emplacement data.

Clause 5. The method of any of clauses 2-4, wherein the display object is a first virtual medical device and wherein causing the one or more displays to concurrently display further comprises causing concurrent display a 3D rendering of at least a portion of the first virtual medical device.

Clause 6. The method of Clause 5, the 3D rendering of at least a portion of the first virtual medical device includes at least a first limb member and a second limb member of the virtual medical device.

Clause 7. The method of any of clauses 2-6, where causing one or more displays to concurrently display further comprises causing the one or more displays to display:
    a 3D rendering of at least a portion of the second virtual medical device based at least in part on the determined emplacement of the second virtual medical device; and
    a 3D rendering of at least a portion of the medical image based at least in part on the determined emplacement of the medical image.

Clause 8. A system comprising:
    a computer system in communication with a display, the computer system comprising a computer processor and a non-transitory storage medium, wherein the computer system is configured to:
        receive emplacement data associated with a first medical device, the first medical device comprising a joint member having a joint member axis, a first limb member having a first axis, and a second limb member having a second axis that is different from the joint member axis and the first axis,
        determine an emplacement of a first virtual medical device corresponding to the first medical device based at least in part on the received emplacement data,
        determine an emplacement of a second virtual medical device corresponding to a second medical device based at least in part on the received emplacement data,
        determine an emplacement of a medical image based at least in part on the received emplacement data, and
        cause a display to concurrently display a perspective view of:
            a 3D rendering of at least a portion of the first virtual medical device based at least in part on the determined emplacement of the first virtual medical device, the 3D rendering of the first virtual medical device including at least the first limb member and the second limb member,
            a 3D rendering of at least a portion of the second virtual medical device based at least in part on the determined emplacement of the second virtual medical device, and
            a 3D rendering of at least a portion of the medical image based at least in part on the determined emplacement of the medical image; and
    the display.

Clause 9. A system comprising:
    a computer system in communication with a display, the computer system comprising a computer processor and a non-transitory storage medium, wherein the computer system is configured to:
        determine an emplacement of a display object based at least in part on first emplacement data,
        determine an emplacement of a medical image based at least in part on the first emplacement data, and
        cause one or more displays to concurrently display:
            a 3D rendering of at least a portion of the display object, and
            a 3D rendering of at least a portion of the medical image; and
    the display.

Clause 10. The system of Clause 9, wherein the display object is a first virtual medical device corresponding to a first medical device comprising a joint member having a joint member axis, a first limb member having a first axis, and a second limb member having a second axis that is different from the joint member axis and the first axis.

Clause 11. The system of Clause 10, wherein the computer system is further configured to:
    receive the first emplacement data, the first emplacement data associated with the first medical device; and
    determine an emplacement of a second virtual medical device corresponding to a second medical device based at least in part on the received first emplacement data.

Clause 12. The system of any of clauses 9-11, wherein the display object is a first virtual medical device and the computer system is further configured to cause the display to concurrently display a 3D rendering of at least a portion of the first virtual medical device.

Clause 13. The system of Clause 12, the 3D rendering of at least a portion of the first virtual medical device includes at least a first limb member and a second limb member of the virtual medical device.

Clause 14. The system of any of clauses 9-14, where the computer system is further configured to cause the display to concurrently display:
    a 3D rendering of at least a portion of the second virtual medical device based at least in part on the determined emplacement of the second virtual medical device; and
    a 3D rendering of at least a portion of the medical image based at least in part on the determined emplacement of the medical image.

Clause 15. A non-transitory computer-readable medium comprising computer executable instructions that when executed by one or more processors cause the one or more processors to:
    receive emplacement data associated with a first medical device, the first medical device comprising a joint member having a joint member axis, a first limb member having a first axis, and a second limb member having a second axis that is different from the joint member axis and the first axis,
    determine an emplacement of a first virtual medical device corresponding to the first medical device based at least in part on the received emplacement data,
    determine an emplacement of a second virtual medical device corresponding to a second medical device based at least in part on the received emplacement data, determine an emplacement of a medical image based at least in part on the received emplacement data, and
cause a display to concurrently display a perspective view of:
a 3D rendering of at least a portion of the first virtual medical device based at least in part on the determined emplacement of the first virtual medical device, the 3D rendering of the first virtual medical device including at least the first limb member and the second limb member,
a 3D rendering of at least a portion of the second virtual medical device based at least in part on the determined emplacement of the second virtual medical device, and
a 3D rendering of at least a portion of the medical image based at least in part on the determined emplacement of the medical image.

Clause 16. A non-transitory computer-readable medium comprising computer executable instructions that when executed by one or more processors cause the one or more processors to:
determine an emplacement of a display object based at least in part on first emplacement data,
determine an emplacement of a medical image based at least in part on the first emplacement data, and
cause one or more displays to concurrently display:
a 3D rendering of at least a portion of the display object, and
a 3D rendering of at least a portion of the medical image.

Clause 17. The system of Clause 16, wherein the display object is a first virtual medical device corresponding to a first medical device comprising a joint member having a joint member axis, a first limb member having a first axis, and a second limb member having a second axis that is different from the joint member axis and the first axis.

Clause 18. The non-transitory computer-readable medium of Clause 17, wherein the computer executable instructions further cause the one or more processors to:
receive the first emplacement data, the first emplacement data associated with the first medical device; and
determine an emplacement of a second virtual medical device corresponding to a second medical device based at least in part on the received first emplacement data.

Clause 19. The non-transitory computer-readable medium of any of clauses 16-18, wherein the display object is a first virtual medical device and wherein the computer executable instructions further cause the one or more processors to cause the display to concurrently display a 3D rendering of at least a portion of the first virtual medical device.

Clause 20. The non-transitory computer-readable medium of Clause 19, the 3D rendering of at least a portion of the first virtual medical device includes at least a first limb member and a second limb member of the virtual medical device.

Clause 21. The non-transitory computer-readable medium of any of clauses 16-20, wherein the computer executable instructions further cause the one or more processors to cause the display to concurrently display:
a 3D rendering of at least a portion of the second virtual medical device based at least in part on the determined emplacement of the second virtual medical device; and
a 3D rendering of at least a portion of the medical image based at least in part on the determined emplacement of the medical image.

Terminology

Conditional language, such as, among others, "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof means any connection or coupling, either direct or indirect, between two or more elements; the coupling or connection between the elements can be physical, logical, or a combination thereof. Additionally, the words "herein," "above," "below," and words of similar import, when used in this application, refer to this application as a whole and not to any particular portions of this application. Where the context permits, words in the above Detailed Description using the singular or plural number may also include the plural or singular number respectively. The word "or" in reference to a list of two or more items, covers all of the following interpretations of the word: any one of the items in the list, all of the items in the list, and any combination of the items in the list. Likewise the term "and/or" in reference to a list of two or more items, covers all of the following interpretations of the word: any one of the items in the list, all of the items in the list, and any combination of the items in the list.

Depending on the embodiment, certain operations, acts, events, or functions of any of the algorithms described herein can be performed in a different sequence, can be added, merged, or left out altogether (non-limiting example: not all are necessary for the practice of the algorithms). Moreover, in certain embodiments, operations, acts, functions, or events can be performed concurrently, non-limiting examples: through multi-threaded processing, interrupt processing, or multiple processors or processor cores or on other parallel architectures, rather than sequentially.

The various illustrative logical blocks, modules, routines, and algorithm steps described in connection with the embodiments disclosed herein can be implemented as electronic hardware, or as a combination of electronic hardware and executable software. To clearly illustrate this interchangeability, various illustrative components, blocks, modules, and steps have been described above generally in terms of their functionality. Whether such functionality is implemented as hardware, or as software that runs on hardware, depends upon the particular application and design constraints imposed on the overall system 100. The described functionality can be implemented in varying ways for each particular application, but such implementation decisions should not be interpreted as causing a departure from the scope of the disclosure.

Moreover, the various illustrative logical blocks and modules described in connection with the embodiments disclosed herein can be implemented or performed by a machine, such as a processor device, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor device can be a microprocessor, but in the alternative, the processor device can be a controller, microcontroller, or combinations of the same, or the like. A processor device can include electrical circuitry configured to process computer-executable instructions. In another embodiment, a processor device includes an FPGA or other programmable device that performs logic operations without processing computer-executable instructions. A processor device can also be implemented as a combination of computing devices, non-limiting examples: a combination of a DSP and a microprocessor, a plurality of microprocessors, one or more microprocessors in conjunction with a DSP core, or any other such configuration. Although described herein primarily with respect to digital technology, a processor device may also include primarily analog components. For example, some or all of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

Further, the processing of the various components of the illustrated systems can be distributed across multiple machines, networks, and other computing resources. In addition, two or more components of a system can be combined into fewer components. Various components of the illustrated systems can be implemented in one or more virtual machines, rather than in dedicated computer hardware systems and/or computing devices.

Virtualization technologies allow a single physical computing device to host one or more instances of a virtual machine, which virtual machine instance appears to a user as an independent computing device. With virtualization, the host computing device can create, maintain, delete, or otherwise manage virtual machines instances in a dynamic manner. In turn, users can request computing resources, including single computing devices or a configuration of networked computing devices, and be provided with virtual machine instances that provide the requested computing resources.

An instance of a virtual machine may be configured to provide specific functionality. For example, a virtual machine instance may be associated with different combinations of software applications and operating systems or operating system configurations to enable a virtual machine to provide different desired functionalities, or to provide similar functionalities more efficiently.

Any patents and applications and other references noted above, including any that may be listed in accompanying filing papers, are incorporated herein by reference. Aspects of the invention can be modified, if necessary, to employ the systems, functions, and concepts of the various references described above to provide yet further implementations of the invention.

These and other changes can be made to the invention in light of the above Detailed Description. While the above description describes certain examples of the invention, and describes the best mode contemplated, no matter how detailed the above appears in text, the invention can be practiced in many ways. Details of the system may vary considerably in its specific implementation, while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific examples disclosed in the specification, unless the above Detailed Description section explicitly defines such terms. Accordingly, the actual scope of the invention encompasses not only the disclosed examples, but also all equivalent ways of practicing or implementing the invention under the claims.

To reduce the number of claims, certain aspects of the invention are presented below in certain claim forms, but the applicant contemplates the various aspects of the invention in any number of claim forms. For example, while only one aspect of the invention may be recited as a means-plus-function claim under 35 U.S.C sec. 112(f) (AIA), other aspects may likewise be embodied as a means-plus-function claim, or in other forms, such as being embodied in a computer-readable medium. Any claims intended to be treated under 35 U.S.C. § 112(f) will begin with the words "means for", but use of the term "for" in any other context is not intended to invoke treatment under 35 U.S.C. § 112(f). Accordingly, the applicant reserves the right to pursue additional claims after filing this application, in either this application or in a continuing application.

Disjunctive language such as the phrase "at least one of X, Y, or Z," unless specifically stated otherwise, is otherwise understood with the context as used in general to present that an item, term, etc., may be either X, Y, or Z, or any combination thereof (non-limiting examples: X, Y, and/or Z). Thus, such disjunctive language is not generally intended to, and should not, imply that certain embodiments require at least one of X, at least one of Y, or at least one of Z to each be present.

Unless otherwise explicitly stated, articles such a "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

While the above detailed description has shown, described, and pointed out novel features as applied to various embodiments, it can be understood that various omissions, substitutions, and changes in the form and details of the devices or algorithms illustrated can be made without departing from the spirit of the disclosure. As can be recognized, certain embodiments described herein can be embodied within a form that does not provide all of the features and benefits set forth herein, as some features can be used or practiced separately from others. The scope of certain embodiments disclosed herein is indicated by the appended claims rather than by the foregoing description. All changes which come within the meaning and range of equivalency of the claims are to be embraced within their scope.

The previous description of the disclosed implementations is provided to enable a person skilled in the art to make or use the present invention. Various modifications to these implementations will be readily apparent to those skilled in the art, and the generic principles defined herein can be applied to other implementations without departing from the spirit or scope of the invention. Furthermore, although described above with reference to medical devices and procedures, it will be understood that the embodiments described herein can be applied to other systems in which non-medical objects are tracked and non-medical image streams are received, and virtual representations are displayed on a display and/or systems in which multiple objects are displayed on a display within a virtual space, such as within a virtual 3D space. Thus, the present invention is not intended to be limited to the implementations shown herein but is to be accorded the widest scope consistent with the principles and novel features disclosed herein.

The invention claimed is:

1. A method for medical device navigation, the method comprising:
   determining an emplacement of a first medical display object;
   determining an emplacement of a plane-of-interest;
   determining an emplacement of a second medical display object based at least in part on the determined emplacement of the first medical display object and the determined emplacement of the plane-of-interest; and
   causing a display to display, in a virtual 3D space, at least a portion of the second medical display object based on the determined emplacement of the second medical display object.

2. The method of claim 1, wherein the second medical display object is at least a partial representation of the first medical display object, and wherein the second medical display object is displayed on the plane-of-interest.

3. The method of claim 1, wherein the first medical display object and the second medical display object correspond to a first physical medical device, and wherein the plane-of-interest corresponds to a scanning plane of a second physical medical device.

4. The method of claim 3, further comprising:
   receiving medical image data from the second physical medical device; and
   causing the display to display, in the virtual 3D space, at least a portion of a medical image based at least in part on the determined emplacement of the plane-of-interest, wherein the medical image corresponds to the medical image data.

5. The method of claim 3, further comprising causing the display to display, in the virtual 3D space, at least a portion of the first medical display object based at least in part on the determined emplacement of the first medical display object.

6. The method of claim 3, wherein the first physical medical device comprises at least one of a grasper, a stapler, a vessel sealer, an electrocautery device, a resecting device, a transecting device, or a medical needle.

7. The method of claim 3, wherein the first physical medical device comprises a joint member having a joint member axis, a first limb member having a first axis, and a second limb member having a second axis that is different from the joint member axis and the first axis.

8. The method of claim 7, further comprising:
   determining an emplacement of an affected region, wherein the affected region comprises a volume located between the first limb member and the second limb member; and
   causing the display to display, in the virtual 3D space, at least a portion of the affected region based on the determined emplacement of the affected region.

9. The method of claim 8, wherein the affected region corresponds to at least one of a stapling path of a staple of the first physical medical device or a cutting path of the first physical medical device.

10. A method for medical device navigation, the method comprising:
    determining an emplacement of a medical device, wherein the medical device comprises a first jaw member having a first axis and a second jaw member having a second axis that is different from the first axis;
    determining an emplacement of a plane-of-interest;
    determining an intersection between the plane-of-interest and a trajectory of the first jaw member along a drive path of the medical device; and
    causing a display to display, in a virtual 3D space, an intersection indicator indicating the intersection.

11. The method of claim 10, further comprising:
    causing the display to display, in the virtual 3D space, a second intersection indicator that indicates an intersection between the plane-of-interest and the trajectory the second jaw member along the drive path of the medical device.

12. The method of claim 10, further comprising:
    receiving medical image data; and
    causing the display to display a medical image based at least in part on the medical image data and the determined emplacement of the plane-of-interest.

13. The method of claim 10, further comprising causing the display to display a medical display object based at least in part on the determined emplacement of the medical device, wherein the medical display object comprises a representation of at least a portion of the first jaw member and at least a portion of the second jaw member.

14. The method of claim 10, wherein the plane-of-interest corresponds to a scanning plane of a second physical medical device.

15. The method of claim 10, wherein the medical device comprises at least one of a grasper, a stapler, a vessel sealer, a resecting device, or a transecting device.

16. A method for medical device navigation, the method comprising:
    determining an emplacement of a medical device, wherein the medical device comprises a first jaw member and a second jaw member;
    identifying an emplacement of an affected region of the medical device based at least in part on the determined emplacement of the medical device, wherein the affected region corresponds to at least a portion of a volume located between the first jaw member and the second jaw member; and causing a display to display, in a virtual 3D space, at least a portion of the affected region based at least in part on the determined emplacement of the affected region.

17. The method of claim 16, wherein the medical device comprises at least one of a grasper, a stapler, a vessel sealer, a resecting device, or a transecting device.

18. The method of claim 16, further comprising:
receiving medical image data;
determining an emplacement of a plane-of-interest; and
causing the display to display a medical image based at least in part on the medical image data and the determined emplacement of the plane-of-interest.

19. The method of claim 18, further comprising:
determining an emplacement of a medical display object based at least in part on the determined emplacement of the medical device and the determined emplacement of the plane-of-interest; and
causing the display to display, in the virtual 3D space, at least a portion of the medical display object based on the determined emplacement of the medical device.

20. The method of claim 16, further comprising causing the display to display a medical display object based at least in part on the determined emplacement of the medical device, wherein the medical display object comprises a representation of at least a portion of the first jaw member and at least a portion of the second jaw member.

21. A system, comprising
one or more processors communicatively coupled with a display; and
a non-transitory computer-readable storage medium storing computer-executable instructions that when executed by the one or more processors cause the one or more processors to:
determine an emplacement of a first medical display object;
determine an emplacement of a plane-of-interest;
determine an emplacement of a second medical display object based at least in part on the determined emplacement of the first medical display object and the determined emplacement of the plane-of-interest; and
cause the display to display, in a virtual 3D space, at least a portion of the second medical display object based on the determined emplacement of the second medical display object.

22. A system, comprising
one or more processors communicatively coupled with a display; and
a non-transitory computer-readable storage medium storing computer-executable instructions that when executed by the one or more processors cause the one or more processors to:
determine an emplacement of a medical device, wherein the medical device comprises a first jaw member having a first axis and a second jaw member having a second axis that is different from the first axis;
determine an emplacement of a plane-of-interest;
determine an intersection between the plane-of-interest and a trajectory of the first jaw member along a drive path of the medical device; and
cause the display to display, in a virtual 3D space, an intersection indicator indicating the intersection.

23. A system, comprising
one or more processors communicatively coupled with a display; and
a non-transitory computer-readable storage medium storing computer-executable instructions that when executed by the one or more processors cause the one or more processors to:
determine an emplacement of a medical device, wherein the medical device comprises a first jaw member and a second jaw member;
identify an emplacement of an affected region of the medical device based at least in part on the determined emplacement of the medical device, wherein the affected region corresponds to at least a portion of a volume located between the first jaw member and the second jaw member; and
cause the display to display, in a virtual 3D space, at least a portion of the affected region based at least in part on the determined emplacement of the affected region.

* * * * *